United States Patent [19]

Takaya et al.

[11] Patent Number: 4,960,766

[45] Date of Patent: Oct. 2, 1990

[54] CEPHEM COMPOUNDS

[75] Inventors: Takao Takaya; Kazuo Sakane; Kenzi Miyai, all of Kawanishi; Kohji Kawabata, Osaka, all of Japan

[73] Assignee: Fujisawa Pharmaceutical Co., Ltd., Osaka, Japan

[21] Appl. No.: 930,427

[22] Filed: Nov. 14, 1986

[30] Foreign Application Priority Data

Nov. 22, 1985 [GB] United Kingdom ............... 8528803
May 1, 1986 [GB] United Kingdom ............... 8610720

[51] Int. Cl.$^5$ ................. C07D 501/36; A61K 31/545
[52] U.S. Cl. .................................... 514/202; 540/222
[58] Field of Search .................... 540/222; 514/202

[56] References Cited

U.S. PATENT DOCUMENTS

| | | |
|---|---|---|
| 4,401,668 | 8/1983 | Lunn . |
| 4,427,675 | 1/1984 | Ayres et al. . |
| 4,464,368 | 8/1984 | O'Callaghan et al. . |
| 4,563,522 | 1/1986 | Takaya et al. ............... 540/222 |
| 4,616,081 | 10/1986 | Nishihida et al. ........... 540/222 |

FOREIGN PATENT DOCUMENTS

| | | |
|---|---|---|
| 0047977 | 3/1982 | European Pat. Off. . |
| 0135142 | 3/1985 | European Pat. Off. . |
| 0137441 | 4/1985 | European Pat. Off. . |
| 60-67483 | 4/1985 | Japan . |
| 60-67484 | 4/1985 | Japan . |
| 2036724 | 7/1980 | United Kingdom . |

*Primary Examiner*—Nicholas S. Rizzo
*Attorney, Agent, or Firm*—Oblon, Spivak, McClelland, Maier & Neustadt

[57] ABSTRACT

The invention relates to cephem compounds characterized by a substituted 2-pyrazoliomethyl group and a 7-(aminothiazolyl)(alkoxyimino)-acetamido group and certain derivatives thereof, to pharmaceutical compositions comprising the same and to use for treatment of infections diseases.

12 Claims, No Drawings

CEPHEM COMPOUNDS

The present invention relates to new cephem compounds and pharmaceutically acceptable salts thereof.

More particularly, it relates to new cephem compounds and pharmaceutically acceptable salts thereof, which have antimicrobial activities, to processes for preparation thereof, to pharmaceutical composition comprising the same, and to a method for treating infectious diseases in human being or animals.

Accordingly, one object of the present invention is to provide the cephem compounds and pharmaceutically acceptable salts thereof, which are highly active against a number of pathogenic microorganisms.

Another object of the present invention is to provide processes for the preparation of the cephem compounds and salts thereof.

A further object of the present invention is to provide a pharmaceutical composition comprising, as an active ingredient, said cephem compounds or their pharmaceutically acceptable salts.

Still further object of the present invention is to provide a method for treating infectious diseases caused by pathogenic microorganisms, which comprises administering said cephem compounds to infected human being or animals.

The object cephem compounds are novel and can be represented by the following general formula [I]:

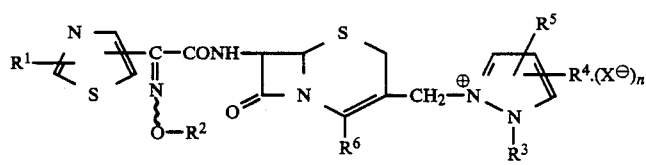

wherein
$R^1$ is amino or protected amino,
$R^2$ is hydrogen, hydroxy protective group, lower alkyl, dihalogenated lower alkyl, cyclo(lower)alkenyl, thietanyl, carboxy(lower)alkyl or protected carboxy(lower)alkyl,
$R^3$ is lower alkyl,
$R^4$ and $R^5$ are each hydrogen, lower alkyl, hydroxy(lower)alkyl, lower alkoxy, amino or protected amino,
$R^6$ is $COO^\ominus$, carboxy or protected carboxy,
$X^\ominus$ is an anion, and
n is 0 or 1,
with proviso that
(i) when $R^2$ is carboxy(lower)alkyl or protected carboxy(lower)alkyl, then $R^4$ is hydrogen and $R^5$ is amino,
(ii) when $R^6$ is $COO^\ominus$, then n is 0, and (iii) when $R^6$ is carboxy or protected carboxy, then n is 1.

As to the object compounds [I], the following points are to be noted.

That is, the object compounds [I] include syn isomer, anti isomer and a mixture thereof. Syn isomer means one geometrical isomer having the partial structure represented by the following formula:

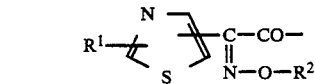

(wherein $R^1$ and $R^2$ are each as defined above), and anti isomer means the other geometrical isomer having the partial structure represented by the following formula:

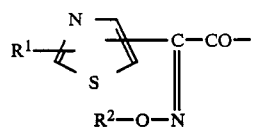

(wherein $R^1$ and $R^2$ are each as defined above), and all of such geometrical isomers and mixture thereof are included within the scope of this invention.

In the present specification and claim, the partial structure of these geometrical isomers and mixture thereof are represented for convenient sake by the following formula:

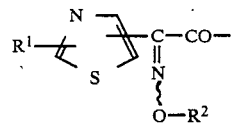

(wherein $R^1$ and $R^2$ are each as defined above).

Another point to be noted is that the pyrazolio moiety of the compounds [I] can also exist in the tautomeric form, and such tautomeric equilibrium can be represented by the following scheme.

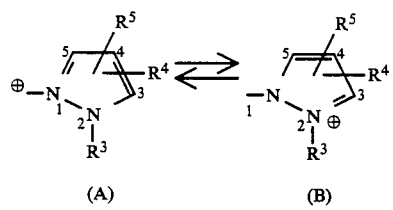

(A)  (B)

(wherein $R^3$, $R^4$ and $R^5$ are each as defined above).

Both of the above tautomeric isomers are included within the scope of the present invention, and in the present specification and claim, however, the object compounds [I] are represented for the convenient sake by one expression of the polymeric group of the formula (A).

The cephem compounds [I] of the present invention can be prepared by processes as illustrated in the following reaction schemes.

-continued
Process 1
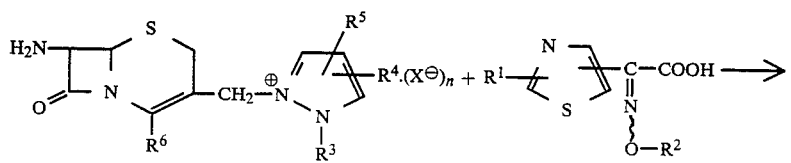
[II]
or its reactive
derivative at the
amino group,
or its salt
[III]
or its reactive
derivative at the
carboxy group,
or its salt
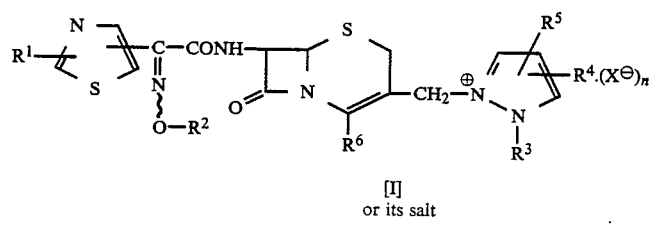
[I]
or its salt
Process 2
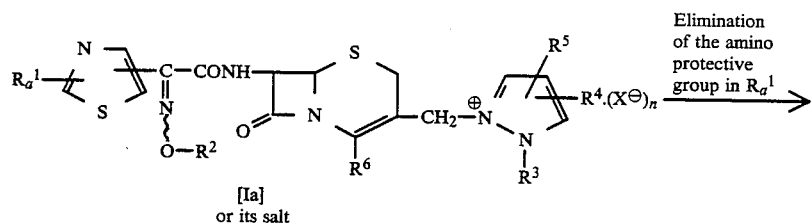
[Ia]
or its salt
Elimination
of the amino
protective
group in $R_a^1$
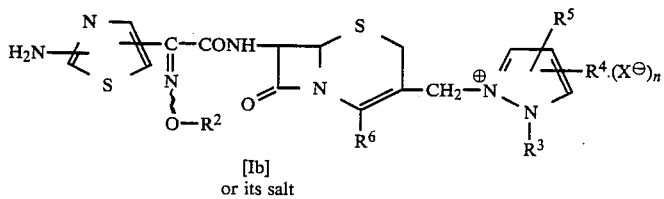
[Ib]
or its salt
Process 3
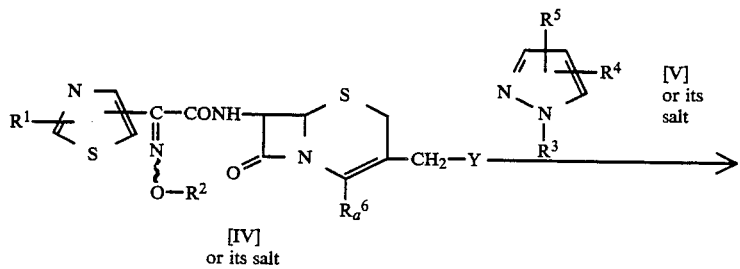
[IV]
or its salt
[V]
or its
salt
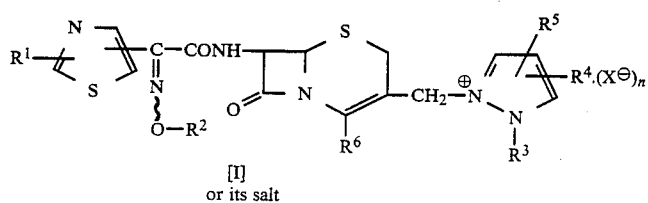
[I]
or its salt -continued
Process 4
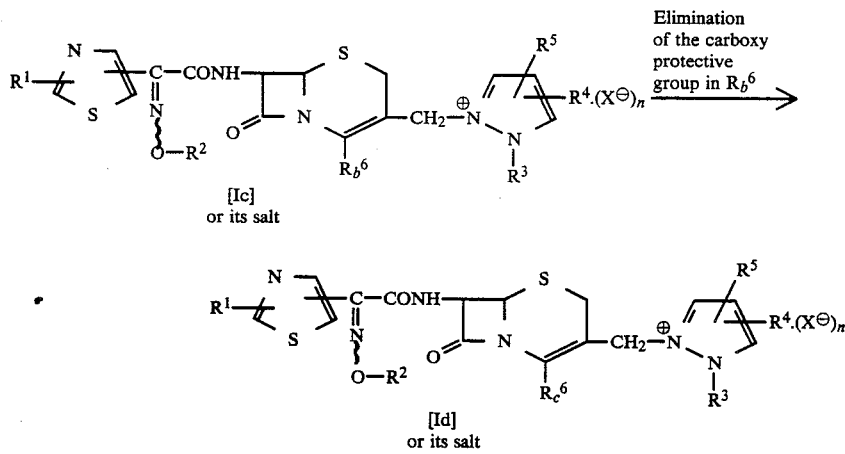
[Ic] or its salt
Elimination of the carboxy protective group in $R_b^6$ →
[Id] or its salt
Process 5
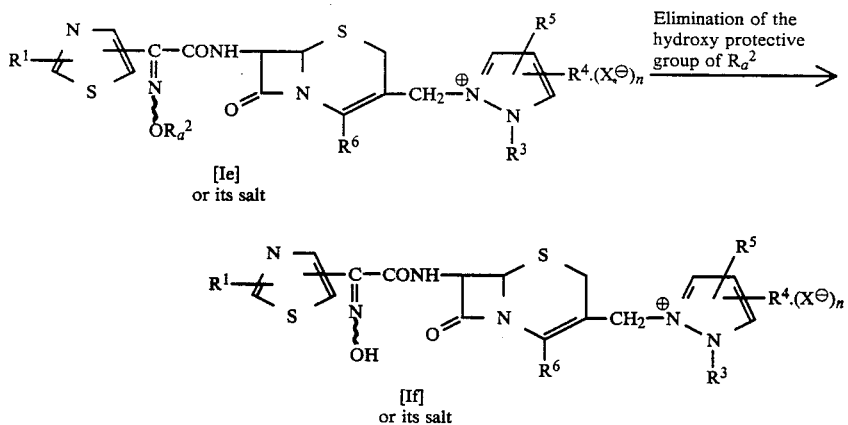
[Ie] or its salt
Elimination of the hydroxy protective group of $R_a^2$ →
[If] or its salt
Process 6
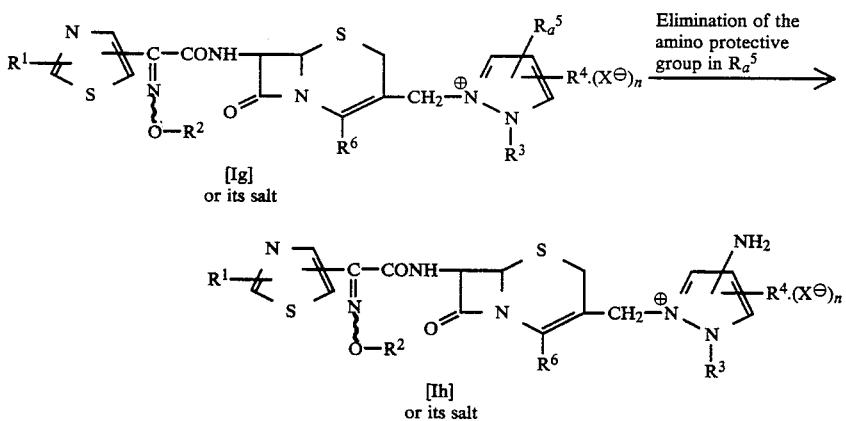
[Ig] or its salt
Elimination of the amino protective group in $R_a^5$ →
[Ih] or its salt
Process 7
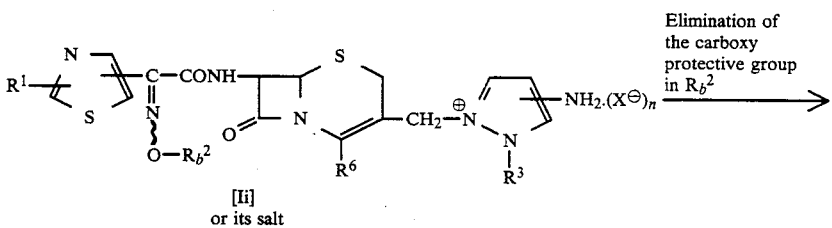
[Ii] or its salt
Elimination of the carboxy protective group in $R_b^2$ →

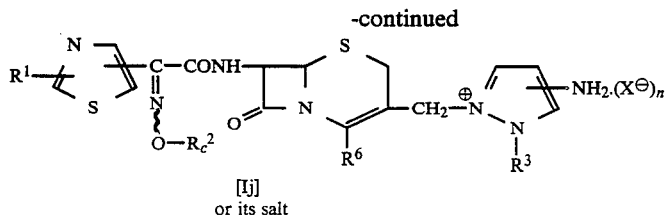

[Ij] or its salt

Process 8

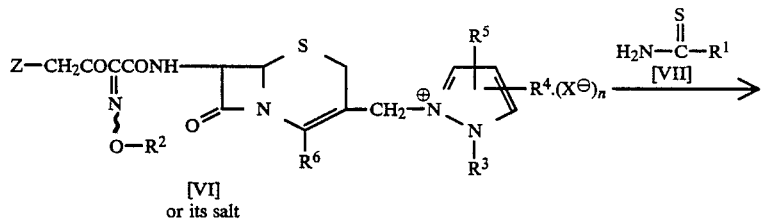

[Ik] or its salt

Process 9

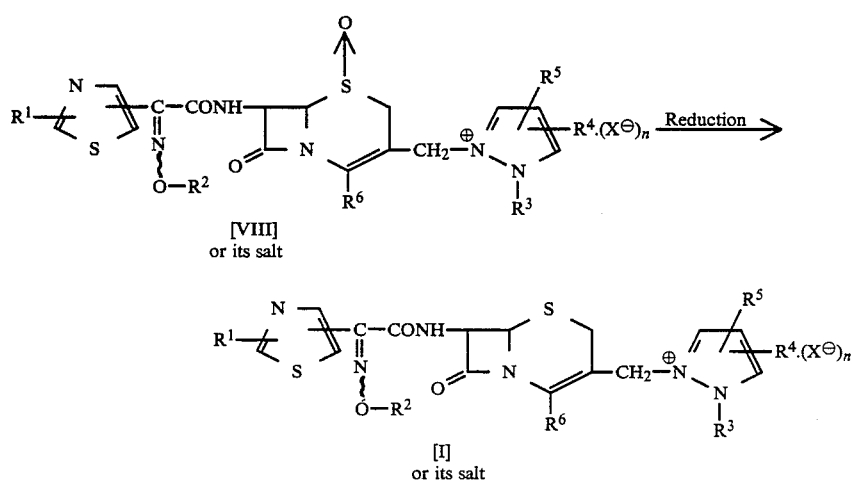

[I] or its salt wherein $R^1$, $R^2$, $R^3$, $R^4$, $R^5$, $R^6$, $X^\ominus$ and n are each as defined above, $R_a^1$ is protected amino,
$R_a^2$ is hydroxy protective group,
$R_b^2$ is protected carboxy(lower)alkyl,
$R_c^2$ is carboxy(lower)alkyl,
$R_a^5$ is protected amino,
$R_a^6$ is carboxy or protected carboxy,
$R_b^6$ is protected carboxy,
$R_c^6$ is $COO^\ominus$ or carboxy,
Y is a leaving group,
Z is an acid residue.

In the above and subsequent descriptions of this specification, suitable examples of the various definitions are explained in detail as follows:

The term "lower" is intended to mean 1 to 6 carbon atom(s), unless otherwise indicated.

Suitable protective group in the protected amino group may include ar(lower)alkyl such as mono or di or triphenyl-(lower)alkyl [e.g. benzyl, phenethyl, 1-phenylethyl, benzhydryl, trityl, etc.], acyl as explained hereinbelow, and the like.

Suitable acyl may be aliphatic acyl, aromatic acyl, arylaliphatic acyl and heterocyclic-aliphatic acyl derived from carboxylic acid, carbonic acid, carbamic acid, sulfonic acid, and the like.

Suitable example of the acyl group thus explained may be lower alkanoyl [e.g. formyl, acetyl, propionyl, hexanoyl, pivaloyl, etc.], mono(or di or tri)-(halo(lower)alkanoyl [e.g. chloroacetyl, trifluoroacetyl, etc.], lower alkoxycarbonyl [e.g. methoxycarbonyl, ethoxycarbonyl, tert-butoxycarbonyl, tert-pentyloxycarbonyl, hexyloxycarbonyl, etc.], mono(or di or tri)halo(lower)alkoxycarbonyl [e.g. chloromethoxy carbonyl, dichloroethoxycarbonyl, trichloroethoxycarbonyl, etc.], aroyl [e.g. benzoyl, toluoyl, xyloyl, naphthoyl, etc.], ar(lower)alkanoyl such as phenyl(lower)alkanoyl

[e.g. phenylacetyl, phenylpropionyl, etc.], aryloxycarbonyl [e.g. phenoxycarbonyl, naphthyloxycarbonyl, etc.], aryloxy(lower)alkanoyl such as phenoxy(lower)alkanoyl [e.g. phenoxyacetyl, phenoxypropionyl, etc.], arylglyoxyloyl [e.g. phenylglyoxyloyl, naphthylglyoxyloyl, etc.], ar(lower)alkoxycarbonyl which may have suitable substituent(s) such as phenyl(lower)alkoxycarbonyl which may have nitro or lower alkoxy [e.g. benzyloxycarbonyl, phenethyloxycarbonyl, p-nitrobenzyloxycarbonyl, p-methoxybenzyloxycarbonyl, etc.], thienylacetyl, imidazolylacetyl, furylacetyl, tetrazolylacetyl, thiazolylacetyl, thiadiazolylacetyl, thienylpropionyl, thiadiazolylpropionyl, lower alkylsulfonyl [e.g. methylsulfonyl, ethylsulfonyl, propylsulfonyl, isopropylsulfonyl, pentylsulfonyl, butylsulfonyl, etc.], arylsulfonyl [e.g. phenylsulfonyl, tolylsulfonyl, xylylsulfonyl, naphthylsulfonyl, etc.], ar(lower)-alkylsulfonyl such as phenyl(lower)alkylsulfonyl [e.g. benzylsulfonyl, phenethylsulfonyl, benzhydrylsulfonyl, etc.], and the like.

Preferable example of the protected amino group thus defined may be ar(lower)alkylamino and lower alkanoylamino, more preferable one may be triphenyl($C_1$-$C_4$)-alkylamino and $C_1$-$C_4$ alkanoylamino, and the most preferable one may be tritylamino and formamido.

Suitable "hydroxy protective group" may be acyl as exemplified above, tetrahydropyranyl [e.g. 2-tetrahydropyranyl, etc.], and the like, in which the preferred one may be 2-tetrahydropyranyl.

Suitable "lower alkyl" may be a straight or branched one such as methyl, ethyl, propyl, isopropyl, butyl, isobutyl, tert-butyl, pentyl, hexyl, or the like, in which the preferred one may be $C_1$-$C_4$alkyl and the most preferred one may be methyl and isopropyl.

Suitable "cyclo(lower)alkenyl" may be cyclopropenyl, cyclobutenyl, cyclopentenyl, cyclohexenyl, or the like, in which the preferred one may be cyclo($C_5$-$C_6$)alkenyl, more preferred one may be cyclopentenyl and the most preferred one may be 2-cyclopenten-1-yl and 3-cyclopenten-1-yl.

Suitable "dihalogenated lower alkyl" may be difluoromethyl, dichloromethyl, difluoroethyl, dichloroethyl, difluoropropyl, dichlorobutyl, difluorohexyl, or the like, in which the preferred one may be difluoro($C_1$-$C_4$)alkyl and the most preferred one may be difluoromethyl.

Suitable "thietanyl" may be 2- or 3-thietanyl.

Suitable "hydroxy(lower)alkyl" may be hydroxymethyl, hydroxyethyl, hydroxypropyl, hydroxybutyl, hydroxypentyl, hydroxyhexyl, or the like, in which the preferred one may be hydroxy($C_1$-$C_4$)alkyl and the most preferred one may be hydroxymethyl.

Suitable "lower alkoxy" may be a straight or branched one such as methoxy, ethoxy, propoxy, isopropoxy, butoxy, tert-butoxy, pentyloxy, hexyloxy or the like, in which the preferred one may be $C_1$-$C_4$alkoxy and the most preferred one may be methoxy.

Suitable "protected carboxy" may be an esterified carboxy group, or the like, and concrete examples of the ester moiety in said esterified carboxy group may be the ones such as lower alkyl ester [e.g. methyl ester, ethyl ester, propyl ester, isopropyl ester, butyl ester, isobutyl ester, tert-butyl ester, pentyl ester, hexyl ester, 1-cyclopropylethyl ester, etc.] which may have suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxymethyl ester, 2-propionyloxyethyl ester, hexanoyloxymethyl ester, etc.], lower alkanesulfonyl-(lower)alkyl ester [e.g. 2-mesylethyl ester, etc.] or mono(or di or tri)halo(lower)alkyl ester [e.g. 2-iodoethyl ester, 2,2,2-trichloroethyl ester, etc.]; lower alkenyl ester [e.g. vinyl ester, allyl ester, etc.]; lower alkynyl ester [e.g. ethynyl ester, propynyl ester, etc.]; ar(lower)alkyl ester which may have suitable substituent(s) [e.g. benzyl ester, 4-methoxybenzyl ester, 4-nitrobenzyl ester, phenethyl ester, trityl ester, benzhydryl ester, bis(methoxyphenyl)-methyl ester, 3,4-dimethoxybenzyl ester, 4-hydroxy-3,5-di-tert-butylbenzyl ester, etc.]; aryl ester which may have suitable substituent(s) [e.g. phenyl ester, 4-chlorophenyl ester, tolyl ester, 4-tert-butylphenyl ester, xylyl ester, mesityl ester, cumenyl ester, etc.]; or the like, in which the preferred one may be mono or di or triphenyl($C_1$-$C_4$)alkyl ester and the most preferred one may be benzhydryl ester.

Suitable "carboxy(lower)alkyl" may be carboxymethyl, 1-carboxyethyl, 2-carboxyethyl, 1-carboxy-1-methylethyl, 3-carboxypropyl, 2-carboxypropyl, 2-carboxymethylpropyl, 1-carboxybutyl, 2-carboxymethyl-2-methylpropyl, 5-carboxyhexyl, or the like, in which the preferred one may be carboxy ($C_1$-$C_4$)alkyl and the most preferred one may be carboxymethyl.

In the term "protected carboxy(lower)alkyl", suitable "protected carboxy" can be referred to the ones as exemplified before and the preferred "protected carboxy(lower)alkyl" may be esterified carboxy(lower)alkyl, in which more preferred one may be lower alkoxycarbonyl(lower)alkyl such as methoxycarbonylmethyl, ethoxycarbonylmethyl, tert-butoxycarbonylmethyl, 1-tert-butoxycarbonylethyl, 2-ethoxycarbonylethyl, 1-tert-butoxycarbonyl-1-methylethyl, 3-propoxycarbonylpropyl, 2-isopropoxycarbonylpropyl, 2-isobutoxycarbonylmethylpropyl, 1-tert-butoxycarbonylbutyl, 2-pentyloxycarbonylmethyl-2-methylpropyl, 5-hexyloxycarbonylhexyl or the like, and much more preferred one may be ($C_1$-$C_4$)alkoxycarbonyl($C_1$-$C_4$)alkyl, the most preferred one may be tert-butoxycarbonylmethyl.

Suitable "a leaving group" may be halogen [e.g. chlorine, bromine, iodine, etc.], acyloxy such as sulfonyloxy [e.g. benzenesulfonyloxy, tosyloxy, mesyloxy, etc.], lower alkanoyloxy [e.g. acetyloxy, propionyloxy, etc.], or the like.

Suitable "anion" may be formate, acetate, trifluoroacetate, maleate, tartrate, methanesulfonate, benzenesulfonate, toluenesulfonate, chloride, bromide, iodide, sulfate, phosphate, or the like.

Suitable "an acid residue" may be halogen (e.g. fluorine, chlorine, bromine, iodine) or acyloxy as exemplified above.

Suitable pharmaceutically acceptable salts of the object compound [I] are conventional non-toxic mono or di salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N-dibenzylethylenediamine salt, etc.], an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, hydriodide, sulfate, phosphate, etc.], a salt with an amino acid [e.g. arginine salt, aspartic acid salt, glutamic acid salt, etc.], and the like.

In this respect, it is to be noted the compounds [Ia], [Ib], [Ic], [Id], [Ie], [If], [Ig],[Ih], [Ii], [Ij] and [Ik] are included within the scope of the compounds [I], and accordingly the suitable salts of these compounds [Ia] to [Ik] are to be referred to those as exemplified for the object compounds [I] mentioned above.

The processes for preparing the object compounds of the present invention are explained in detail in the following.

PROCESS 1

The object compound [I] and its salt can be prepared by reacting a compound [II] or its reactive derivative at the amino group or a salt thereof with a compound [III] or its reactive derivative at the carboxy group or a salt thereof.

Suitable reactive derivative at the amino group of the compound [II] may include Schiff's base type imino or its tautomeric enamine type isomer formed by the reaction of the compound [II] with a carbonyl compound such as aldehyde, ketone or the like; a silyl derivative formed by the reaction of the compound [II] with a silyl compound such as bis(trimethylsilyl)acetamide, mono(-trimethylsilyl)acetamide, bis(trimethylsilyl)urea or the like; a derivative formed by reaction of the compound [II] with phosphorus trichloride or phosgene, and the like.

Suitable salts of the compound [II] and its reactive derivative can be referred to the ones as exemplified for the compound [I].

Suitable reactive derivative at the carboxy group of the compound [III] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole, tetrazole or 1-hydroxy-1H-benzotriazole; or an activated ester [e.g. cyanomethyl ester, methoxymethyl ester, dimethyliminomethyl [$(CH_3)_2\overset{+}{N}=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound [III] to be used.

Suitable salts of the compound [III] and its reactive derivative can be referred to the ones as exemplified for the compound [I].

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound [III] is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, methanesulfonyl chloride, etc.; or the like.

The reaction may also be carried out in the presence of an inorganic or organic base such as an alkali metal carbonate, alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

PROCESS 2

The object compound [Ib] and its salt can be prepared by subjecting a compound [Ia] or its salt to elimination reaction of the amino protective group in $R_a^1$.

This reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]-undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.].

The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the abovementioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

The present invention includes within the scope of the invention the case that the group of the formula: —O—$R^2$ (wherein $R^2$ is hydroxy protective group or cyclo(lower)alkenyl) is transformed into hydroxy during this reaction, the case that protected amino in $R^4$ and/or $R^5$ are transformed into amino, the case that protected carboxy in $R^6$ is transformed into carboxy and the case that protected carboxy(lower)alkyl in $R^2$ is transformed into carboxy(lower)alkyl.

PROCESS 3

The object compound [I] and its salt can be prepared by reacting a compound [IV] or its salt with a compound [V] or its salt.

Suitable salts of the compounds [IV] can be referred to the ones as exemplified for the compound [I].

Suitable salts of the compounds [V] may be an organic acid salt [e.g. formate, acetate, trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], or the like.

The present reaction may be carried out in a solvent such as water, phosphate buffer, acetone, chloroform, acetonitrile nitrobenzene, methylene, chloride, ethylene chloride, formamide, N,N-dimethylformamide, methanol, ethanol, diethyl ether, tetrahydrofuran, dimethyl sulfoxide, or any other organic solvent which does not adversely affect the reaction, preferably in ones having strong polarities. Among the solvents, hydrophilic solvents may be used in a mixture with water. When the compound [V] is in liquid, it can also be used as a solvent. The reaction is preferably conducted in the presence of a base, for example, inorganic base such as alkali-metal hydroxide, alkali metal carbonate, alkali metal bicarbonate, organic base such as trialkylamine, and the like. The reaction temperature is not critical, and the reaction is usually carried out at ambient temperature, under warming or under heating. The present reaction is preferably carried out in the presence of alkali metal halide [e.g. sodium iodide, potassium iodide, etc.], alkali metal thiocyanate [e.g. sodium thiocyanate, potassium thiocyanate, etc.] or the like.

Anion $X^\ominus$ may be the one derived from a leaving group Y and may be the other one converted therefrom by a conventional method.

PROCESS 4

The object compound [Id] and its salt can be prepared by subjecting a compound [Ic] or its salt to elimination reaction of the carboxy protective group in $R_b^6$.

This reaction can be carried out in a similar manner to that of Process 2 mentioned in the above, and therefore the reaction mode and reaction conditions [e.g. base, acid, catalyst, solvent, reaction temperature, etc.] of this reaction are to be referred to those as explained in Process 2.

The present invention includes within the scope of the invention the cases that protected amino in $R^1$ and/or $R^4$ and/or $R^5$ and/or the group of the formula: —O—$R^2$ (wherein $R^2$ is hydroxy protective group or cyclo(lower)alkenyl) and/or protected carboxy(lower)alkyl in $R^2$ are transformed into amino and/or hydroxy and/or carboxy(lower)alkyl, respectively during this reaction.

PROCESS 5

The object compound [If] and its salt can be prepared by subjecting a compound [Ie] or its salt to elimination reaction of the hydroxy protective group of $R_a^2$.

This reaction can be carried out in a similar manner to that of Process 2 mentioned in the above, and therefore the reaction mode and reaction conditions [e.g. base, acid, catalyst, solvent, reaction temperature, etc.] of this reaction are to be referred to those as explained in Process 2.

The present invention includes within the scope of the invention the cases that protected amino in $R^1$ and/or $R^4$ and/or $R^5$, and/or protected carboxy(lower)alkyl in $R^2$, and/or protected carboxy in $R^6$ are transformed into amino and/or carboxy(lower)alkyl and/or carboxy, respectively during this reaction.

PROCESS 6

The object compound [Ih] or its salt can be prepared by subjecting a compound [Ig] or its salt to elimination reaction of the amino protective group in $R_a^5$.

This reaction can be carried out in a similar manner to that of Process 2 mentioned in the above, and therefore the reaction mode and reaction conditions [e.g. base, acid, catalyst, solvent, reaction temperature, etc.] of this reaction are to be referred to those as explained in Process 2.

The present invention includes within the scope of the invention the cases that protected amino in $R^1$ and/or $R^4$, and/or protected carboxy in $R^6$, and/or protected carboxy(lower)alkyl in $R^2$, and/or the group of the formula: —O—$R^2$ (wherein $R^2$ is hydroxy protective group or cyclo(lower)alkenyl) are transformed into amino, and/or carboxy, and/or carboxy(lower)alkyl, and/or hydroxy, respectively during this reaction.

PROCESS 7

The object compound [Ij] and its salt can be prepared by subjecting a compound [Ii] or its salt to elimination reaction of the carboxy protective group in $R_b{}^2$.

This reaction can be carried out in a similar manner to that of Process 2 mentioned in the above, and therefore the reaction mode and reaction conditions [e.g. base, acid, catalyst, solvent, reaction temperature, etc.] of this reaction are to be referred to those as explained in Process 2.

The present invention includes within the scope of the invention the cases that protected amino in $R^1$ is transformed into amino during this reaction.

PROCESS 8

The compound [Ik] or its salt can be prepared by reacting the compound [VI] or its salt with the compound [VII].

Suitable salt of the compound [VI] may include the ones as exemplified for the compound [I].

This reaction is usually conducted in a conventional solvent which does not adversely influence the reaction such as ethyl acetate, methylene chloride, chloroform, carbon tetrachloride, tetrahydrofuran, N,N-dimethylformamide, N,N-dimethylacetamide, dioxane, water, acetic acid, formic acid, etc. or a mixture thereof.

The reaction temperature is not critical and the reaction is usually conducted under cooling to warming.

PROCESS 9

The object compound [I] or its salt can be prepared by reducing a compound [VIII] or its salt.

Suitable salts of the compound [VIII] can be referred to the ones as exemplified for the compound [I].

The present reduction can be carried out by a conventional method which is applied for the transformation of

into —S—, for example, by using phosphorus trichloride, a combination of stannous chloride and acetyl chloride, a combination of an alkali metal iodide [e.g. sodium iodide, etc.] and trihaloacetic anhydride [e.g. trifluoroacetic anhydride, etc.], and the like.

The present reduction is usually carried out in a solvent such as acetone, dioxane, acetonitrile, N,N-dimethylformamide, benzene, hexane, chloroform, methylene chloride, ethylene chloride, tetrahydrofuran, ethyl acetate, or any other solvent which does not adversely affect the reaction.

The reaction temperature is not critical and the reaction is usually carried out under cooling or at ambient temperature.

The anion of the compound [I] can be exchanged for another anion by a conventional method as described in Example mentioned later.

When the compound [I] obtained by the above Processes is in a form of salt, it can be transformed into its free form by a conventional method, e.g. reaction with a base or passing through a non-ionic adsorption resin, etc.

Some of the starting compounds [II] and [III] used in Process 1, all the starting compound [VI] used in Process 8 and all the starting compound [VIII] in Process 9 are new and such new starting compounds can be represented by the following formulas.

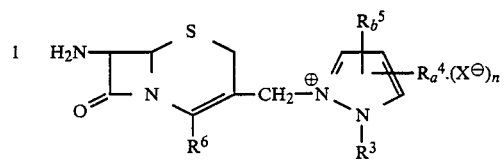

or its salt [IIa]

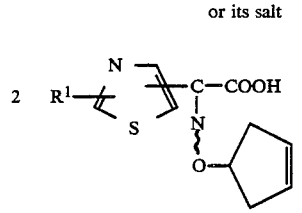

or its salt [III]

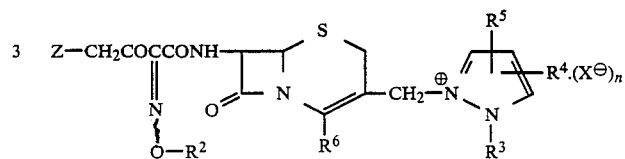

or its salt [VI]

-continued

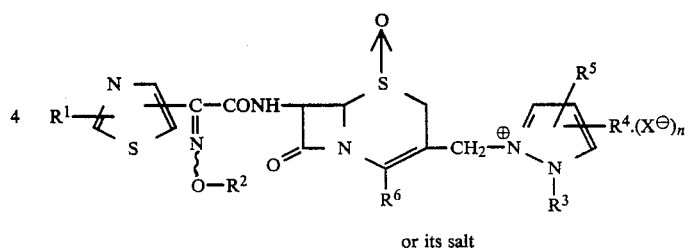

or its salt wherein $R^1$, $R^2$, $R^3$, $R^4$, $R^5$, $X^\ominus$, n and Z are each as defined above, $R_a^4$ and $R_b^5$ are each hydrogen, lower alkyl, hydroxy(lower)alkyl, lower alkoxy, amino or protected amino, with proviso that $R_a^4$ and $R_b^5$ are not hydrogens at the same time.

The new starting compounds [IIa], [IIIa], [VI] and [VIII] can be prepared by the following methods.

Method for the preparation of Compound [IIa]

Method A

Step 1

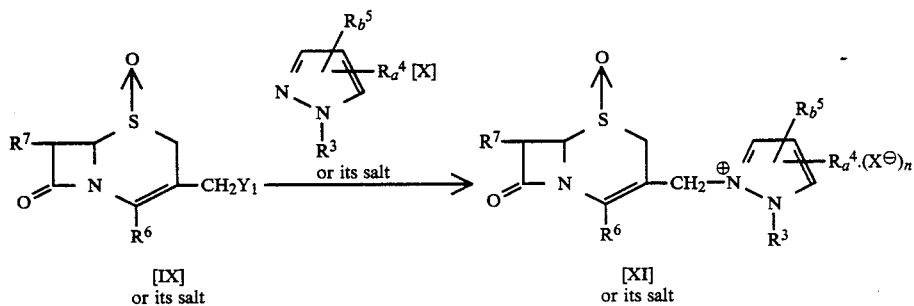

Step 2

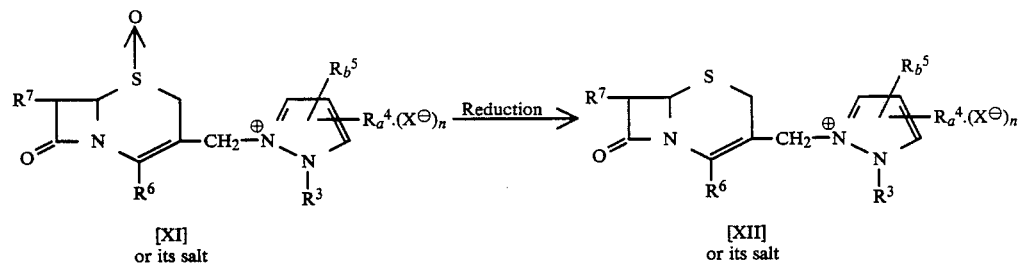

Step 3

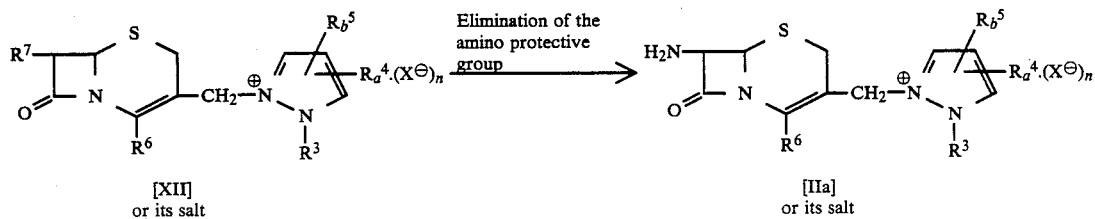

-continued
Method for the preparation of Compound [IIIa]
Method B
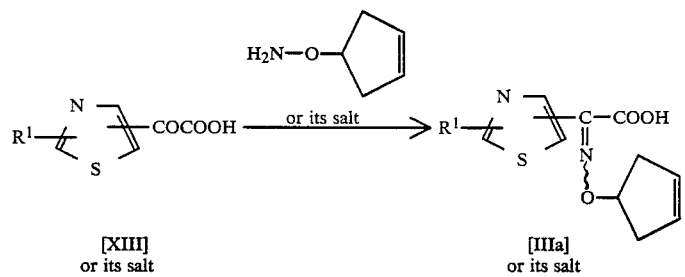
[XIII] or its salt → [IIIa] or its salt
Method for the preparation of Compound [VI]
Method C
Step 1
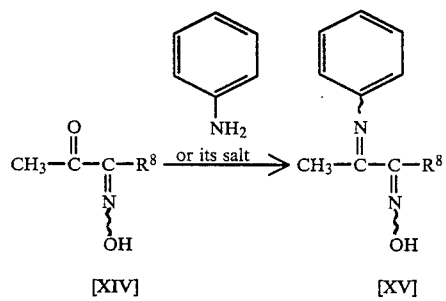
[XIV]    [XV]
Step 2
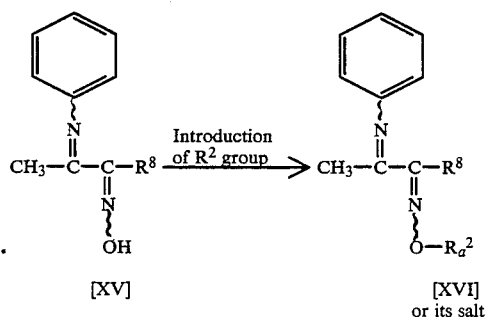
[XV]    [XVI] or its salt
Step 3
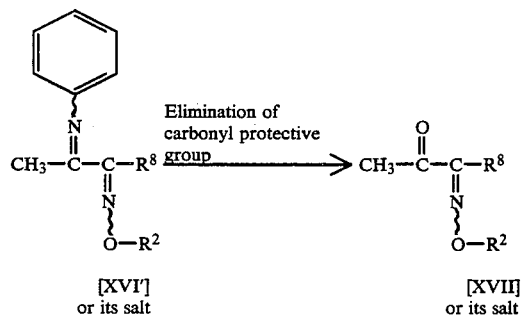
[XVI'] or its salt    [XVII] or its salt
Step 4
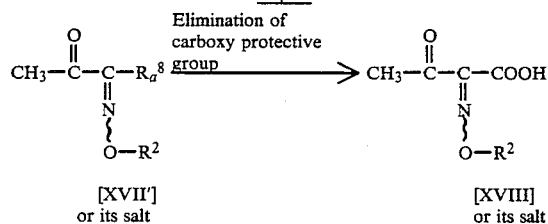
[XVII'] or its salt    [XVIII] or its salt

Step 5

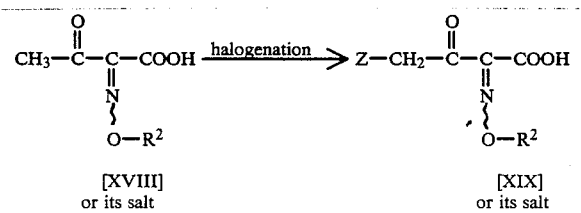

[XVIII] or its salt → [XIX] or its salt

Step 6

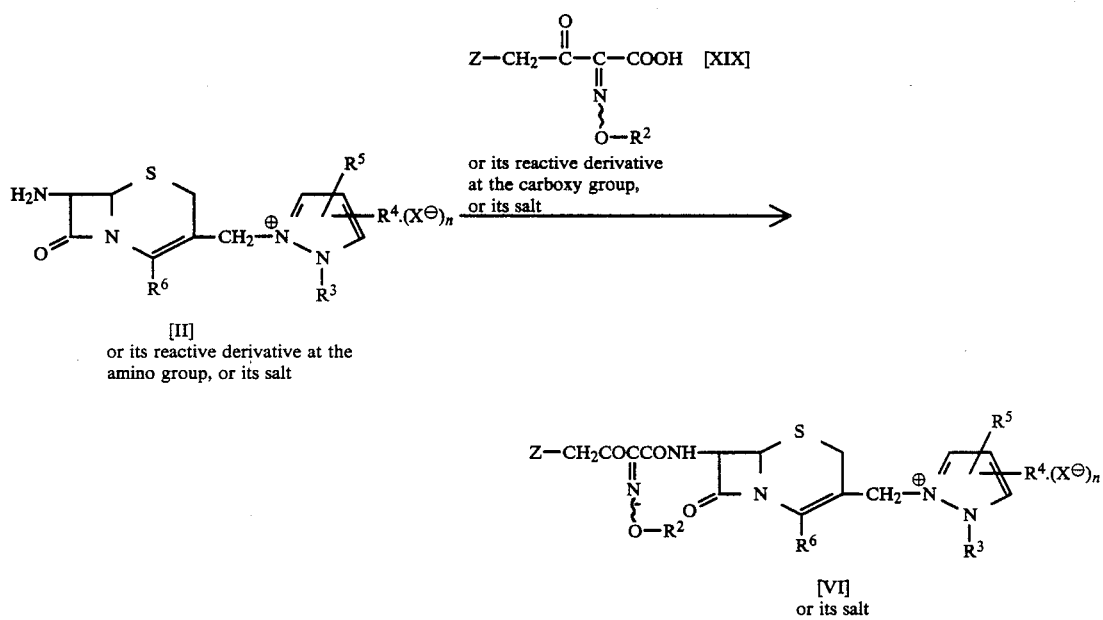

[VI] or its salt

Method for the preparation of Compound [VIII]
Method D

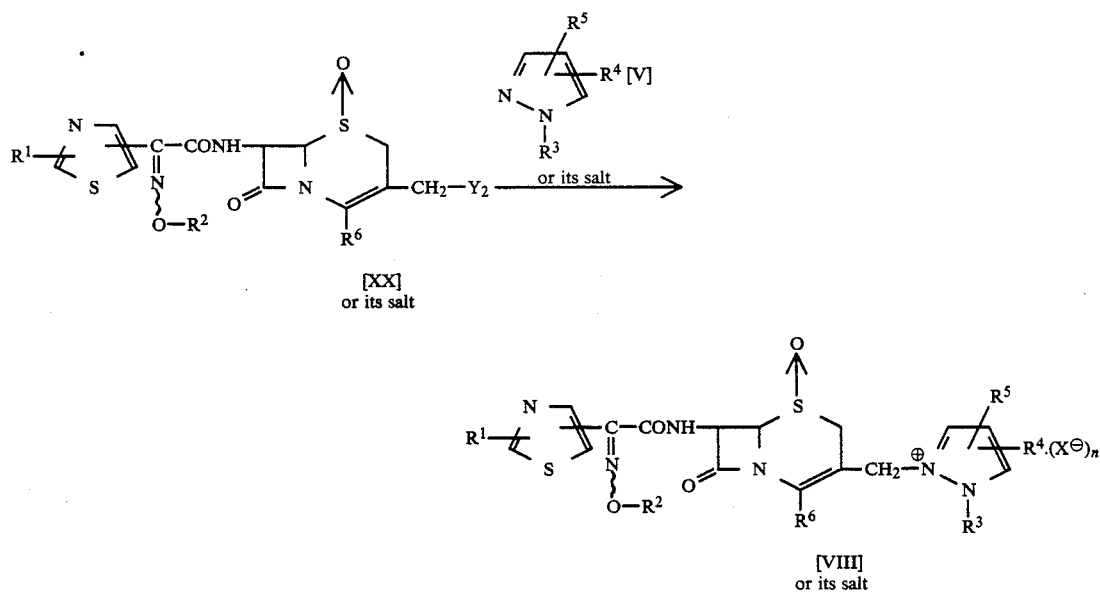

[VIII] or its salt wherein $R^1$, $R^2$, $R^3$, $R^4$, $R_a^4$, $R^5$, $R_b^5$, $R^6$, $X^{\ominus}$, Z and n are each as defined above, $R_a^2$ is hydroxy protective group, lower alkyl, dihalogenated lower alkyl, cyclo(lower)alkenyl, thietanyl, carboxy(lower)alkyl or protected carboxy(lower)alkyl, $R^7$ is protected amino, $R^8$ is carboxy or protected carboxy, $R_a^8$ is protected carboxy, and $Y_1$ and $Y_2$ are each a leaving group.

Methods A to D for the preparation of the starting compounds [IIa], [IIIa], [VI] and [VIII] are explained in detail in the following.

Method A

Step 1:

The object compound [XI] can be prepared by reacting a compound [IX] with a compound [X] or its salt.

Suitable salts of the compounds [IX] and [XI] can be referred to the ones as exemplified for the compound [I] and salt of the compound [X] can be referred to the acid addition salt for the compound [I].

This reaction can be carried out in a similar manner to that of Process 3 mentioned in the above, and therefore the reaction mode and reaction conditions [e.g. solvent, reaction temperature, etc.] of this reaction are to be referred to those as explained in Process 3.

The compound [XI] obtained by this step can be used for next step with or without isolation or purification.

Anion $X^\ominus$ may be the one derived from a leaving group $Y_1$ and may be the other one converted therefrom by a conventional method.

Step 2:

The object compound [XII] can be prepared by reducing a compound [XI].

Suitable salt of the compound [XII] can be referred to the ones as exemplified for the compound [I].

The present reduction can be carried out by a conventional method which is applied for the transformation of

into —S—, for example, by using phosphorus trichloride, a combination of stannous chloride and acetyl chloride, a combination of an alkali metal iodide [e.g. sodium iodide, etc.] and trihaloacetic anhydride [e.g. trifluoroacetic anhydride, etc.], and the like.

The present reduction is usually carried out in a solvent such as acetone, dioxane, acetonitrile, N,N-dimethylformamide, benzene, hexane, chloroform, methylene chloride, ethylene chloride, tetrahydrofuran, ethyl acetate, or any other solvent which does not adversely affect the reaction.

The reaction temperature is not critical and the reaction is usually carried out under cooling or at ambient temperature.

Step 3:

The object compound [IIa] and its salt can be prepared by subjecting a compound [XII] to elimination reaction of the amino protective group.

Suitable salts of the compounds [IIa] can be referred to the ones as exemplified for the compound [I].

This reaction can be carried out in a similar manner to that of Process 2 mentioned in the above, and therefore the reaction mode and reaction conditions [e.g. base, acid, catalyst, solvent, reaction temperature, etc.] of this reaction are to be referred to those as explained in Process 2.

The present invention includes within the scope of the invention the case that protected carboxy in $R^6$ is transformed into carboxy during this reaction.

Method B

The object compound [IIIa] and its salt can be prepared by reacting a compound [XIII] or its salt with 3-cyclopenten-1-yloxyamine or its salt.

Suitable salts of the compounds [IIIa] and [XIII] can be referred to the ones as exemplified for the compound [III].

Suitable salts of 3-cyclopenten-1-yloxyamine can be referred to the acid addition salt as exemplified for the compound [I].

The reaction is usually carried out in a conventional solvent such as water, alcohol [e.g. methanol, ethanol, etc.], dioxane, acetonitrile, tetrahydrofuran, methylene chloride, chloroform, ethyl acetate, N,N-dimethylformamide, or a mixture thereof or any other organic solvent which does not adversely influence the reaction.

The reaction temperature is not critical, and the reaction is usually carried out under cooling to warming.

This reaction can be carried out in the presence of catalytic amount of a conventional acid or base as exemplified in Process 2.

Method C

Step 1

The object compound [XV] or its salt can be prepared by reacting the compound [XIV] or its salt with aniline or its salt.

Suitable salt of aniline can be referred to acid addition salt as exemplified for the compound [I].

This reaction is usually carried out in the presence of an acid such as acetic acid, p-toluenesulfonic acid, or the like.

This reaction is usually carried out in a solvent such as benzene, toluene or any other solvent which does not adverse the reaction.

The reaction temperature is not critical and this reaction is usually carried out under warming to heating.

Step 2

The object compound [XVI] or its salt can be prepared by subjecting the compound [XV] to introduction reaction of $R_a^2$ group.

Suitable salt of the compound [XVI] can be referred to salt with a base as exemplified for the compound [I].

Suitable introduction reaction of $R_a^2$ group may include substitution reaction with a compound of the formula: $R_a^2$-$Y_3$ (wherein $R_a^2$ is as defined above and $Y_3$ is a leaving group as exemplified before), and the like.

This substitution reaction can be carried out in a similar manner to that of Process 3 mentioned in the above, and therefore the reaction mode and reaction conditions [e.g. solvent, reaction temperature, etc.] of this reaction are to be referred to those as explained in Process 3.

In case that $R_a^2$ to be introduced is lower alkyl, di(lower)alkyl sulfate (e.g. dimethyl sulfate, diethyl sulfate, etc., diazo(lower)alkane (e.g. diazomethane, etc.) trihalo(lower)alkane (e.g. difluorochloromethane, etc.) can be used for this introduction reaction. This reaction can be carried out in a conventional manner.

Step 3

The object compound [XVII] or its salt can be prepared by subjecting the compound [XVI'] or its salt to elimination reaction of the carbonyl protective group.

Suitable salt of the compounds [XVI'] and [XVII] can be referred to salt with a base as exemplified for the compound [I].

The elimination reaction of this step may be hydrolysis and this hydrolysis can be carried out in a similar manner to that of Process 2.

The present invention includes within the scope of the invention the case that protected carboxy in $R^8$ is also transformed into carboxy during this reaction.

Step 4

The object compound [XVIII] or its salt can be prepared by subjecting the compound [XVII'] or its salt to elimination reaction of carboxy protective group.

Suitable salt of the compound [XVII] can be referred to salt with a base as exemplified for the compound [I].

This reaction can be carried out in a similar manner to that of Process 2 mentioned in the above, and therefore the reaction mode and reaction conditions [e.g. base, acid, catalyst, solvent, reaction temperature, etc.] of this reaction are to be referred to those as explained in Process 2.

Sulfuryl halide [e.g. sulfuryl chloride, etc.] can be also used for this reaction. This reaction can be carried out in a conventional manner. In this case, halogenation in the next step may occur at the same time. The present invention includes this case within the scope of the invention.

Step 5

The object compound [XIX] or its salt can be prepared by subjecting the compound [XVIII] or its salt to halogenation reaction.

Suitable salt of the compound [XIX] can be referred to salt with a base as exemplified for the compound [I].

The halogenation reaction in this step may include a reaction with sulfuryl halide [e.g. sulfuryl chloride, etc.], and the like.

The reaction with sulfuryl halide is usually carried out in a solvent such as acetic acid, tetrachloromethane, methylene chloride or any other solvent which does not adverse the reaction.

The reaction temperature is not critical and the reaction is usually carried out under cooling to heating.

Step 6

The object compound [VI] or its salt can be prepared by reacting the compound [II] or its reactive derivative at the amino group or its salt with the compound [XIX] or its reactive derivative at the carboxy group or its salt.

Suitable reactive derivative at the carboxy group of the compound [XIX] can be referred to the ones as exemplified for that of the compound [III] in Process 1.

This reaction can be carried out in a similar manner to that of Process 1 mentioned in the above, and therefore the reaction mode and reaction conditions [e.g. base, acid, catalyst, solvent, reaction temperature, etc.] of this reaction are to be referred to those as explained in Process 1.

Method D

The object compound [VIII] or its salt can be prepared by reacting the compound [XX] or its salt with the compound [V] or its salt.

Suitable salts of the compounds [VIII] and [XX] can be referred to the ones as exemplified for the compound [I].

This reaction can be carried out in a similar manner to that of Process 3 mentioned in the above, and therefore the reaction mode and reaction conditions [e.g. solvent, reaction temperature, etc.] of this reaction are to be referred to those as explained in Process 3.

Anion $X^{\ominus}$ may be the one derived from a leaving group $Y_2$ and may be the other one converted therefrom by a conventional method.

The compounds [I], [Ib], [Id], [If], [Ih], [Ij], [Ik], [IIa], [IIIa], [VI], [XI], [XII], [XV], [XVI], [XVII], [XVIII], [XIX] and [VIII] obtained by the above Processes and Methods can be isolated and purified by a conventional manner such as pulverization, recrystallization, column chromatography, reprecipitation or the like.

It is to be noted the compound [I] to [VI], [VIII] to [XIII] and [XVI] to [XX], [Ia] to [In], [IIa] and [IIIa] may include one or more stereoisomers due to asymmetric carbon atoms and all of such isomers and a mixture thereof are included within the scope of this invention.

The object compounds [I] and pharmaceutically acceptable salts thereof are novel and exhibit high antimicrobial activity, inhibiting the growth of a wide variety of pathogenic microorganisms including Gram-positive and Gram-negative microorganisms and are useful as antimicrobial agents.

Among the object compounds [I], the compound having the more potent antimicrobial activities can be represented by the following formula:

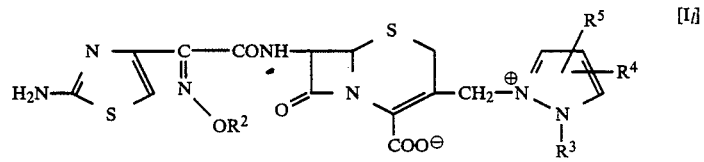

wherein
$R^2$ is hydrogen, lower alkyl, dihalogenated lower alkyl, cyclo(lower)alkenyl or thietanyl,
$R^3$ is lower alkyl,
$R^4$ and $R^5$ are each hydrogen, lower alkyl, hydroxy(lower)alkyl, lower alkoxy or amino, and a pharmaceutically acceptable salt thereof, in which the most preferred one may be represented by the following formula:

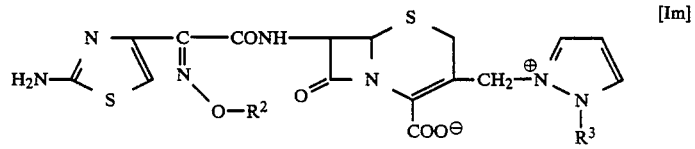

wherein
$R^2$ is dihalogenated lower alkyl, and
$R^3$ is lower alkyl, and a pharmaceutically acceptable salt thereof, or may be represented by the following formula:

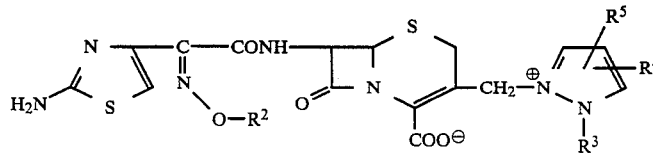

wherein
$R^2$ is lower alkyl or dihalogenated lower alkyl,
$R^3$ is lower alkyl,
$R^4$ is lower alkyl, and
$R^5$ is amino,
and a pharmaceutically acceptable salt thereof.

Now in order to show the utility of the object compounds [I], the test data on MIC (minimal inhibitory concentration) of representative compounds [I] of this invention are shown in the following.

Test method In vitro antibacterial activity was determined by the two-fold agar-plate dilution method as described below.

One loopful of an overnight culture of each test strain in Trypticase-soy broth ($10^6$ viable cells per ml) was streaked on heart infusion agar (HI-agar) containing graded concentrations of representative test compound, and the minimal inhibitory concentration (MIC) was expressed in terms of μg/ml after incubation at 37° C. for 20 hours.

Test compounds

7β-[2-(2-Aminothiazol-4-yl)-2-(difluoromethox-yimino)acetamido]-3-(2-methyl-1-pyrazolio)methyl-3-cephem-4-carboxylate (syn isomer) (hereinafter referred to as Compound A).

7β-[2-(2-Aminothiazol-4-yl)-2-(2-cyclopenten-1-ylox-yimino)acetamido]-3-(2-methyl-1-pyrazolio)methyl-3-cephem-4-carboxylate (syn isomer) (hereinafter referred to as Compound B).

7β-[2-(2-Aminothiazol-4-yl)-2-methox-yiminoacetamido]-3-(3-amino-2,4-dimethyl-1-pyrazolio)methyl-3-cephem-4-carboxylate (syn isomer) (hereinafter referred to as Compound C).

7β-[2-(2-Aminothiazol-4-yl)-2-(difluoromethox-yimino)acetamido]-3-(3-amino-2,4-dimethyl-1-pyrazplio)methyl-3-cephem-4-carboxylate (syn isomer) (hereinafter referred to as Compound D).

Test results:

| Teat strains | MIC (μg/ml) Test compounds | | | |
|---|---|---|---|---|
| | A | B | C | D |
| E. coli 31 | <0.025 | 0.05 | ≦0.025 | ≦0.025 |
| P. mirabilis 1 | 0.05 | 0.2 | 0.05 | 0.05 |
| P. vulgaris IAM1025 | 0.05 | 0.05 | ≦0.025 | ≦0.025 |

For therapeutic administration, the object compounds [I] and pharmaceutically acceptable salts thereof of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound [I] may vary from and also depend upon the age, conditions of the patient, a kind of diseases, a kind of the compound [I] to be applied, etc. In general, amounts between 1 mg and about 4,000 mg or even more per day may be administered to a patient. An average single dose of about 50 mg, 100 mg, 250 mg, 500 mg, 1000 mg, 2000 mg of the object compounds [I] of the present invention may be used in treating diseases infected by pathogenic microorganisms.

The following Preparations and Examples are given for the purpose of illustrating the present invention in more detail.

Preparation 1

A mixture of benzhydryl 78-tert-butoxycarbonylamino-3-iodomethyl-3-cephem-4-carboxylate 1-oxide (18.5 g) and N-methylpyrazole (37 ml) was stirred at ambient temperature for 15 hours. After the reaction mixture was added to diisopropyl ether (500 ml), the precipitates were collected by filtration, and washed with diisopropyl ether to give benzhydryl 7β-tert-butoxycarbonylamino-3-(2-methyl-1-pyrazolio)methyl-3-cephem-4-carboxylate 1-oxide iodide (20.3 g).

IR (Nujol): 3400, 1800, 1720, 1630, 1500 cm$^{-1}$

NMR (DMSO-$d_6$, δ): 1.45 (7H, s), 3.72, 4.05 (2H, ABq, J=18 Hz), 3.87 (3H, s), 5.10 (1H, d, J=5 Hz), 5.32, 5.55 (2H, ABq, J=14 Hz), 5.90 (1H, dd, J=5 Hz, 8 Hz), 6.52 (1H, d, J=8 Hz), 6.90 (1H, t, J=3 Hz), 7.00 (1H, s) 7.42 (10H, m), 8.33 (1H, d, J=3 Hz), 8.53 (1H, d, J=3 Hz)

Preparation 2

Benzhydryl 7β-tert-butoxycarbonylamino-3-(2,5-dimethyl-1-pyrazolio)methyl-3-cephem-4-carboxylate 1-oxide iodide was obtained according to a similar manner to that of Preparation 1.

IR (Nujol): 1795, 1715, 1630 cm$^{-1}$

NMR (DMSO-$d_6$, δ): 1.43 (9H, s), 2.41 (3H, s), 3.58, 3.97 (2H, ABq, J=18 Hz), 3.69 (3H, s), 5.06 (1H, d, J=5 Hz), 5.38 (2H, br. s), 5.86 (1H, dd, J=8 Hz, 5 Hz), 6.47 (1H, d, J=8 Hz), 6.71 (1H, d, J=3 Hz), 6.93 (1H, s), 7.15-7.60 (10H, m), 8.15 (1H, d, J=3 Hz)

Preparation 3

To a solution of benzhydryl 7β-tert-butoxycarbonylamino-3-(2-methyl-1-pyrazolio)methyl-3-cephem-4-carboxylate 1-oxide iodide (20 g) and N,N-dimethylformamide (100 ml) was stirred at −35° C. Phosphorus trichloride (7.8 g) was added thereto and stirred for 10 minutes at the same temperature. The reaction mixture was added to water (600 ml). The precipitates were collected by filtration and washed with water to give benzhydryl 7β-tertbutoxycarbonylamino-3-(2-methyl-1-pyrazolio)methyl-3-cephem-4-carboxylate iodide (15.4 g).

IR (Nujol): 3300, 1780, 1710, 1500 cm$^{-1}$

NMR (DMSO-d$_6$, δ): 1.48 (9H, s), 3.60 (2H, br. s), 3.87 (3H, s), 5.20 (1H, d, J=5 Hz), 5.53 (2H, br. s), 5.63 (1H, dd, J=5 Hz, 8 Hz), 6.87 (1H, t, J=3 Hz), 6.97 (1H, s), 7.43 (10H, m), 7.92 (1H, d, J=8 Hz), 8.45 (1H, d, J=3 Hz), 8.55 (1H, d, J=3 Hz)

Preparation 4

Benzhydryl 7β-tert-butoxycarbonylamino-3-(2,5-dimethyl-1-pyrazolio)methyl-3-cephem-4-carboxylate iodide was obtained according to a similar manner to that of Preparation 3.

IR (Nujol): 3300, 1780, 1710, 1610 cm$^{-1}$

NMR (DMSO-d$_6$, δ): 1.44 (9H, s), 2.44 (3H, s), 3.43 (2H, br. s), 3.71 (3H, s), 5.18 (1H, d, J=5 Hz), 5.48 (2H, br. s), 5.63 (1H, dd, J=8 Hz, 5 Hz), 6.74 (1H, d, J=3 Hz), 6.94 (1H, s), 7.10–7.60 (10H, m), 7.97 (1H, d, J=8 Hz), 8.30 (1H, d, J=3 Hz)

Preparation 5

To a solution of benzhydryl 7β-tert-butoxycarbonylamino-3-(2-methyl-1-pyrazolio)methyl-3-cephem-4-carboxylate iodide (22.3 g) and anisole (22 ml) in methylene chloride (66 ml) was added trifluoroacetic acid (44 ml) under ice-cooling. After the mixture was stirred at ambient temperature for an hour, the reaction mixture was added dropwise to diisopropyl ether (600 ml). The resultant precipitates were collected by filtration to give bis(trifluoroacetic acid) salts of 7β-amino-3-(2-methyl-1-pyrazolio)methyl-3-cephem-4-carboxylate (16.83 g).

IR (Nujol): 1770 cm$^{-1}$

NMR (DMSO-d$_6$, δ): 3.50 (2H, br. s), 4.11 (3H, s), 5.26 (2H, s), 5.60 (2H, br.s), 6.94 (1H, t, J=3 Hz), 8.48 (1H, d, J=3 Hz), 8.62 (1H, d, J=3 Hz)

Preparation 6

Bis(trifluoroacetic acid) salts of 7β-amino-3-(2,5-dimethyl-1-pyrazolio)methyl-3-cephem-4-carboxylate was obtained according to a similar manner to that of Preparation 5.

IR (Nujol): 1775, 1670, 1620 cm$^{-1}$

NMR (DMSO-d$_6$, δ): 2.49 (3H, s), 3.49 (2H, br. s), 3.92 (3H, s), 5.28 (2H, br. s), 5.58 (2H, br. s), 6.79 (1H, d, J=3 Hz), 8.38 (1H, d, J=3 Hz)

Preparation 7

To a solution of sodium iodide (1.46 g) in acetone (5 ml) was added benzhydryl 7β-tert-butoxycarbonylamino-3-chloromethyl-3-cephem-4-carboxylate (5 g) at ambient temperature. The mixture was stirred at the same temperature for 10 minutes and N-methylpyrazole (5 ml) was added thereto. The resultant mixture was stirred at the same temperature for 24 hours and poured into a mixture of tetrahydrofuran (25 ml), ethyl acetate (25 ml) and water (25 ml). The separated organic layer was washed with brine, and dried over magnesium sulfate. The solution was evaporated in vacuo to give benzhydryl 7β-tert-butoxycarbonylamino-3-(2-methyl-1-pyrazolio)methyl-3-cephem-4-carboxylate iodide (6.45 g), the physical data of which were identical to those of the compound prepared in Preparation 3.

Preparation 8

Benzhydryl 7β-(2-hydroxybenzylideneamino)-3-(2-methyl-1-pyrazolio)methyl-3-cephem-4-carboxylate iodide was obtained according to a similar manner to that of Preparation 7.

IR (Nujol): 1780, 1720, 1620 cm$^{-1}$

NMR (DMSO-d$_6$, δ): 3.45 (2H, br. s), 3.88 (3H, s), 5.12 (1H, d, J=5 Hz), 5.40 (2H, br. s), 5.85 (1H, d, J=5 Hz), 6.83 (1H, t, J=3 Hz), 6.94 (1H, s), 7.12–7.66 (14H, m), 8.37 (1H, d, J=3 Hz), 8.43 (1H, d, J=3 Hz), 8.81 (1H, s)

Preparation 9

To a solution of benzhydryl 7β-(2-hydroxybenzylideneamino)-3-(2-methyl-1-pyrazolio)methyl-3-cephem-4-carboxylate iodide (1 g) in tetrahydrofuran (20 ml) and ethanol (3 ml) was added conc. hydrochloric acid (0.14 ml) at ambient temperature. After stirring at the same temperature for 1 hour, the mixture was poured into tetrahydrofuran (20 ml). The resulting precipitates were collected by filtration to give hydrochloric acid salt of benzhydryl 7β-amino-3-(2-methyl-1-pyrazolio)methyl-3-cephem-4-carboxylate iodide (0.65 g).

IR (Nujol): 1785, 1720 cm$^{-1}$

NMR (DMSO-d$_6$, δ): 3.47 and 3.83 (2H, ABq, J=18 Hz), 3.91 (3H, s), 5.31 (1H, d, J=5 Hz), 5.39 (1H, d, J=5 Hz), 5.66 (2H, br. s), 6.87 (1H, t, J=3 Hz), 6.96 (1H, s), 7.10–7.57 (10H, m), 8.65 (2H, d, J=3 Hz)

Preparation 10

A mixture of benzhydryl 7β-[2-(2-cyclopenten-1-yloxyimino)-2-(2-formamidothiazol-4-yl)acetamido]-3-iodomethyl-3-cephem-4-carboxylate 1-oxide (syn isomer, 7 g) and N-methylpyrazole (17.5 ml) was stirred at ambient temperature for 4.5 hours. The reaction mixture was poured into ethyl acetate (500 ml). Precipitates were collected by filtration, washed with ethyl acetate and diisopropyl ether to give benzhydryl 7β-[2-(2-cyclopenten-1-yloxyimino)-2-(2-formamidothiazol-4-yl)acetamido]-3-(2-methyl-1-pyrazolio)methyl-3-cephem-4-carboxylate 1-oxide iodide (syn isomer, 5.4 g).

IR (Nujol): 3300, 1800, 1720, 1670, 1540 cm$^{-1}$

NMR (DMSO-d$_6$, δ): 2.15 (2H, m), 2.33 (2H, m), 3.53, 3.80 (2H, ABq, J=18 Hz), 3.87 (3H, s), 5.15 (1H, d, J=5 Hz), 5.40 (3H, m), 6.10 (2H, m,), 6.90 (1H, t, J=2 Hz), 7.00 (1H, s), 7.10–7.60 (10H, m), 7.48 (1H, s), 8.35 (1H, d, J=2 Hz), 8.54 (1H, s), 8.54 (1H, m), 9.15 (1H, d, J=8 Hz)

Preparation 11

To a solution of 3-cyclopenten-1-ol (15.3 g), N-hydroxyphthalimide (29.7 g) and triphenylphosphine (47.7 g) in tetrahydrofuran (250 ml) was added diethyl azodicarboxylate (31.7 g) at 40° to 50° C. After stirring at 45° C. for 2 hours, the reaction mixture was poured into ice-water and extracted with ethyl acetate. The separated organic layer was washed with 5% aqueous solution of sodium bicarbonate, brine, successively and dried over magnesium sulfate. The solvent was evaporated in vacuo, and the residual oil was subjected to column chromatography on silica gel. The desired product was eluted with 15% ethyl acetate in n-hexane to give N-(3-cyclopenten-1-yloxy)phthalimide (25.6 g).

IR (Nujol): 1790, 1730 cm$^{-1}$

NMR (CDCl$_3$, δ): 2.6–2.9 (4H, m), 5.30 (1H, m), 5.80 (2H, s), 7.85 (4H, m)

Preparation 12

A mixture of N-(3-cyclopenten-1-yloxy)phthalimide (5.0 g) and hydrazine hydrate (1.32 g), methanol (10 ml) and methylene chloride (50 ml) was stirred at ambient temperature for 30 minutes. The precipitates were filtered off, and the filtrate was washed with water. The separated organic layer was concentrated under reduced pressure. To the residue were added 2-(2-formamidothiazol-4-yl)glyoxylic acid (3.50 g), pyridine (3.5 ml), water (35 ml) and tetrahydrofuran (15 ml). After stirring at ambient temperature for 1 hour, the mixture was poured into water (100 ml) and adjusted to pH 8.0 with 5% aqueous solution of sodium bicarbonate. The aqueous layer was washed with ethyl acetate twice, acidified to pH 2.0 with 10% hydrochloric acid and extracted with ethyl acetate. The separated organic layer was washed with water, dried over magnesium sulfate and concentrated under reduced pressure to give 2-(3-cyclopenten-1-yloxyimino)-2-(2-formamidothiazol-4-yl)acetic acid (syn isomer, 4.65 g).

mp: 160°–161° C.

IR (Nujol): 3200, 1710, 1545 cm$^{-1}$

NMR (DMSO-d$_6$, δ): 2.4–2.8 (4H, m), 5.0 (1H, m), 5.77 (2H, s), 7.54 (1H, s), 8.57 (1H, s), 12.5 (br. s)

Preparation 13

A mixture of 2-(2-tritylaminothiazol-4-yl)-2-difluoromethoxyiminoacetic acid (syn isomer) (2.4 g) and diisopropylethylamine (1.29 g) in N,N-dimethylformamide (35 ml) was cooled to −30° C. and mesyl chloride (1.15 g) was added dropwise thereto. The mixture was stirred at −20° to −30° C. for 30 minutes to give an activated acid solution. On the other hand, a mixture of benzhydryl 7β-amino-3-chloromethyl-3-cephem-4-carboxylate (2.18 g) and N-trimethylsilylacetamide (5.25 g) in methylene chloride (20 ml) was stirred to be a clear solution for 30 minutes at room temperature and then cooled to −20° C. To this solution was added the activated acid solution obtained above in one portion. The mixture was stirred for 30 minutes at −15° to −10° C., poured into water and extracted with ethyl acetate. The extract was washed with water three times, dried over magnesium sulfate and evaporated under reduced pressure. The residue was triturated in diisopropyl ether to give benzhydryl 7β-[2-(2-tritylaminothiazol-4-yl)-2-difluoromethoxyiminoacetamido]-3-chloromethyl-3-cephem-4-carboxylate (syn isomer) (4.64 g).

IR (Nujol): 1780, 1720, 1670, 1590, 1520 cm$^{-1}$

Preparation 14

A mixture of acetic anhydride (38.86 ml) and formic acid (15.54 ml) was stirred at 45° C. for 45 minutes. To this mixture was added 5-amino-1-methylpyrazole (10 g) under ice-cooling, and the reaction mixture was stirred at the same temperature for 10 minutes. The resultant mixture was poured into a mixture of water and ethyl acetate, and the resultant solution was adjusted to pH 8 with potassium carbonate. The organic layer was separated, and the aqueous layer was extracted with ethyl acetate six times. The organic layers were combined, dried over magnesium sulfate, and evaporated in vacuo to give 5-formamido-1-methylpyrazole (12.88 g).

mp: 71°–73° C.

IR (Nujol): 3300, 3200, 1705, 1590 cm$^{-1}$

NMR (CDCl$_3$, δ): 3.69 and 3.74 (3H, each s), 6.04 and 6.23 (1H, each d, J=3 Hz), 7.34 (1H, s), 8.21 (1H, s)

Preparation 15

The following compounds were obtained according to a similar manner to that of Preparation 14.

(1) 4-Formamido-1-methylpyrazole mp: 44°–45° C.

IR (Nujol): 3250, 1665, 1585 cm$^{-1}$

NMR (CDCl$_3$, δ): 3.83 (3H, s), 7.33 (1H, s), 7.83 (1H, s), 8.17 (1H, s)

(2) 5-Formamido-1,4-dimethylpyrazole

IR (Nujol): 3200, 1665, 1585 cm$^{-1}$

NMR (CDCl$_3$, δ): 1.90 and 1.98 (3H, each s), 3.64 and 3.72 (3H, each s), 7.29 and 7.31 (1H, each s), 8.10 (1H, broad s), 8.33 and 9.03 (1H, each s)

Preparation 16

To a mixture of benzhydryl 7β-tert-butoxycarbonylamino-3-chloromethyl-3-cephem-4-carboxylate (15 g) and sodium iodide (4.37 g) in acetone (15 ml) was added 5-formamido 1-methylpyrazole (15 g) at ambient temperature. After being stirred for 40 hours at the same temperature, the mixture was poured into a mixture of water and ethyl acetate. The organic layer was separated and washed with water, aqueous sodium chloride solution, and dried over magnesium sulfate.

The solution was evaporated in vacuo to give benzhydryl 7β-tert-butoxycarbonylamino-3-(3-formamido-2-methyl-1-pyrazolio)methyl-3-cephem-4-carboxylate iodide (20.95 g).

IR (Nujol): 1780, 1710, 1580 cm$^{-1}$

NMR (DMSO-d$_6$, δ): 1.40 (9H, s), 3.41 (2H, broad s), 3.65 (3H, s), 5.12 (1H, d, J=5 Hz), 5.36 (2H, broad s), 5.57 (1H, dd, J=8 Hz and 5 Hz), 6.88 (1H, s), 6.89 (1H, m), 7.10–7.48 (10H, m), 7.83 (1H, d, J=8 Hz), 8.24 (1H, d, J=3 Hz), 8.45 (1H, s)

Preparation 17

The following compounds were obtained according to a similar manner to that of Preparation 16.

(1) Benzhydryl 7β-tert-butoxycarbonylamino-3-(4-formamido-2-methyl-1-pyrazolio)methyl-3-cephem-4-carboxylate iodide IR (Nujol): 1785, 1720, 1605 cm$^{-1}$ NMR (DMSO-d$_6$, δ): 1.39 (9H, s), 3.42 (2H, broad s), 3.77 (3H, s), 5.11 (1H, d, J=5 Hz), 5.41 (2H, broad s), 5.60 (1H, dd, J=8 Hz and 5 Hz), 6.89 (1H, s), 7.18–7.52 (10H, m), 7.96 (1H, d, J=8 Hz), 8.25 (1H, s), 8.51 (1H, s), 8.57 (1H, s)

(2) Benzhydryl 7β-tert-butoxycarbonylamino-3-(3-formamido-2,4-dimethyl-1-pyrazolio)methyl-3-cephem-4-carboxylate iodide.

IR (Nujol): 3300, 1780, 1705 cm$^{-1}$

NMR (DMSO-d$_6$, δ): 1.42 (9H, s), 1.98 (3H, s), 3.45 (2H, broad s), 3.63 (3H, s), 5.19 (1H, d, J=5 Hz), 5.40 (2H, broad s), 5.61 (1H, dd, J=5 Hz and 8 Hz), 6.95 (1H, s), 7.21–7.58 (10H, m), 8.00 (1H, d, J=8 Hz), 8.21 (1H, s), 8.43 (1H, s)

Preparation 18

To a solution of benzhydryl 7β-tert-butoxycarbonylamino-3-(3-formamido-2-methyl-1-pyrazolio)-methyl-3-cephem-4-carboxylate iodide (20.9 g) and anisole (20 ml) in methylene chloride (40 ml) was added dropwise trifluoroacetic acid (40 ml) under ice-cooling. After being stirred for 1.5 hours at ambient temperature, the mixture was poured into a mixture of diisopropyl ether (300 ml) and ethyl acetate (300 ml). The resultant precipitate was collected by filtration to give bis(trifluoroacetic acid) salts of 7β-amino-3-(3-formamido-2-methyl-1-pyrazolio)methyl-3-cephem-4-carboxylate (16.20 g).

IR (Nujol): 3350, 1770, 1660 cm$^{-1}$

NMR (DMSO-d$_6$, δ): 3.45 (2H, s), 3.87 (3H, s), 5.18 (2H, s), 5.47 (2H, s), 6.95 (1H, d, J=3 Hz), 8.33 (1H, d, J=3 Hz), 8.47 (1H, s)

Preparation 19

The following compounds were obtained according to a similar manner to that of Preparation 18.

(1) Bis(trifluoroacetic acid)salts of 7β-amino-3-(4-formamido-2-methyl-1-pyrazolio)methyl-3-cephem-4-carboxylate.

IR (Nujol): 3400, 1780, 1660, 1605 cm$^{-1}$

NMR (DMSO-d$_6$, δ): 3.51 (2H, broad s), 4.06 (3H, s), 5.23 (2H, s), 5.55 (2H, broad s), 8.30 (1H, s), 8.61 (1H, s), 8.67 (1H, s).

(2) Bis(trifluoroacetic acid)salts of 7β-amino-3-(3-formamido-2,4-dimethyl-1-pyrazolio)methyl-3-cephem-4-carboxylate.

NMR (DMSO-d$_6$, δ): 2.01 (3H, s), 3.48 (2H, broad s), 3.83 (3H, s), 5.24 (2H, s), 5.50 (2H, broad s), 8.26 (1H, s), 8.41 (1H, s)

Preparation 20

Conc. hydrochloric acid (4.09 g) was added to a solution of benzhydryl 7β-tert-butoxycarbonylamino-3-(2-methyl-1-pyrazolio)methyl-3-cephem-4-carboxylate iodide (27 g) in formic acid (108 ml), and stirred at ambient temperature for 2.5 hours. The reaction mixture was added to a mixture of acetone (720 ml) and ethyl acetate (1440 ml). The precipitates were collected by filtration and successively washed with ethyl acetate to give 7β-amino-3-(2-methyl-1-pyrazolio)methyl-3-cephem-4-carboxylate hydrochloride hydroiodide (15.3 g).

IR (Nujol): 3350, 3100, 1780, 1710, 1620 cm$^{-1}$

NMR (D$_2$O-NaHCO$_3$, δ): 3.42 and 3.56 (2H, ABq, J=18 Hz), 4.10 (3H, s), 5.02 (1H, d, J=5 Hz), 5.22 (1H, d, J=5 Hz), 5.27 and 5.52 (2H, ABq, J=14 Hz), 6.80 (1H, t, J=3 Hz), 8.23 (2H, d, J=3 Hz)

Preparation 21

A mixture of 7β-amino-3-(2-methyl-1-pyrazolio)-methyl-3-cephem-4-carboxylate hydrochloride hydroiodide (10 g) in water (70 ml) and acetone (130 ml) was stirred at 0°-5° C. for 1.5 hours. The precipitates crystallized out of the solution were collected by filtration, washed with a mixture of acetone (24 ml) and water (6 ml) and then acetone to give 7β-amino-3-(2-methyl-1-pyrazolio)methyl-3-cephem-4-carboxylate hydrochloride.tetrahydrate (6.6 g).

IR (Nujol): 3350, 3100, 1800, 1780 (s), 1600, 1510 cm$^{-1}$

NMR (D$_2$O, δ): 3.33 and 3.60 (2H, ABq, J=18 Hz), 4.11 (3H, s), 5.18 (1H, d, J=5 Hz), 5.32 (1H, d, J=5 Hz), 5.32 and 5.53 (2H, ABq, J=14 Hz), 6.80 (1H, t, J=3 Hz), 8.23 (2H, d, J=3 Hz)

Preparation 22

Concentrated hydrochloric acid (0.353 ml) was added to a mixture of bis(trifluoroacetic acid) salt of 7β-amino-3-(3-formamido-2-methyl-1-pyrazolio)methyl-3-cephem-4-carboxylate (0.565 g) in tetrahydrofuran (3 ml) and methanol (3 ml) at ambient temperature. After being stirred at the same temperature for 12 hours, the mixture was added dropwise to ethyl acetate (100 ml). The resulting precipitate was collected by filtration to give 7β-amino-3-(3-amino-2-methyl-1-pyrazolio)methyl-3-cephem-4-carboxylate trihydrochloride (292 mg).

NMR (DMSO-d$_6$, δ): 3.31 and 3.56 (2H, ABq, J=18 Hz), 3.67 (3H, s), 5.20 (2H, broad s), 5.29 (2H, broad s), 5.87 (1H, d, J=3 Hz), 8.12 (1H, d, J=3 Hz)

Preparation 23

A solution of tert-butyl 2-hydroxyimino-3-oxobutyrate (130 g), aniline (76 ml) and acetic acid (14 ml) in benzene (1.2 l) was refluxed with Dean Stark water separator for 5 hours. The resulting solution was cooled and washed with 5% aqueous sodium bicarbonate solution and water. After being dried over magnesium sulfate, the organic solvent was evaporated in vacuo. The residue was triturated with a mixture of n-hexane (300 ml) and diisopropyl ether (100 ml). The precipitate was collected by filtration, washed with n-hexane to give tert-butyl 2-hydroxyimino-3-phenyliminobutyrate (71.2 g).

IR (Nujol): 3380, 1722, 1625 cm$^{-1}$

NMR (CDCl$_3$, δ): 1.50 (9H, s), 2.12 (3H, s), 6.5-7.3 (5H, m)

Preparation 24

Ethyl 2-hydroxyimino-3-phenyliminobutyrate was prepared according to a similar manner to that of Preparation 23.

IR (film): 3550, 1735, 1639, 1598 cm$^{-1}$

Preparation 25

Into a solution of tert-butyl 2-hydroxyimino-3-phenyliminobutyrate (2.0 g) in a mixture of 1,4-dioxane (50 ml) and ethanol (10 ml) was bubbled difluorochloromethane under ice-cooling with stirring until the solution was saturated with the gas. To the mixture was added dropwise 4N sodium hydroxide solution (19 ml) at 15° C. with gentle bubbling of difluorochloromethane. After the addition, the mixture was stirred under the same condition for 2 hours. The resulting mixture was neutralized to pH 7.0 with 6N hydrochloric acid and extracted with ethyl acetate. The separated organic layer was washed with 5% aqueous sodium chloride solution three times, dried over magnesium sulfate and concentrated under reduced pressure to give an oil (2.03 g). The residual oil was subjected to column chromatography on silica gel (20 g) and eluted with a mixture of n-hexane and diethyl ether (15:1) to give tert-butyl 2-difluoromethoxyimino-3-phenyliminobutyrate (0.80 g).

IR (Film): 1740, 1639, 1598 cm$^{-1}$

NMR (CDCl$_3$, δ): 1.50 (9H, s), 2.10 (3H, s), 6.60 (1H, t, J=72 Hz), 6.7-7.3 (5H, m)

Preparation 26

Ethyl 2-difluoromethoxyimino-3-phenyliminobutyrate was prepared according to a similar manner to that of Preparation 25.

IR (Nujol): 1755, 1640, 1598 cm$^{-1}$

NMR (CDCl$_3$, δ): 1.35 (3H, t, J=7 Hz), 2.08 (3H, s), 4.33 (2H, q, J=7 Hz), 6.62 (1H, t, J=72 Hz), 6.6-7.5 (5H, m)

Preparation 27

(1) To a solution of tert-butyl 2-difluoromethoxyimino-3-phenyliminobutyrate (0.76 g) in tetrahydrofuran (3.8 ml) was added 1N hydrochloric acid (3.64 ml)

under ice-cooling. After being stirred at 20° C. for 1.5 hours, the mixture was extracted with ethyl acetate. The separated organic layer was washed with water three times, dried over magnesium sulfate and concentrated under reduced pressure to give tert-butyl 2-difluoromethoxyimino-3-oxobutyrate (0.55 g).

IR (film): 1750, 1715 cm$^{-1}$

NMR (CDCl$_3$, δ): 1.40 (9H, s), 2.39 (3H, s), 6.57 (1H, t, J=72 Hz)

(2) To a solution of tert-butyl 2-difluoromethoxyimino-3-oxobutyrate (5.0 g) in acetic acid (5 ml) was added sulfuryl chloride (8.5 ml). The mixture was stirred at 60°-63° C. for 7 hours. The solvent was evaporated in vacuo to give 4-chloro-2-difluoromethoxyimino-3-oxobutyric acid (4.5 g) as a glassy mass.

IR (film): 1710-1750 (broad) cm$^{-1}$

NMR (CDCl$_3$, δ): 4.63 (2H, s), 6.73 (1H, t, J=72 Hz)

Preparation 28

Ethyl 2-difluoromethoxyimino-3-oxobutyrate was prepared according to a similar manner to that of Preparation 27 (1).

IR (film) 1755, 1715 cm$^{-1}$

NMR (CDCl$_3$, δ): 1.38 (3H, t, J=7 Hz), 2.43 (3H, s), 4.36 (2H, q, J=7 Hz), 6.65 (1H, t, J=72 Hz)

Preparation 29

To a solution of tert-butyl 2-difluoromethoxyimino-3-oxobutyrate (9.4 g) in acetic acid (9.4 ml) was added sulfuryl chloride (2.55 ml) under ice-cooling. After stirred at ambient temperature for an hour, the reaction mixture was concentrated under reduced pressure. The residual oil was dissolved in ethyl acetate. The ethyl acetate solution was washed with water, dried over magnesium sulfate, and evaporated in vacuo. The residue was crystallized with diisopropyl ether to give (Z)-2-difluoromethoxyimino-3-oxobutyric acid (4.73 g).

mp: 118°-120° C.

IR (Nujol): 2660, 1730, 1710 cm$^{-1}$

NMR (CDCl$_3$+DMSO-d$_6$, δ): 2.45 (3H, s), 6.42 (1H, t, J=70.4 Hz)

Preparation 30

To a solution of tert-butyl 2-hydroxyimino-3-phenyliminobutyrate (1.0 g) in acetone (10 ml) was added potassium carbonate (0.63 g) and dimethyl sulfate (0.43 ml) under ice-cooling. The mixture was stirred at the same temperature for 30 minutes and stirred at ambient temperature for 4 hours. The resulting suspension was poured into ice-water and extracted with diisopropyl ether. The organic layer was washed with water, dried over magnesium sulfate, and evaporated in vacuo. The residual oil was subjected to column chromatography on silica gel to give tert-butyl 2-methoxyimino-3-phenyliminobutyrate (0.68 g).

IR (film): 1735, 1632, 1592 cm$^{-1}$

NMR (CDCl$_3$, δ): 1.54 (9H, s), 2.00 (3H, s), 4.01 (3H, s), 6.7-6.9 (2H, m), 7.0-7.5 (3H, m)

EXAMPLE 1

Vilsmeier reagent was prepared from N,N-dimethylformamide (0.36 ml) and phosphoryl chloride (0.42 ml) in a usual manner. Vilsmeier reagent was suspended in ethyl acetate (7.5 ml), and 2-(2-formamidothiazol-4-yl)-2-methoxyiminoacetic acid (syn isomer, 0.88 g) was added thereto under ice-cooling. The mixture was stirred at the same temperature for 30 minutes to produce an activated acid solution. A solution of bis(trifluoroacetic acid) salts of 7β-amino-3-(2-methyl-1-pyrazolio)methyl-3-cephem-4-carboxylate (2 g) and N,O-bis(trimethylsilyl)acetamide (3.79 ml) in tetrahydrofuran (20 ml) was added to the above activated acid solution at −30° C., and the reaction mixture was stirred at −20° to −10° C. for 30 minutes. The mixture was added dropwise to diethyl ether (300 ml), and the precipitates were collected by filtration to give trifluoroacetic acid salt of 7β-[2-(2-formamidothiazol-4-yl)-2-methoxyiminoacetamido]-3-(2-methyl-1-pyrazolio)-methyl-3-cephem-4-carboxylate (syn isomer, 2.25 g).

IR (Nujol): 1785, 1675 cm$^{-1}$

NMR (DMSO-d$_6$, δ): 3.42 (2H, br. s), 3.89 (3H, s), 4.10 (3H, s), 5.23 (1H, d, J=5 Hz), 5.56 (2H, br. s), 5.89 (1H, dd, J=8, 5 Hz) 6.93 (1H, t, J=3 Hz), 7.41 (1H, s), 8.49 (1H, d, J=3 Hz), 8.52 (1H, s), 8.60 (1H, d, J=3 Hz), 9.70 (1H, d, J=8 Hz)

EXAMPLE 2

Methanesulfonyl chloride (0.61 ml) was added to a solution of 2-(2-aminothiazol-4-yl)-2-(3-thietanyloxyimino)acetic acid (syn isomer, 0.99 g) and N,N-diisopropyl-N-ethylamine (1.33 ml) in N,N-dimethylformamide (20 ml) at −55° to −50° C., and the mixture was stirred for 10 minutes to produce an activated acid solution. To a solution of bis(trifluoroacetic acid) salts of 7β-amino-3-(2-methyl-1-pyrazolio)methyl-3-cephem-4-carboxylate (2 g) and N,O-bis(trimethylsilyl)acetamide (3.79 ml) in tetrahydrofuran (20 ml) was added the above activated acid solution under ice-cooling, and the reaction mixture was stirred at the same temperature for an hour. The resultant mixture was poured into diethyl ether, and the precipitates were collected by filtration. The precipitates were suspended in water (20 ml), and the suspension was adjusted to pH 5 with 5% aqueous solution of sodium bicarbonate and subjected to column chromatography on macroporous non-ionic adsorption resin "Diaion HP-20" (Trademark, manufactured by Mitsubishi Chemical Industries) and eluted with 10% aqueous solution of isopropyl alcohol. The fractions containing the object compound were collected, evaporated in vacuo to remove isopropyl alcohol, and lyophilized to give 7β-[2-(2-aminothiazol-4-yl)-2-(3-thietanyloxyimino)acetamido]-3-(2-methyl-1-pyrazolio)methyl-3-cephem-4-carboxylate (syn isomer, 0.5 g).

IR (Nujol): 1770, 1660, 1605 cm$^{-1}$

NMR (D$_2$O, δ): 3.2-3.8 (4H, m), 3.22, 3.63 (2H, ABq, J=18 Hz), 4.13 (3H, s), 5.10-5.32 (1H, m), 5.20, 5.54 (2H, ABq, J=15 Hz), 5.34 (1H, d, J=5 Hz), 5.89 (1H, d, J=5 Hz), 6.76-6.83 (1H, m), 7.03 (1H, s), 8.16-8.23 (2H, m)

The following compounds (Examples 3 to 18) were obtained according to similar manners to those of Examples 1 and 2.

EXAMPLE 3

Trifluoroacetic acid salt of 7β-[2-(2-formamidothiazol-4-yl)-2-isopropoxyiminoacetamido]- 3-(2-methyl-1-pyrazolio)methyl-3-cephem-4-carboxylate (syn isomer)

IR (Nujol): 3400, 1770, 1650 cm$^{-1}$

NMR (DMSO-d$_6$, δ): 1.28 (6H, d, J=6 Hz), 3.28, 3.63 (2H, ABq, J=18 Hz), 3.50 (1H, m), 4.13 (3H, s), 5.17 (1H, d, J=5 Hz), 5.45, 5.72 (2H, ABq, J=15 Hz), 5.78 (1H, dd, J=5 Hz, 8 Hz), 6.93 (1H, t, J=3 Hz), 7.40 (1H, s), 8.53 (2H, m), 9.62 (1H, d, J=8 Hz)

EXAMPLE 4

Trifluoroacetic acid salt of 7β-[2-(2-cyclopenten-1-yloxyimino)-2-(2-formamidothiazol-4-yl)acetamido]-3-(2,5-dimethyl-1-pyrazolio)methyl-3-cephem-4-carboxylate (syn isomer)

IR (Nujol): 3350, 1770, 1670 cm$^{-1}$

NMR (DMSO-d$_6$, δ): 1.80–2.40 (4H, m), 2.48 (3H, s), 3.37 (2H, br. s), 3.90 (3H, s), 5.18 (1H, d, J=5 Hz), 5.30 (1H, m), 5.50 (2H, br. s), 5.80–6.22 (2H, m), 5.82 (1H, dd, J=8 Hz, 5 Hz), 6.77 (1H, d, J=3 Hz), 7.35 (1H, s),8.32 (1H, d, J=3 Hz), 8.48 (1H, s), 9.60 (1H, d, J=8 Hz)

EXAMPLE 5

Trifluoroacetic acid salt of 7β-[2-(2-tetrahydropyranyloxyimino)-2-(2-tritylaminothiazol-4-yl)acetamido]-3-(2-methyl-1-pyrazolio)methyl-3-cephem-4-carboxylate (syn isomer)

IR (Nujol): 3300, 3150, 1775, 1675 cm$^{-1}$

NMR (DMSO-d$_6$, δ): 1.50–1.93 (6H, m), 3.40 (2H, br. s), 3.50 (2H, m), 4.08 (3H, s), 5.20 (1H, d, J=5 Hz), 5.25 (1H, m), 5.53 (2H, br. s), 5.78 (1H, dd, J=8 Hz, 5 Hz), 6.75 (1H, d, J=2 Hz), 7.15–7.60 (16H, m), 8.43 (1H, d, J=2 Hz), 8.56 (1H, d, J=2 Hz), 9.60 (1H, d, J=8 Hz)

EXAMPLE 6

Trifluoroacetic acid salt of 7,8-[2-difluoromethoxyimino-2-(2-tritylaminothiazol-4-yl)acetamido]-3-(2,5-dimethyl-1-pyrazolio)methyl-3-cephem-4-carboxylate (syn isomer)

IR (Nujol): 1780, 1660 cm$^{-1}$

NMR (DMSO-d$_6$, δ): 2.43 (3H, s), 3.30–3.61 (2H, m), 3.84 (3H, s), 5.13 (2H, d, J=5 Hz), 5.47 (2H, br. s), 5.70 (1H, dd, J=5 Hz, 8 Hz), 6.60–7.35 (18H, m), 8.27 (1H, s), 9.60 (1H, d, J=8 Hz)

EXAMPLE 7

7β-[2-(2-Aminothiazol-4-yl)-2-(difluoromethoxyimino)acetamido]-3-(2-methyl-1-pyrazolio)methyl-3-cephem-4-carboxylate (syn isomer)

IR (Nujol): 3400, 1770, 1660, 1600, 1530 cm$^{-1}$

NMR (D$_2$O, δ): 3.20, 3.50 (2H, ABq, J=18 Hz), 4.10 (3H, s), 5.25 (1H, d, J=5 Hz), 5.25, 5.50 (2H, ABq, J=14 Hz), 5.85 (1H, d, J=5 Hz) 6.75 (1H, t, J=72 Hz), 7.20 (1H, s), 8.17 (2H, m)

EXAMPLE 8

7β-[2-(2-Aminothiazol-4-yl)-2-(2-cyclopenten-1-yloxyimino)acetamido]-3-(2-methyl-1-pyrazolio)methyl-3-cephem-4-carboxylate (syn isomer)

IR (Nujol): 3300, 1770, 1650, 1610, 1530 cm$^{-1}$

NMR (D$_2$O-NaHCO$_3$, δ): 2.10 (2H, m), 2.35 (2H, m), 3.30, 3.50 (2H, ABq, J=18 Hz), 4.12 (3H, s), 5.25 (1H, d, J=5 Hz), 5.15–5.60 (3H, m), 5.80–6.30 (3H, m), 6.80 (1H, t, J=2 Hz), 7.00 (1H, s), 8.23 (2H, m)

EXAMPLE 9

7β-[2(2-Aminothiazol-4-yl)-2-methoxyiminoacetamido]-3-(2-methyl-1-pyrazolio)methyl-3-cephem-4-carboxylate (syn isomer)

IR (Nujol): 1775, 1660, 1600 cm$^{-1}$

NMR (D$_2$O, δ): 3.21 and 3.53 (2H, ABq, J=17 Hz), 4.01 (3H, s), 4.13 (3H, s), 5.26 (1H, d, J=5 Hz), 5.28 and 5.52 (2H, ABq, J=15 Hz), 5.86 (1H, d, J=5 Hz), 6.80 (1H, t, J=3 Hz), 6.99 (1H, s), 8.22 (1H, d, J=3 Hz), 8.24 (1H, d, J=3 Hz)

EXAMPLE 10

7β-[2-(2-Aminothiazol-4-yl)-2-isopropoxyiminoacetamido]-acetamido]-3-(2-methyl-1-pyrazolio)methyl-3-cephem-4-carboxylate (syn isomer)

IR (Nujol): 3300, 1770, 1660, 1610, 1530 cm$^{-1}$

NMR (D$_2$O-NaHCO$_3$, δ): 1.27(6H, d, J=6 Hz), 3.22, 3.53 (2H, ABq, J=18 Hz), 3.80 (1H, m), 4.12 (3H, s), 5.27 (1H, d, J=5 Hz), 6.80 (1H, t, J=3 Hz), 6.98 (1H, s), 8.23 (2H, m)

EXAMPLE 11

7β-[2-(2-Aminothiazol-4-yl)-2-(2-tetrahydropyranyloxyimino)acetamido]-3-(2-methyl-1-pyrazolio)methyl-3-cephem-4-carboxylate (syn isomer)

IR (Nujol): 3300, 1775, 1680, 1620 cm$^{-1}$

NMR (D$_2$O, δ): 1.40–1.95 (6H, m), 3.28, 3.50 (2H, ABq, J=18 Hz), 3.53–3.82 (2H, m), 4.09 (3H, s), 5.24 (1H, d, J=5 Hz), 5.26, 5.48 (2H, ABq, J=15 Hz), 5.40 (1H, m), 5.85 (1H, d, J=5 Hz), 6.73 (1H, t, J=2 Hz), 6.99 (1H, s), 8.16 (2H, br. s)

EXAMPLE 12

7β-[2-(2-Aminothiazol-4-yl)-2-(2-cyclopenten-1-yloxyimino)acetamido]-3-(2,5-dimethyl-1-pyrazolio)methyl-3-cephem-4-carboxylate (syn isomer)

IR (Nujol): 3300, 1770, 1660, 1600 cm$^{-1}$

NMR (D$_2$O, δ): 1.83–2.58 (4H, m), 2.43 (3H, s), 3.12, 3.42 (2H, ABq, J=18 Hz), 3.91 (3H, s), 5.17, 5.45 (2H, ABq, J=15 Hz), 5.19 (1H, d, J=5 Hz), 5.41 (1H, m), 5.80 (1H, d, J=5 Hz), 5 80–6.27 (2H, m), 6.58 (1H, d, J=3 Hz), 6.93 (1H, s), 8.05 (1H, d, J=3 Hz)

EXAMPLE 13

7β-[2-(2-Aminothiazol-4-yl)-2-(hydroxyimino)acetamido]-3-(2-methyl-1-pyrazolio)methyl-3-cephem-4-carboxylate (syn isomer)

IR (Nujol): 3320, 1775, 1660, 1620, 1600 cm$^{-1}$

NMR (D$_2$O, δ): 3.20, 3.51 (2H, ABq, J=18 Hz), 4.11 (3H, s), 5.25 (1H, d, J=5 Hz), 5 25, 5.50 (2H, ABq, J=15 Hz), 5.86 (1H, d, J=5 Hz), 6.76 (1H, t, J=2 Hz), 6.94 (1H, s), 8.18 (2H, d, J=2 Hz)

EXAMPLE 14

7β-[2-(2-Aminothiazol-4-yl)-2-(difluoromethoxyimino)acetamido]-3-(2,5-dimethyl-1-pyrazolio)methyl-3-cephem-4-carboxylate (syn isomer)

IR (Nujol): 3300, 1770, 1670, 1610 cm$^{-1}$

NMR (D$_2$O, δ): 2.43 (3H, s), 3.13, 3.43 (2H, ABq, J=18 Hz), 3.91 (3H, s), 5.18, 5.43 (2H, ABq, J=15 Hz), 5.22 (1H, d, J=5 Hz), 5.83 (1H, d, J=5 Hz), 6.56 (1H, d, J=3 Hz), 6.87 (1H, t, J=78 Hz), 7.18 (1H, s), 8.14 (1H, d, J=3 Hz)

EXAMPLE 15

7β-[2-(2-Aminothiazol-4-yl)-2-(3-cyclopenten-1-yloxyimino)acetamido]-3-(2-methyl-1-pyrazolio)methyl-3-cephem-4-carboxylate (syn isomer)

IR (Nujol) 3250, 3100, 1770, 1662, 1608 cm$^{-1}$

NMR (D$_2$O-NaHCO$_3$, δ): 2.65 (4H, m), 3.14, 3.44 (2H, ABq, J=18 Hz), 4.07 (3H, s), 5.0 (1H, m), 5.18 (1H, d, J=5 Hz), 5.21, 5.47 (2H, ABq, J=16 Hz), 5.68 (2H, s), 5.77 (1H, d, J=5 Hz), 6.73 (1H, m), 6.90 (1H, s), 8.13 (2H, m)

EXAMPLE 16

7β-[2-(2-Aminothiazol-4-yl)-2-(2-cyclopenten-1-yloxyimino)acetamido]-3-(4-hydroxymethyl-2-methyl- 1-pyrazolio)methyl-3-cephem-4-carboxylate (syn isomer)

IR (Nujol): 3260, 1765, 1660, 1605 cm$^{-1}$

NMR (D$_2$O, δ): 1.87–2.52 (4H, m), 3.27, 3.47 (2H, ABq, J=18 Hz), 4.07 (3H, s), 4.57 (2H, s), 5.20 (1H, d, J=5 Hz), 5.30 (1H, m), 5.39 (2H, br. s), 5.80 (1H, d, J=5 Hz), 5.82–6.23 (2H, m), 6.90 (1H, s), 8.14 (1H, s), 8.17 (1H, s)

EXAMPLE 17

7β-[2(2-Aminothiazol-4-yl)-2-(hydroxyimino)acetamido]-3-(4-hydroxymethyl-2-methyl-1-pyrazolio)methyl-3-cephem-4-carboxylate (syn isomer)

IR (Nujol): 3200,1765, 1660, 1600 cm$^{-1}$

NMR (D$_2$O, δ): 3.18, 3.49 (2H, ABq, J=18 Hz), 4.07 (3H, s), 4.56 (2H, s), 5.20, 5.45 (2H, ABq, J=15 Hz), 5.22 (1H, d, J=5 Hz), 5.82 (1H, d, J=5 Hz), 6.88 (1H, s), 8.18 (2H, s)

EXAMPLE 18

Sulfuric acid salt of 7β-[2-(2-aminothiazol-4-yl)-2-(difluoromethoxyimino)acetamido]-3-(2-methyl-1-pyrazolio)methyl-3-cephem-4-carboxylate (syn isomer)

NMR (D$_2$O, δ): 3.33 and 3.57 (2H, ABq, J=18 Hz), 4.15 (3H, s), 5.30 (1H, d, J=5 Hz), 5.47 (2H, br. s), 5.87 (1H, d, J=5 Hz), 6.73–6.90 (1H, m), 7.0 (1H, t, J=71 Hz), 7.40 (1H, s), 8.20–8.35 (2H, m)

EXAMPLE 19

To a solution of trifluoroacetic acid salt of 7β-[2-(2-formamidothiazol-4-yl)-2-methoxyiminoacetamido]-3-(2-methyl-1-pyrazolio)methyl-3-cephem-4-carboxylate (syn isomer, 2.2 g) in methanol (11 ml) was added conc. hydrochloric acid (0.78 ml) at room temperature, and the mixture was stirred at the same temperature for 2 hours. The reaction mixture was added to diethyl ether (300 ml), and the precipitates were collected by filtration. The precipitates were dissolved in water (20 ml) and the solution was adjusted to pH 5 with saturated aqueous solution of sodium bicarbonate. The solution was subjected to column chromatography on macroporous non-ionic adsorption resin "Diaion HP-20" and eluted with 15% aqueous solution of isopropyl alcohol The fractions containing the object compound were collected and evaporated in vacuo to remove isopropyl alcohol. The solution was lyophilized to give 7β-[2-(2-aminothiazol-4-yl)-2-methoxyiminoacetamido]-3-(2-methyl-1-pyrazolio)methyl-3-cephem-4-carboxylate (syn isomer, 0.78 g).

IR (Nujol): 1775, 1660, 1600 cm$^{-1}$

NMR (D$_2$O, δ): 3.21 and 3.53 (2H, ABq, J=17 Hz), 4.01 (3H, s), 4.13 (3H, s), 5.26 (1H, d, J=5 Hz), 5.28 and 5.52 (2H, ABq, J=15 Hz), 5.86 (1H, d, J=5 Hz), 6.80 (1H, t, J=3 Hz), 6.99 (1H, s), 8.22 (1H, d, J=3 Hz), 8.24 (1H, d, J=3 Hz)

The following compounds (Examples 20 to 28 were obtained according to a similar manner to that of Example 19.

EXAMPLE 20

7β-[2-(2-Aminothiazol-4-yl)-2-(2-cyclopenten-1-yloxyimino)acetamido]-3-(2-methyl-1-pyrazolio)methyl-3-cephem-4-carboxylate (syn isomer)

IR (Nujol): 3300, 1770, 1650, 1610, 1530 cm$^{-1}$

NMR (D$_2$O-NaHCO$_3$, δ): 2.10 (2H, m), 2.35 (2H, m), 3.30, 3.50 (2H, ABq, J=18 Hz), 4.12 (3H, s), 5.25 (1H, d, J=5 Hz), 5.15–5.60 (3H, m), 5.80–6.30 (3H, m), 6.80 (1H, t, J=2 Hz), 7.00 (1H, s), 8.23 (2H, m)

EXAMPLE 21

7β-[2-(2-Aminothiazol-4-yl)-2-(difluoromethoxyimino)acetamido]-3-(2-methyl-1-pyrazolio)methyl-3-cephem-4-carboxylate (syn isomer).

IR (Nujol): 3400, 1770, 1660, 1600, 1530 cm$^{-1}$

NMR (D$_2$O, δ): 3.20, 3.50 (2H, ABq, J=18 Hz), 4.10 (3H, s), 5.25 (1H, d, J=5 Hz), 5.25, 5.50 (2H, ABq, J=14 Hz), 5.85 (1H, d, J=5 Hz), 6.75 (1H, t, J=72 Hz), 7.20 (1H, s), 8.17 (2H, m)

EXAMPLE 22

7β-[2-(2-Aminothiazol-4-yl)-2-isopropoxyiminoacetamido]-3-(2-methyl-1-pyrazolio)methyl-3-cephem-4-carboxylate (syn isomer)

IR (Nujol): 3300, 1770, 1660, 1610, 1530 cm$^{-1}$

NMR (D$_2$O-NaHCO$_3$, δ): 1.27 (6H, d, J=6 Hz), 3.22, 3.53 (2H, ABq, J=18 Hz), 3.80 (1H, m), 4.12 (3H, s), 5.27 (1H, d, J=5 Hz), 6.80 (1H, t, J=3 Hz), 6.98 (1H, s), 8.23 (2H, m)

EXAMPLE 23

7β-[2-(2-Aminothiazol-4-yl)-2-(2-tetrahydropyranyloxyimino)acetamido]-3-(2-methyl-1-pyrazolio)methyl-3-cephem-4-carboxylate (syn isomer)

IR (Nujol) 3300, 1775, 1680, 1620 cm$^{-1}$

NMR (D$_2$O, δ): 1.40–1.95 (6H, m), 3.28, 3.50 (2H, ABq, J=18 Hz), 3.53–3.82 (2H, m), 4.09 (3H, s), 5.24 (1H, d, J=5 Hz), 5.26, 5.48 (2H, ABq, J=15 Hz), 5.40 (1H, m), 5.85 (1H, d, J=5 Hz), 6.73 (1H, t, J=2 Hz), 6.99 (1H, s), 8.16 (2H, br. s)

EXAMPLE 24

7β-[2-(2-Aminothiazol-4-yl)-2-(2-cyclopenten-1-yloxyimino)acetamido]-3-(2,5-dimethyl-1-pyrazolio)-methyl-3-cephem-4-carboxylate (syn isomer)

IR (Nujol): 3300, 1770, 1660, 1600 cm$^{-1}$

NMR (D$_2$O, δ): 1.83–2.58 (4H, m), 2.43 (3H, s), 3 12, 3.42 (2H, ABq, J=18 Hz), 3.91 (3H, s), 5.17, 5.45 (2H, ABq, J=15 Hz), 5.19 (1H, d, J=5 Hz), 5.41 (1H, m), 5.80 (1H, d, J=5 Hz), 5.80–6.27 (2H, m), 6.58 (1H, d, J=3 Hz), 6.93 (1H, s), 8.05 (1H, d, J=3 Hz)

EXAMPLE 25

7β-[2-(2-Aminothiazol-4-yl)-2-(3-thietanyloxyimino)acetamido]-3-(2-methyl-1-pyrazolio)methyl-3-cephem-4-carboxylate (syn isomer)

IR (Nujol): 1770, 1660, 1605 cm$^{-1}$

NMR (D$_2$O, δ): 3.2–3.8 (4H, m), 3.22, 3.63 (2H, ABq, J=18 Hz), 4.13 (3H, s), 5.10–5.32 (1H, m), 5.20, 5.54 (2H, ABq, J=15 Hz), 5.34 (1H, d, J=5 Hz), 5.89 (1H, d, J=5 Hz), 6.76–6.83 (1H, m), 7.03 (1H, s), 8.16–8.23 (2H, m)

EXAMPLE 26

7β-[2-(2-Aminothiazol-4-yl)-2-(2-cyclopenten-1-yloxyimino)acetamido]-3-(4-hydroxym-ethyl-2-methyl-1-pyrazolio)methyl-3-cephem-4-carboxylate (syn isomer)

IR (Nujol): 3260, 1765, 1660, 1605 cm$^{-1}$

NMR (D$_2$O, δ): 1.87–2.52 (4H, m), 3.27, 3.47 (2H, ABq, J=18 Hz), 4.07 (3H, s), 4.57 (2H, s), 5.20 (1H, d, J=5 Hz), 5.30 (1H, m), 5.39 (2H, br. s), 5.80 (1H, d, J=5 Hz), 5.82–6.23 (2H, m), 6.90 (1H, s), 8.14 (1H, s), 8.17 (1H, s)

EXAMPLE 27

7β-[2-(2-Aminothiazol-4-yl)-2-(hydroxyimino)acetamido]-3-(4-hydroxlymethyl-2-methyl-1-pyrazolio)methyl-3-cephem-4-carboxylate (syn isomer)

IR (Nujol): 3200, 1765, 1600, 1600 cm$^{-1}$

NMR (D$_2$), δ: 3.18, 3.49 (2H, ABq, J=18 Hz), 4.07 (3H, s), 4.56 (2H, s), 5.20, 5.45 (2H, ABq, J=15 Hz), 5.22 (1H, d, J=5 Hz), 5.82 (1H, d, J=5 Hz), 6.88 (1H, s), 8.18 (2H, s)

EXAMPLE 28

Sulfuric acid salt of 7β-[2-(2-aminothiazol-4-yl)-difluoromethoxyimino)acetamido]-3-(2-methyl-1- 2-difluoromethoxyimino)acetamido]-3-(2-methyl-1-pyrazolio)methyl-3-cephem-4-carboxylate (syn isomer)

NMR (D$_2$O, δ): 3.33 and 3.57 (2H, ABq, J=18 Hz), 4.15 (3H, s), 5.30 (1H, d, J=5 Hz), 5.47 (2H, br. s), 5.87 (1H, d, J=5 Hz), 6.73–6.90 (1H, m), 7.0 (1H, t, J=71 Hz), 7.40 (1H, s), 8.20–8.35 (2H, m)

EXAMPLE 29

To a solution of trifluoroacetic acid salt of 7β-[2-(2-tetrahydropyranyloxyimino)-2-(2-tritylaminothiazol-4-yl)acetamido]-3-(2-methyl-1-pyrazolio)methyl-3-cephem-4-carboxylate (syn isomer, 25.9 g), anisole (25 ml) and methylene chloride (75 ml) was added trifluoroacetic acid (50 ml) under ice-cooling with stirring. After stirred at the same temperature for 1 hour, the mixture was poured into diisopropyl ether (3500 ml).

The resulting precipitates were collected by filtration, washed with diisopropyl ether and the solid obtained was dissolved in water (700 ml). The solution was subjected to column chromatography on macroporous non-ionic adsorption resin "Diaion HP-20" and eluted with 30% aqueous solution of methanol. The fractions containing the object compound were collected, concentrated in vacuo, and lyophilized to give 7β-[2-(2-aminothiazol-4-yl)-2-(hydroxyimino)acetamido]-3-(2-methyl-1-pyrazolio)methyl-3-cephem-4-carboxylate (syn isomer, 3.90 g).

IR (Nujol): 3320, 1775, 1660, 1620, 1600 cm$^{-1}$

NMR (D$_2$O, δ): 3.20, 3.51 (2H, ABq, J=18 Hz), 4.11 (3H, s), 5.25 (1H, d, J=5 Hz), 5.25, 5.50 (2H, ABq, J=15 Hz), 5.86 (1H, d, J=5 Hz), 6.76 (1H, t, J=2 Hz), 6.94 (1H, s), 8.18 (2H, d, J=2 Hz)

EXAMPLE 30

7β-[2-(2-Aminothiazol-4-yl)-2-difluoromethoxyimino)acetamido]- 3-(2,5-dimethyl-1-pyrazolio)methyl-3-cephem-4-carboxylate (syn isomer) was prepared from trifluoroacetic acid salt of 7β-[2-difluoromethoxyimino-2-(2-tritylaminothiazol-4-yl)acetamido]-3-(2,5-dimethyl-1-pyrazolio)methyl-3-cephem-4-carboxylate (syn isomer) according to a similar manner to that of Example 29.

IR (Nujol): 3300, 1770, 1670, 1610 cm$^{-1}$

NMR (D$_2$O, δ): 2.43 (3H, s), 3.13, 3.43 (2H, ABq, J=18 Hz), 3.91 (3H, s), 5.18, 5.43 (2H, ABq, J=15 Hz), 5.22 (1H, d, J=5 Hz), 5.83 (1H, d, J=5 Hz), 6.56 (1H, d, J=3 Hz), 6.87 (1H, t, J=78 Hz), 7.18 (1H, s), 8.14 (1H, d, J=3 Hz)

EXAMPLE 31

2-(3-Cyclopenten-1-yloxyimino)-2-(2-formamidothiazol-4-yl)acetic acid (syn isomer, 2.0 g) in tetrahydrofuran (20 ml) was activated with Vilsmeier reagent prepared from N,N-dimethylformamide (0.66 ml) and phosphorus oxychloride (0.72 ml). To a solution of bis(trifluoroacetic acid) salts of 7β-amino-3-(2-methyl-1-pyrazolio)methyl-3-cephem-4-carboxylate (3.70 g) and N-mono(trimethylsilyl)acetanide (18.6 g) in tetrahydrofuran (37 ml) was added the activated acid solution obtained above under ice-cooling. After stirring at the same temperature for 1 hour, the reaction mixture was poured into a mixture of ethyl acetate (200 ml) and diisopropyl ether (200 ml). The solvent was removed by decantation. The residual glassy mass was washed with ethyl acetate by decantation and then dissolved in methanol (40 ml). To the solution was added conc. hydrochloric acid (8.2 ml) and the mixture was stirred at ambient temperature for 2 hours. The resultant solution was concentrated under reduced pressure and the residue was dissolved in water (80 ml). The solution was washed with ethyl acetate twice, and adjusted to pH 2.0 with diluted hydrochloric acid. The solution was subjected to column chromatography on macroporous non-ionic adsorption resin "Diaion HP-20", washed with water, and eluted with a mixture of 40% aqueous methanol. The fractions containing the object compound were collected, concentrated in vacuo and then lyophilized to give 7β-[2-(2-aminothiazol-4-yl)-2-(3-cyclopenten-1-yloxyimino)acetamido]-3-(2-methyl-1-pyrazoliomethyl-3-cephem-4-carboxylate (syn isomer, 1.12 g).

IR (Nujol): 3250, 3100, 1770, 1662, 1608 cm$^{-1}$

NMR (D$_2$O-NaHCO$_3$, δ): 2.65 (4H, m), 3.14, 3.44 (2H, ABq, J=18 Hz), 4.07 (3H, s), 5.0 (1H, m), 5 18 (1H, d, J=5 Hz), 5.21, 5.47 (2H, ABq, J=16 Hz), 5.68 (2H, s), 5.77 (1H, d, J=5 Hz), 6.73 (1H, m), 6.90 (1H, s), 8.13 (2H, m)

EXAMPLE 32

A mixture of 7β-[2-(2-aminothiazol-4-yl)-2-(difluoromethoxyimino)acetamido]cephalosporanic acid (syn isomer, 2 g), N-methylpyrazole (0.67 g), sodium iodide (4.2 g), water (0.7 ml) and acetonitrile (2.1 ml) was stirred at 63° to 65° C. for 3.5 hours. The reaction mixture was poured into water (130 ml) and adjusted to pH 2.0 with 10% hydrochloric acid. The solution was subjected to column chromatography on macroporous nonionic adsorption resin Diaion HP-20(100 ml) and eluted with 30% aqueous solution of methanol. The fractions containing the object compound were collected, concentrated in vacuo, and lyophilized to give 7β-[2-(2-aminothiazol-4-yl)-2-(difluoromethoxyimino)acetamido]-3-(2-methyl-1-pyrazolio)methyl-3-cephem-4-carboxylate (syn isomer, 0.15 g).

IR (Nujol): 3400, 1770, 1660, 1600, 1530 cm$^{-1}$

NMR (D$_2$O, δ): 3.20, 3.50 (2H, ABq, J=18 Hz), 4.10 (3H, s), 5.25 (1H, d, J=5 Hz), 5.25, 5.50 (2H, ABq, J=14 Hz), 5.85 (1H, d, J=5 Hz), 6.75 (1H, t, J=72 Hz), 7.20 (1H, s), 8.17 (2H, m)

The following compounds (Examples 33 to 44 were obtained according to a similar manner to that of Example 32.

EXAMPLE 33

7β-[2-(2-Aminothiazol-4-yl)-2-(2-cyclopenten-1-yloxyimino)acetamido]-3-(2-methyl-1-pyrazolio)methyl-3-cephem-4-carboxylate (syn isomer).

IR (Nujol): 3300, 1770, 1650, 1610, 1530 cm$^{-1}$

NMR (D$_2$O-NaHCO$_3$, δ): 2.10 (2H, m), 2.35 (2H, m), 3.30, 3.50 (2H, ABq, J=18 Hz), 4.12 (3H, s), 5.25 (1H, d, J=5 Hz), 5.15–5.60 (3H, m), 5.80–6.30 (3H, m), 6.80 (1H, t, J=2 Hz), 7.00 (1H, s), 8.23 (2H, m)

EXAMPLE 34

7β-[2-(2-Aminothiazol-4-yl)-2-methoxyiminoacetamido]-3-(2-methyl-1-pyrazolio)methyl-3-cephem-4-carboxylate (syn isomer).

IR (Nujol) 1775, 1660, 1600 cm$^{-1}$

NMR (D$_2$O, δ): 3.21 and 3.53 (2H, ABq, J=17 Hz), 4.01 (3H, s), 4.13 (3H, s), 5.26 (1H, d, J=5 Hz), 5.28 and 5.52 (2H, ABq, J=15 Hz), 5 86 (1H, d, J=5 Hz), 6.80 (1H, t, J=3 Hz), 6.99 (1H, s), 8.22 (1H, d, J=3 Hz), 8.24 (1H, d, J=3 Hz)

EXAMPLE 35

7β-[2-(2-Aminothiazol-4-yl)-2-(3-thietanyloxyimino)acetamido] acetamido]-3-(2-methyl-1-pyrazolio)methyl-3-cephem-4-carboxylate (syn isomer)

IR (Nujol): 1770, 1660, 1605 cm$^{-1}$

NMR (D$_2$O, δ): 3.2–3.8 (4H, m), 3.22, 3.63 (2H, ABq, J=18 Hz), 4.13 (3H, s), 5.10–5.32 (1H, m), 5.20, 5.54 (2H, ABq, J=15 Hz), 5.34 (1H, d, J=5 Hz), 5.89 (1H, d, J=5 Hz), 6.76–6.83 (1H, m), 7.03 (1H, s), 8.16–8.23 (2H, m)

EXAMPLE 36

7β-[2-(2-Aminothiazol-4-yl)-2-isopropoxyiminoacetamido]-3-(2-methyl-1-pyrazolio)methyl-3-cephem-4-carboxylate (syn isomer)

IR (Nujol): 3300, 1770, 1660, 1610, 1530 cm$^{-1}$

NMR (D$_2$O-NaHCO$_3$, δ): 1.27 (6H, d, J=6 Hz), 3.22, 3.53 (2H, ABq, J=18 Hz), 3.80 (1H, m), 4.12 (3H, s), 5.27 (1H, d, J=5 Hz), 6.80 (1H, t, J=3 Hz), 6.98 (1H, s), 8.23 (2H, m)

EXAMPLE 37

7β-[2-(2-Aminothiazol-4-yl)-2-(2-tetrahydropyranyloxyimino)acetamido]-3-(2-methyl-1-pyrazolio)methyl-3-cephem-4-carboxylate (syn isomer)

IR (Nujol): 3300, 1775, 1680, 1620 cm$^{-1}$

NMR (D$_2$O, δ): 1.40–1.95 (6H, m), 3.28, 3.50 (2H, ABq, J=18 Hz), 3.53–3.82 (2H, m), 4.09 (3H, s), 5.24 (1H, d, J=5 Hz), 5.26, 5.48 (2H, ABq, J=15 Hz), 5.40 (1H, m), 5 85 (1H, d, J=5 Hz), 6.73 (1H, t, J=2 Hz), 6.99 (1H, s), 8.16 (2H, br. s)

EXAMPLE 38

7β-[2-(2-Aminothiazol-4-yl)-2-(2-cyclopenten-1-yloxyimino)acetamido]-3-(2,5-dimethyl-1-pyrazolio)-methyl-3-cephem-4-carboxylate (syn isomer)

IR (Nujol): 3300, 1770, 1660, 1600 cm$^{-1}$

NMR (D$_2$O, δ): 1.83–2.58 (4H, m), 2.43 (3H, s), 3.12, 3.42 (2H, ABq, J=18 Hz), 3.91 (3H, s), 5.17, 5.45 (2H, ABq, J=15 Hz), 5.19 (1H, d, J=5 Hz), 5.41 (1H, m), 5.80 (1H, d, J=5 Hz), 5.80–6.27 (2H, m), 6.58 (1H, d, J=3 Hz), 6.93 (1H, s), 8.05 (1H, d, J=3 Hz)

EXAMPLE 39

7β-[2-(2-Aminothiazol-4-yl )-2-(hydroxyimino)acetamido]-3-(2-methyl-1-pyrazolio)methyl-3-cephem-4-carboxylate (syn isomer)

IR (Nujol): 3320, 1775, 1660, 1620, 1600 cm$^{-1}$

NMR (D$_2$O, δ): 3.20, 3.51 (2H, ABq, J=18 Hz), 4.11 (3H, s), 5.25 (1H, d, J=5 Hz), 5.25, 5.50 (2H, ABq, J=15 Hz), 5.86 (1H, d, J=5 Hz), 6.76 (1H, t, J=2 Hz), 6.94 (1H, s), 8.18 (2H, d, J=2 Hz)

EXAMPLE 40

7β-[2-(2-Aminothiazol-4-yl)-2-(difluoromethoxyimino)acetamido]-3-(2,5-dimethyl-1-pyrazolio)methyl-3-cephem-4-carboxylate (syn isomer)

IR (Nujol): 3300, 1770, 1670, 1610 cm$^{-1}$

NMR (D$_2$O, δ): 2.43 (3H, s), 3.13, 3.43 (2H, ABq, J=18 Hz), 3.91 (3H, s), 5.18, 5.43 (2H, ABq, J=15 Hz), 5.22 (1H, d, J=5 Hz), 5.83 (1H, d, J=5 Hz), 6.56 (1H, d, J=3 Hz), 6.87 (1H, t, J=78 Hz), 7.18 (1H, s), 8.14 (1H, d, J=3 Hz)

EXAMPLE 41

7β-[2-(2-Aminothiazol-4-yl)-2-(3-cyclopenten-1-yloxyimino)acetamido]-3-(2-methyl-1-pyrazolio)methyl-3-cephem-4-carboxylate (syn isomer)

IR (Nujol): 3250, 3100, 1770, 1662, 1608 cm$^{-1}$

NMR (D$_2$O-NaHCO$_3$, δ): 2.65 (4H, m), 3.14, 3.44 (2H, ABq, J=18 Hz), 4.07 (3H, s), 5.0 (1H, m), 5.18 (1H, d, J=5 Hz), 5.21, 5.47 (2H, ABq, J=16 Hz), 5.68 (2H, s), 5.77 (1H, d, J=5 Hz), 6.73 (1H, m), 6.90 (1H, s), 8.13 (2H, m)

EXAMPLE 42

7β-[2-(2-Aminothiazol-4-yl)-2-(2-cyclopenten-1-yloxyimino)acetamido]-3-(4-hydroxymethyl-2-methyl-1-pyrazolio)methyl-3-cephem-4-carboxylate (syn isomer)

IR (Nujol): 3260, 1765, 1660, 1605 cm$^{-1}$

NMR (D$_2$O, δ): 1.87–2.52 (4H, m), 3.27, 3.47 (2H, ABq, J=18 Hz), 4.07 (3H, s), 4.57 (2H, s), 5.20 (1H, d, J=5 Hz), 5.30 (1H, m), 5.39 (2H, br. s), 5.80 (1H, d, J=5 Hz), 5.82–6.23 (2H, m), 6.90 (1H, s), 8.14 (1H, s), 8.17 (1H, s)

EXAMPLE 43

7β-[2-(2-Aminothiazol-4-yl)-2-(hydroxyimino)acetamido]-3-(4-hydroxymethyl-2-methyl-1-pyrazolio)methyl-3-cephem-4-carboxylate (syn isomer)

IR (Nujol): 3200, 1765, 1660, 1600 cm$^{-1}$

NMR (D$_2$O, δ): 3.18, 3.49 (2H, ABq, J=18 Hz), 4.07 (3H, s), 4.56 (2H, s), 5.20, 5.45 (2H, ABq, J=15 Hz), 5.22 (1H, d, J=5 Hz), 5.82 (1H, d, J=5 Hz), 6.88 (1H, s), 8.18 (2H, s)

EXAMPLE 44

Sulfuric acid salt of 7β-[2-(2-aminothiazol-4-yl)-2-(difluoromethoxyimino)acetamido]-3-(2-methyl-1-pyrazolio)methyl-3-cephem-4-carboxylate (syn isomer)

NMR (D$_2$O, δ): 3.33, 3.57 (2H, ABq, J=18 Hz), 4.15 (3H, s), 5.30.(1H, d, J=5 Hz), 5.47 (2H, br. s), 5.87 (1H, d, J=5 Hz), 6.73–6.90 (1H, m), 7.0 (1H, t, J=71 Hz), 7.40 (1H, s), 8.20–8.35 (2H, m)

EXAMPLE 45

To a solution of benzhydryl 7β-[2-(2-aminothiazol-4-yl)-2-(2-cyclopenten-1-yloxyimino)acetamido]-3-(2-methyl-1-pyrazolio)methyl-3-cephem-4-carboxylate chloride (syn isomer, 3.6 g), anisole (3.6 ml) and methylene chloride (15 ml) was added trifluoroacetic acid (7.2 ml) under ice-cooling with stirring. After stirred at the same temperature for 1 hour, the mixture was poured into diisopropyl ether (500 ml).

The resulting precipitates were collected by filtration, washed with diisopropyl ether and the solid was dissolved in water (100 ml). The solution was subjected to column chromatography on macroporous non-ionic adsorption resin "Diaion HP-20" and eluted with 30% aqueous solution of methanol. The fractions containing the object compound were collected, concentrated in vacuo, and lyophilized to give 7β-[2-(2-aminothiazol-4-yl)-2-(2-cyclopenten-1-yloxyimino)acetamido]-3-(2- methyl-1-pyrazolio)methyl-3-cephem-4-carboxylate (syn isomer, 1.05 g).

IR (Nujol): 3300, 1770, 1650, 1610, 1530 cm$^{-1}$

NMR (D$_2$O-NaHCO$_3$, δ): 2.10 (2H, m), 2.35 (2H, m), 3.30, 3.50 (2H, ABq, J=18 Hz), 4.12 (3H, s), 5.25 (1H, d, J=5 Hz), 5.15–5.60 (3H, m), 5.80–6.30 (3H, m), 6.80 (1H, t, J=2 Hz), 7.00 (1H, s), 8.23 (2H, m)

The following compounds (Examples 46 to 55) were obtained according to a similar manner to that of Example 45.

EXAMPLE 46

7β-[2-(2-Aminothiazol-4-yl)-2-(difluoromethoxyimido)acetamido]-3-(2-methyl-1-pyrazolio)methyl-3-cephem-4-carboxylate (syn isomer)

IR (Nujol): 3400, 1770, 1660, 1600, 1530 cm$^{-1}$

NMR (D$_2$O, δ): 3.20, 3.50 (2H, ABq, J=18 Hz), 4.10 (3H, s), 5.25 (1H, d, J=5 Hz), 5.25, 5.50 (2H, ABq, J=14 Hz), 5.85 (1H, d, J=5 Hz), 6.75 (1H, t, J=72 Hz), 7.20 (1H, s), 8.17 (2H, m)

EXAMPLE 47

7β-[2-(2-Aminothiazol-4-yl)-2-methoxyiminoacetanido]-3-(2-methyl-1-pyrazolio)methyl-3-cephem-4-carboxylate (syn isomer)

IR (Nujol): 1775, 1660, 1600 cm$^{-1}$

NMR (D$_2$O, δ): 3.21 and 3.53 (2H, ABq, J=17 Hz), 4.01 (3H, s), 4.13 (3H, s), 5.26 (1H, d, J=5 Hz), 5.28 and 5.52 (2H, ABq, J=15 Hz), 5.86 (1H, d, J=5 Hz), 6.80 (1H, t, J=3 Hz), 6.99 (1H, s), 8.22 (1H, d, J=3 Hz), 8.24 (1H, d, J=3 Hz)

EXAMPLE 48

7β-[2-(2-Aminothiazol-4-yl)-2-(3-thietanyloxyimino)acetamido]-3-(2-methyl-1-pyrazolio)methyl-3-cephem-4-carboxylate (syn isomer)

IR (Nujol): 1770, 1660, 1605 cm$^{-1}$

NMR (D$_2$O, δ): 3.2–3.8 (4H, m), 3.22, 3.63 (2H, ABq, J=18 Hz), 4.13 (3H, s), 5.10–5.32 (1H, m), 5.20, 5.54 (2H, ABq, J=15 Hz), 5.34 (1H, d, J=5 Hz), 5.89 (1H, d, J=5 Hz), 6.76–6.83 (1H, m), 7.03 (1H, s), 8.16–8.23 (2H, m)

EXAMPLE 49

7β-[2-(2-Aminothiazol-4-yl)-2-isopropoxyiminoacetamido]-3-(2-methyl-1-pyrazolio)methyl-3-cephem-4-carboxylate (syn isomer)

IR (Nujol): 3300, 1770, 1660, 1610, 1530 cm$^{-1}$

NMR (D$_2$O-NaHCO$_3$, δ): 1.27 (6H, d, J=6 Hz), 3.22, 3.53 (2H, ABq, J=18 Hz), 3.80 (1H, m), 4.12 (3H, s), 5.27 (1H, d, J=5 Hz), 6.80 (1H, t, J=3 Hz), 6.98 (1H, s), 8.23 (2H, m)

EXAMPLE 50

7β-[2-(2-Aminothiazol-4-yl)-2-(2-tetrahydropyranyloxyimino)acetamido]-3-(2-methyl-1-pyrazolio)methyl-3-cephem-4-carboxylate (syn isomer)

IR (Nujol): 3300, 1775, 1680, 1620 cm$^{-1}$

NMR (D$_2$O, δ): 1.40–1.95 (6H, m), 3.28, 3.50 (2H, ABq, J=18 Hz), 3.53–3.82 (2H, m), 4.09 (3H, s), 5.24 (1H, d, J=5 Hz), 5.26, 5.48 (2H, ABq, J=15 Hz), 5.40 (1H, m), 5.85 (1H, d, J=5 Hz), 6.73 (1H, t, J=2 Hz), 6.99 (1H, s), 8.16 (2H, br. s)

EXAMPLE 51

7β-[2-(2-Aminothiazol-4-yl)-2-(2-cyclopenten-1-yloxyimino)acetamido]-3-(2,5-dimethyl-1-pyrazolio)-methyl-3-cephem-4-carboxylate (syn isomer)

IR (Nujol): 3300, 1770, 1660, 1600 cm$^{-1}$

NMR (D$_2$O, δ): 1.83–2.58 (4H, m), 2.43 (3H, s), 3.12, 3.42 (2H, ABq, J=18 Hz), 3.91 (3H, s), 5.17, 5.45 (2H, ABq, J=15 Hz), 5.19 (1H, d, J=5 Hz), 5.41 (1H, m), 5.80 (1H, d, J=5 Hz), 5.80–6.27 (2H, m), 6.58 (1H, d, J=3 Hz), 6.93 (1H, s), 8.05 (1H, d, J=3 Hz)

EXAMPLE 52

7β-[2-(2-Aminothiazol-4-yl)-2-hydroxyiminoacetamido]-3-(2-methyl-1-pyrazolio)methyl-3-cephem-4-carboxylate (syn isomer)

IR (Nujol): 3320, 1775, 1660, 1620, 1600 cm$^{-1}$

NMR (D$_2$O, δ): 3.20, 3.51 (2H, ABq, J=18 Hz), 4.11 (3H, s), 5.25 (1H, d, J=5 Hz), 5.25, 5.50 (2H, ABq, J=15 Hz), 5.86 (1H, d, J=5 Hz), 6.76 (1H, t, J=2 Hz), 6.94 (1H, s), 8.18 (2H, d, J=2 Hz)

EXAMPLE 53

7β-[2-(2-Aminothiazol-4-yl)-2-(difluoromethoxyimino)acetamido]-3-(2,5-dimethyl-1-pyrazolio)methyl-3-cephem-4-carboxylate (syn isomer)

IR (Nujol): 3300, 1770, 1670, 1610 cm$^{-1}$

NMR (D$_2$O, δ): 2.43 (3H, s), 3.13, 3.43 (2H, ABq, J=18 Hz), 3.91 (3H, s), 5.18, 5.43 (2H, ABq, J=15 Hz), 5.22 (1H, d, J=5 Hz), 5.83 (1H, d, J=5 Hz), 6.56 (1H, d, J=3 Hz), 6.87 (1H, t, J=78 Hz), 7.18 (1H, s), 8.14 (1H, d, J=3 Hz)

EXAMPLE 54

7β-[2-(2-Aminothiazol-4-yl)-2-(3-cyclopenten-1-yloxyimino)acetamido]-3-(2-methyl-1-pyrazolio)methyl-3-cephem-4-carboxylate (syn isomer)

IR (Nujol): 3250, 3100, 1770, 1662, 1608 cm$^{-1}$

NMR (D$_2$O-NaHCO$_3$, δ): 2.65 (4H, m), 3.14, 3.44 (2H, ABq, J=18 Hz), 4.07 (3H, s), 5.0 (1H, m), 5.18 (1H, d, J=5 Hz), 5.21, 5.47 (2H, ABq, J=16 Hz), 5.68 (2H, s), 5.77 (1H, d, J=5 Hz), 6.73 (1H, m), 6.90 (1H, s), 8.13 (2H, m)

EXAMPLE 55

Sulfuric acid salt of 7β-[2-(2-aminothiazol-4-yl)-2-(difluoromethoxyimino)acetamido]-3-(2-methyl-1-pyrazolio)methyl-3-cephem-4-carboxylate (syn isomer)

NMR (D$_2$O, δ): 3.33 and 3.57 (2H, ABq, J=18 Hz), 4.15 (3H, s), 5.30 (1H, d, J=5 Hz), 5.47 (2H, br. s), 5.87 (1H, d, J=5 Hz), 6.73–6.90 (1H, m), 7.0 (1H, t, J=71 Hz), 7.40 (1H, s), 8.20–8.35 (2H, m)

EXAMPLE 56

To a solution of benzhydryl 7β-[2-(2-aminothiazol-4-yl)-2-(2-cyclopenten-1-yloxyimino)acetamido]-3-(4-hydroxymethyl-2-methyl-1-pyrazolio)methyl-3-cephem-4-carboxylate chloride (syn isomer, 1.9 g), anisole (2 ml) and methylene chloride (6 ml) was added trifluoroacetic acid (4 ml) under ice-cooling with stirring. After stirring at the same temperature for 1 hour, the mixture was dissolved in water and the solution was adjusted to pH 4 with 5% aqueous solution of sodium bicarbonate. The solution was subjected to column chromatography on macroporous non-ionic adsorption resin "Diaion HP-20" and eluted with 3% aqueous solution of isopropyl alcohol. The fractions containing the object compound were collected, combined, concentrated, and finally lyophilized to give 7β-[2-(2-aminothiazol-4-yl)-2-(hydroxyimino)acetamido]-3-(4-hydroxymethyl-2-methyl-1-pyrazolio)methyl-3-cephem-4-carboxylate (syn isomer, 0.32 g).

IR (Nujol): 3200, 1765, 1660, 1600 cm$^{-1}$

NMR (D$_2$O, δ): 3.18, 3.49 (2H, ABq, J=18 Hz), 4.07 (3H, s), 4.56 (2H, s), 5.20, 5.45 (2H, ABq, J=15 Hz), 5.22 (1H, d, J=5 Hz), 5.82 (1H, d, J=5 Hz), 6.88 (1H, s), 8.18 (2H, s)

And further, the above-mentioned column was continuously eluted with 10% aqueous solution of isopropyl alcohol. The fractions containing the other object compound were collected, combined, concentrated, and finally lyophilized to give 7β-[2-(2-aminothiazol-4-yl)-2-(2-cyclopenten-1-yloxyimino)acetamido]-3-(4-hydroxymethyl-2-methyl-1-pyrazolio)methyl-3-cephem-4-carboxylate (syn isomer, 0.32 g).

IR (Nujol): 3260, 1765, 1660, 1605 cm$^{-1}$

NMR (D$_2$O, δ): 1.87–2.52 (4H, m), 3.27, 3.47 (2H, ABq, J=18 Hz), 4.07 (3H, s), 4.57 (2H, s), 5.20 (1H, d, J=5 Hz), 5.30 (1H, m), 5.39 (2H, br. s), 5.80 (1H, d, J=5 Hz), 5.82–6.23 (2H, m), 6.90 (1H, s), 8.14 (1H, s), 8.17 (1H, s)

EXAMPLE 57

A mixture of benzhydryl 7β-[2-difluoromethoxyimino-2-(2-tritylaminothiazol-4-yl)acetamido]-3-chloromethyl-3-cephem-4-carboxylate (syn isomer, 8.76 g), N-methylpyrazole (8.76 g), sodium iodide (1.5 g) and acetone (9 ml) was stirred at ambient temperature for 19 hours The reaction mixture was evaporated, and ethyl acetate (200 ml) and 5% aqueous solution of sodium thiosulfate were added to the residue. The organic layer was separated and tetrahydrofuran (100 ml) was added thereto. The solution was dried over magnesium sulfate and evaporated and the residue was dissolved in a mixture of tetrahydrofuran (200 ml) and water (65 ml). The solution was subjected to column chromatography on an ion-exchange resin "Amberlite IRA-400" (Cl$^{\ominus}$ form), and eluted with a mixture of tetrahydrofuran and water (15:1 V/V). The fractions containing the object compound were collected, combined and evaporated. The residue was triturated with diisopropyl ether to give benzhydryl 7β-[2-difluoromethoxyimino-2-(2-tritylaminothiazol-4-yl)acetamido]-3-(2-methyl-1-pyrazolio)methyl-3-cephem-4-carboxylate chloride (syn isomer, 8.0 g).

A solution of benzhydryl 7β-[2-difluoromethoxyimino-2-(2-tritylaminothiazol-4-yl)acetamido]-3-(2-methyl-1-pyrazolio)methyl-3-cephem-4-carboxylate chloride (syn isomer, 7.3 g) in methylene chloride (28 ml) was stirred at 0 to 5° C. Anisole (7 ml) and trifluoroacetic acid (28 ml) were added thereto, and the mixture was stirred for one hour at the same temperature. To the reaction mixture was added diisopropyl ether, and the precipitates were collected by filtration. The solid was washed with diisopropyl ether and dissolved in water (100 ml). The aqueous solution was adjusted to pH 2.0 with an aqueous solution of sodium bicarbonate and washed with ethyl acetate. The aqueous layer was subjected to column chromatography on macroporous non-ionic adsorption resin "Diaion HP-20" and eluted with 30% aqueous solution of methanol. The fractions containing the object compound were combined and concentrated. To the residual aqueous solution was added 1M sulfuric acid (2.2 ml) and the mixture was lyophilized to give sulfuric acid salt of 7β-[2-(2-aminothiazol-4-yl)-2-(difluoromethoxyimino)acetamido]-3-(2-methyl-1-pyrazolio)methyl-3-cephem-4-carboxylate (syn isomer, 1.35 g).

NMR (D$_2$O, δ): 3.33 and 3.57 (2H, ABq, J=18 Hz), 4.15 (3H, s), 5.30 (1H, d, J=5 Hz), 5.47 (2H, br. s), 5.87 (1H, d, J=5 Hz), 6.73–6.90 (1H, m), 7.0 (1H, t, J=71 Hz), 7.40 (1H, s), 8.20–8.35 (2H, m)

EXAMPLE 58

To a solution of 7β-[2-(2-aminothiazol-4-yl)-2-difluoromethoxyiminoacetamido]-3-(2-methyl-1-pyrazolio)methyl-3-cephem-4-carboxylate (syn isomer, 2.0 g) in water (100 ml) was added 1M sulfuric acid (3.5 ml) at ambient temperature, and the solution was lyophilized to give sulfuric acid salt of 7β-[2-(2-aminothiazol-4-yl)-2-(difluoromethoxyimino)acetamido]-3-(2-methyl-1-pyrazolio)methyl-3-cephem-4-carboxylate (syn isomer, 2.25 g).

This product (2.1 g) was recrystallized from a mixture of water (8.4 ml) and acetone (33.6 ml) to give the purified crystals of the above compound (1.3 g).

IR (Nujol): 3220, 3075, 1790, 1690, 1665, 1640, 1610, 1600 and 1550 cm$^{-1}$

NMR (D$_2$O, δ): 3.33 and 3.57 (2H, ABq, J=18 Hz), 4.15 (3H, s), 5.30 (1H, d, J=5 Hz), 5.47 (2H, br. s), 5.87 (1H, d, J=5 Hz), 6.73–6.90 (1H, m), 7.0 (1H, t, J=71 Hz), 7.40 (1H, s), 8.20–8.35 (2H, m)

EXAMPLE 59

To a solution of benzhydryl 7β-[2-[2-tritylaminothiazol-4-yl)-2-difluoromethoxyiminoacetamido]-3-(4-methoxy-2-methyl-1-pyrazolio)methyl-3-cephem-4-carboxylate trifluoroacetate (syn isomer) (2.1 g), anisole (2 ml) and methylene chloride (6 ml) was added trifluoroacetic acid (4 ml) under ice-cooling with stirring. After stirred at the same temperature for 1 hour, the mixture was poured into diethyl ether.

The resulting precipitates were collected by filtration, washed with diethyl ether and the solid was dissolved in water, then the solution was adjusted to pH 4 with 5% sodium bicarbonate aqueous solution.

The solution was subjected to column chromatography on macroporous non-ionic adsorption resin "Diaion HP-20" (30 ml) and eluted with 5% aqueous solution of isopropyl alcohol. The fractions containing the object compound were collected, concentrated in vacuo and lyophilized to give 7β-[2-(2-aminothiazol-4-yl)-2-difluoromethoxyiminoacetamido]-3-(4-methoxy-2-methyl-1-pyrazolio)methyl-3-cephem-4-carboxylate (syn isomer) (0.63 g).

IR (Nujol): 3300, 1775, 1675, 1605 cm$^{-1}$

NMR (D$_2$O, δ): 3.18, 3.50 (2H, ABq, J=18 Hz), 3.84 (3H, s), 4.04 (3H, s), 5.16 and 5.44 (2H, ABq, J=15 Hz), 5.24 (1H, d, J=5 Hz), 5.83 (1H, d, J=5 Hz), 6.88 (1H, t, J=78 Hz), 7.16 (1H, s), 7.96 (2H, br. s)

EXAMPLE 60

To a solution of benzhydryl 7β-[2-(2-aminothiazol-4-yl)-2-(2-cyclopenten-1-yloxyimino)acetamido]-3-(4-methoxy-2-methyl-1-pyrazolio)methyl-3-cephem-4-carboxylate trifluoroacetate (syn isomer) (2.5 g), anisole (2.5 ml) and methylene chloride (7.5 ml) was added trifluoroacetic acid (5 ml) under ice-cooling with stirring. After stirred at the same temperature for 1.5 hours, the mixture was poured into diethyl ether.

The resulting precipitates were collected by filtration, washed with diethyl ether and the solid was dissolved in water, then the solution was adjusted to pH 4 with 5% sodium bicarbonate aqueous solution.

The solution was subjected to column chromatography on macroporous non-ionic adsorption resin "Diaion HP-20" (50 ml) and first eluted with 3% aqueous solution of isopropyl alcohol. The fractions containing the object compound were collected, concentrated in vacuo and lyophilized to give 7β-[2-(2-aminothiazol-4-yl)-2-hydroxyiminoacetamido]-3-(4-methoxy-2-methyl-1-pyrazolio)methyl-3-cephem-4-carboxylate (syn isomer) (0.345 g).

IR (Nujol): 3250, 1765, 1660, 1600 cm$^{-1}$

NMR (D$_2$O, δ): 3.17 and 3.47 (2H, ABq, J=18 Hz), 3.81 (3H, s), 4.01 (3H, s), 5.12 and 5.41 (2H, ABq, J=16 Hz), 5.18 (1H, d, J=5 Hz), 5.78 (1H, d, J=5 Hz), 6.84 (1H, s), 7.97 (2H, s)

Second, the elution was carried out with 15% aqueous solution of isopropyl alcohol. The fractions containing the object compound were collected, concentrated in vacuo and lyophilized to give 7β-[2-(2-aminothiazol-4-yl)-2-(2-cyclopenten-1-yloxyimino)acetamido]-3-(4-methoxy-2-methyl-1-pyrazolio)methyl-3-cephem-4-carboxylate (syn isomer) (0.162 g).

IR (Nujol): 3300, 1675, 1605 cm$^{-1}$

NMR (D$_2$O, δ): 1.69–2.56 (4H, m), 3.16, 3.46 (2H, ABq, J=18 Hz), 3.74 (3H, m), 4.03 (3H, m), 5.17 (1H, d, J=5 Hz), 5.33 (3H, m), 5.76 (1H, d, J=5 Hz), 5.77–6.22 (2H, m), 6.87 (1H, s), 7.97 (2H, s)

The following compounds (Examples 61 to 78) were obtained according to a similar manner to that of Example 1.

EXAMPLE 61

7β-[2-(2-Tritylaminothiazol-4-yl)-2-methoxyiminoacetamido]-3-(3-formamido-2-methyl-1-pyrazolio)methyl-3-cephem-4-carboxylate (syn isomer)

IR (Nujol): 3350, 1775, 1660, 1580 cm$^{-1}$

NMR (DMSO-d$_6$, δ): 3.34 (2H, broad s), 3.77 (3H, s), 3.91 (3H, s), 5.11 (1H, d, J=5 Hz), 5.41 (2H, broad s), 5.69 (1H, dd, J=8 Hz and 5 Hz), 6.94 (1H, d, J=3 Hz), 7.00–7.60 (16H, m), 8.32 (1H, d, J=3 Hz), 8.47 (1H, s), 8.70 (1H, s), 9.47 (1H, d, J=8 Hz)

EXAMPLE 62

7β-[2-(2-Formamidothiazol-4-yl)-2-tert-butoxycarbonylmethoxyiminoacetamido]-3-(3-formamido-2-methyl-1-pyrazolio)methyl-3-cephem-4-carboxylate (syn isomer)

IR (Nujol): 1770, 1670, 1605 cm$^{-1}$

NMR (D$_2$O+DMSO-d$_6$, δ): 1.43 (9H, s), 3.07 and 3.38 (2H, ABq, J=18 Hz), 3.87 (3H, s), 4.63 (2H, s), 5.08 (1H, d, J=5 Hz), 5.20 and 5.44 (2H, ABq, J=16 Hz), 5.74 (1H, d, J=5 Hz), 6.87 (1H, m), 7.45 (1H, s), 8.22 (1H, d, J=3 Hz), 8.43 (1H, s), 8.47 (1H, s)

EXAMPLE 63

7β-[2-(2-Aminothiazol-4-yl)-2-methoxyiminoacetamido]-3-(3-formamido-2-methyl-1-pyrazolio)methyl-3-cephem-4-carboxylate (syn isomer)

IR (Nujol): 3350, 1770, 1660, 1610 cm$^{-1}$

EXAMPLE 64

7β-[2-(2-Aminothiazol-4-yl)-2-(difluoromethoxyimino)acetamido]-3-(4-formamido-2-methyl-1-pyrazolio)methyl-3-cephem-4-carboxylate (syn isomer)

IR (Nujol): 1775, 1675, 1605 cm$^{-1}$

EXAMPLE 65

7β-[2-(2-Aminothiazol-4-yl)-2-(difluoromethoxyimino)acetamido]-3-(3-formamido-2-methyl-1-pyrazolio)methyl-3-cephem-4-carboxylate (syn isomer)

IR (Nujol): 3300, 1770, 1665 cm$^{-1}$

EXAMPLE 66

7β-[2-(2-Aminothiazol-4-yl)-2-methoxyiminoacetamido]-3-(3-amino-2-methyl-1-pyrazolio)-methyl-3-cephem-4-carboxylate.trihydrochloride (syn isomer)

IR (Nujol): 3300, 1770, 1660, 1630 cm$^{-1}$

EXAMPLE 67

7β-[2-(2-Aminothiazol-4-yl)-2-(difluoromethoxyimino)acetamido]-3-(3-amino-2-methyl-1-pyrazolio)-methyl-3-cephem-4-carboxylate (syn isomer)

IR (Nujol): 3300, 1765, 1660 cm$^{-1}$

EXAMPLE 68

7β-[2-(2-Aminothiazol-4-yl)-2-(difluoromethoxyimino)acetamido]-3-(4-amino-2-methyl-1-pyrazolio)-methyl-3-cephem-4-carboxylate (syn isomer)

IR (Nujol): 1760, 1660, 1600 cm$^{-1}$

EXAMPLE 69

7β-[2-(2-Aminothiazol-4-yl)-2-tert-butoxycarbonylmethoxyiminoacetamido]-3-(3-amino-2-methyl-1-pyrazolio)methyl-3-cephem-4-carboxylate.trihydrochloride (syn isomer)

IR (Nujol): 3300, 1775, 1715, 1670, 1630 cm$^{-1}$

EXAMPLE 70

Benzhydryl 7β-[2-(2-tritylaminothiazol-4-yl)-2-(difluoromethoxyimino)acetamido]-3-(4-formamido-2-methyl-1-pyrazolio)methyl-3-cephem-4-carboxylate.trifluoroacetate (syn isomer)

IR (Nujol): 1795, 1725, 1675, 1615 cm$^{-1}$

EXAMPLE 71

Benzhydryl 7β-[2-(2-tritylaminothiazol-4-yl)-2-(difluoromethoxyimino)acetamido]-3-(3-formamido-2-methyl-1-pyrazolio)methyl-3-cephem-4-carboxylate.trifluoroacetate (syn isomer)

IR (Nujol): 3200, 1790, 1720, 1680 cm$^{-1}$

EXAMPLE 72

7β-[2-(2-Aminothiazol-4-yl)-2-carboxymethoxyiminoacetamido]-3-(3-amino-2-methyl-1-pyrazolio)-methyl-3-cephem-4-carboxylate (syn isomer)

IR (Nujol): 3300, 1760, 1650 cm$^{-1}$

EXAMPLE 73

7β-[2-(2-Aminothiazol-4-yl)-2-methoxyiminoacetamido]-3-(2,5-dimethyl-1-pyrazolio)methyl-3-cephem-4-carboxylate (syn isomer)

IR (Nujol): 3300, 1760, 1660, 1605 cm$^{-1}$

EXAMPLE 74

7β-[2-(2-Aminothiazol-4-yl)-2-methoxyiminoacetamido]-3-(3-amino-2,4-dimethyl-1-pyrazolio)methyl-3-cephem-4-carboxylate (syn isomer)

IR (Nujol): 3300, 1770, 1640, 1600 cm$^{-1}$

EXAMPLE 75

Benzhydryl 7β-[2-(2-tritylaminothiazol-4-yl)-2-(difluoromethoxyimino)acetamido]-3-(3-formamido-2,4-dimethyl-1-pyrazolio)methyl-3-cephem-4-carboxylate trifluoroacetate (syn isomer)

IR (Nujol): 1785, 1720, 1675 cm$^{-1}$

EXAMPLE 76

7β-[2-(2-Aminothiazol-4-yl)-2-(difluoromethoxyimino)acetamido]-3-(3-formamido-2,4-dimethyl-1-pyrazolio)methyl-3-cephem-4-carboxylate (syn isomer)

IR (Nujol): 3250, 1765, 1665, 1600 cm$^{-1}$

EXAMPLE 77

7β-[2-(2-Aminothiazol-4-yl)-2-(difluoromethoxyimino)acetamido]-3-(3-amino-2,4-dimethyl-1-pyrazolio)methyl-3-cephem-4-carboxylate (syn isomer)

IR (Nujol): 3300, 1765, 1640, 1600 cm$^{-1}$

EXAMPLE 78

Trifluoroacetic acid salt of 7β-[2-(2-formamidothiazol-4-yl)-2-methoxyiminoacetamido]-3-(2,5-dimethyl-1-pyrazolio)methyl-3-cephem-4-carboxylate (syn isomer)

IR (Nujol): 3350, 1770, 1655 cm$^{-1}$

NMR (DMSO-d$_6$, δ): 2.50 (3H, s), 3.40 (2H, broad s), 3.88 (3H, s), 4.03 (3H, s), 5.19 (1H, d, J=5 Hz), 5.52 (2H, broad s), 5.88 (1H, dd, J=8 Hz and 5 Hz), 6.77 (1H, broad s), 7.39 (1H, s), 8.37 (1H, broad s), 8.50 (1H, s), 9.67 (1H, d, J=8 Hz)

EXAMPLE 79

The Vilsmeier reagent was prepared in the usual manner. 2-(2-Formamidothiazol-4-yl)-2-methoxyiminoacetic acid (syn isomer) (1.19 g) was activated with Vilsmeier reagent in ethyl acetate (3 ml) and tetrahydrofuran (6 ml) under ice-cooling for 30 minutes. This activated acid solution was added to a solution of bis(trifluoroacetic acid) salts of 7β-amino-3-(3-formamido-2,4-dimethyl-1-pyrazolio)methyl-3-cephem-4-carboxylate (3 g) and bis(trimethylsilyl)acetamide (5.12 ml) in tetrahydrofuran (30 ml) under ice-cooling. After being stirred at the same temperature for 1 hour, the reaction mixture was added dropwise to diethyl ether (300 ml), and the resulting precipitate was collected by filtration to give trifluoroacetic acid salt of 7β-[2-(2-formamidothiazol-4-yl)-2-methoxyiminoacetamido]-3-(3-formamido-2,4-dimethyl-1-pyrazolio)methyl-3-cephem-4-carboxylate (syn isomer) (3.10 g).

IR (Nujol): 3300, 1780, 1650 cm$^{-1}$

NMR (DMSO-d$_6$, δ): 1.99 (3H, s), 3.41 (2H, broad s), 3.83 (3H, s), 3.88 (3H, s), 5.22 (1H, d, J=5 Hz), 5.46 (2H, broad s), 5.88 (1H, dd, J=5 Hz and 8 Hz), 7.38 (1H, s), 8.27 (1H, s), 8.37 (1H, s), 8.49 (1H, s), 9.68 (1H, d, J=5 Hz)

EXAMPLE 80

2-(2-Aminothiazol-4-yl)-2-methoxyiminoacetic acid (syn isomer) activated by 1-hydroxy-1H-benzotriazole was prepared by reacting 2-(2-aminothiazol-4-yl)-2-methoxyiminoacetic acid (syn isomer) (24.14 g), dicyclohexylcarbodiimide (24.76 g), 1-hydroxy-1H-benzotriazole (16.12 g) and 4-(N,N-dimethylamino)pyridine (733 mg) according to a conventional manner. 1.04 g of activated acid thus obtained was added to a solution of bis(trifluoroacetic acid) salt of 7β-amino-3-(4-formamido-2-methyl-1-pyrazolio)methyl-3-cephem-4-carboxylate (1.5 g) in tetrahydrofuran (40 ml) and water (20 ml) at ambient temperature. The mixture was stirred for 4 hours keeping the pH 7 to 7.5 with saturated aqueous sodium bicarbonate solution, and the mixture was washed with ethyl acetate. The aqueous layer was adjusted to pH 3 with 1N hydrochloric acid and extracted with ethyl acetate five times. The solvent was evaporated in vacuo and the residue was subjected to a column chromatography on macroporous non-ionic adsorption resin "Diaion HP-20". The object compound was eluted with 5% aqueous isopropyl alcohol solution and lyophilized to give 7β-[2-(2-aminothiazol-4-yl)-2-methoxyiminoacetamido]-3-(4-formamido-2-methyl-1-pyrazolio)methyl-3-cephem-4-carboxylate (syn isomer) (407.5 mg).

IR (Nujol): 3300, 1770, 1665, 1605 cm$^{-1}$

NMR (D$_2$O+NaHCO$_3$, δ): 3.20 and 3.57 (2H, ABq, J=18 Hz), 3.98 (3H, s), 4.10 (3H, s), 5.26 (1H, d, J=5 Hz), 5.27 and 5.51 (2H, ABq, J=15 Hz), 5.85 (1H, d, J=5 Hz), 7.00 (1H, s), 8.34 (1H, s), 8.48 (1H, s), 8.50 (1H, s)

EXAMPLE 81

7β-[2-(2-Aminothiazol-4-yl)-2-methoxyiminoacetamido]-3-(3-formamido-2,4-dimethyl-1-pyrazolio)methyl-3-cephem-4-carboxylate (syn isomer) was obtained according to a similar manner to that of Example 80.

IR (Nujol): 3300, 1765, 1665, 1600 cm$^{-1}$

NMR (D$_2$O, δ): 2.04 (3H, s), 3.20 and 3.53 (2H, ABq, J=18 Hz), 3.88 (3H, s), 3.99 (3H, s), 5.23 and 5.47 (2H, ABq, J=15 Hz), 5.25 (1H, d, J=5 Hz), 5.84 (1H, d, J=5 Hz), 6.99 (1H, s), 8.13 (1H, s), 8.43 (1H, s)

The following compounds (Examples 82 to 87) were obtained according to a similar manner to that of Example 19.

EXAMPLE 82

7β-[2-(2-Aminothiazol-4-yl)-2-methoxyiminoacetamido]-3-(2,5-dimethyl-1-pyrazolio)methyl-3-cephem-4-carboxylate (syn isomer)

IR (Nujol): 3300, 1760, 1660, 1605 cm$^{-1}$

NMR (D$_2$O, δ): 2.54 (3H, s), 3.0–3.6 (2H, m), 4.03 (3H, s), 4.08 (3H, s), 5.1–5.7 (2H, m), 5.26 (1H, d, J=5 Hz), 5.86 (1H, d, J=5 Hz), 6.63 (1H, broad s), 7.00 (1H, s), 8.09 (1H, broad s)

EXAMPLE 83

7β-[2-(2-Aminothiazol-4-yl)-2-carboxymethoxyiminoacetamido]-3-(3-amino-2-methyl-1-pyrazolio)methyl-3-cephem-4-carboxylate (syn isomer)

IR (Nujol): 3300, 1760, 1650 cm$^{-1}$

EXAMPLE 84

7β-[2-(2-Aminothiazol-4-yl)-2-methoxyiminoacetamido]-3-(3-amino-2-methyl-1-pyrazolio)methyl-3-cephem-4-carboxylate trihydrochloride (syn isomer)

IR (Nujol): 3300, 1770, 1660, 1630 cm$^{-1}$

EXAMPLE 85

7β-[2-(2-Aminothiazol-4-yl)-2-(difluoromethoxyimino)acetamido]-3-(3-amino-2-methyl-1-pyrazolio)methyl-3-cephem-4-carboxylate (syn isomer)

IR (Nujol): 3300, 1765, 1660 cm$^{-1}$

EXAMPLE 86

7β-[2-(2-Aminothiazol-4-yl)-2-(difluoromethoxyimino)acetamido]-3-(4-amino-2-methyl-1-pyrazolio)methyl-3-cephem-4-carboxylate (syn isomer)

IR (Nujol): 1760, 1660, 1600 cm$^{-1}$

EXAMPLE 87

7β-[2-(2-Aminothiazol-4-yl)-2-(difluoromethoxyimino)acetamido]-3-(3-amino-2,4-dimethyl-1-pyrazolio)methyl-3-cephem-4-carboxylate (syn isomer)

IR (Nujol): 3300, 1765, 1640, 1600 cm$^{-1}$

EXAMPLE 88

7β-[2-(2-Aminothiazol-4-yl)-2-tert-butoxycarbonylmethoxyiminoacetamido]-3-(3-amino-2-methyl-1-pyrazolio)methyl-3-cephem-4-carboxylate.trihydrochloride (syn isomer) was obtained from 7β-[2-(2-for-mamidothiazol-4-yl)-2-tert-butoxycarbonylmethox-yiminoacetamido]-3-(3-formamido-2-methyl-1-pyrazolio)methyl-3-cephem-4-carboxylate (syn isomer) according to a similar manner to that of Example 19.
IR (Nujol): 3300, 1775, 1715, 1670, 1630 cm$^{-1}$
NMR (D$_2$O, δ): 1.48 (9H, s), 3.25–3.50 (2H, m), 3.68 (3H, s), 4.68 (2H, s), 5.21 (2H, broad s), 5.24 (1H, d, J=5 Hz), 5.83 (1H, d, J=5 Hz), 5.93 (1H, d, J=3 Hz), 7.19 (1H, s), 7.82 (1H, d, J=3 Hz)

EXAMPLE 89

To a solution of trifluoroacetic acid salt of 7β-[2-(2-formamidothiazol-4-yl)-2-methoxyiminoacetamido]-3-(2,4-dimethyl-3-formamido-1-pyrazolio)methyl-3-cephem-4-carboxylate (syn isomer) (3 g) in methanol (15 ml) was added concentrated hydrochloric acid (1.57 ml) at ambient temperature. After being stirred at the same temperature for 4 hours, the reaction mixture was added dropwise to diethyl ether, and the resulting precipitate was collected by filtration. The precipitate was dissolved in water, and the solution was adjusted to pH 2 with aqueous 5% sodium bicarbonate solution and subjected to column chromatography on macroporous non-ionic adsorption resin "Diaion HP-20". The desired compound was eluted with aqueous 5% isopropyl alcohol solution. The objective fractions were collected and the isopropyl alcohol was evaporated. The resulting aqueous solution was lyophilized to give 7β-[2-(2-aminothiazol-4-yl)-2-methoxyiminoacetamido]-3-(3-amino-2,4-dimethyl-1-pyrazolio)methyl-3-cephem-4-carboxylate (syn isomer) (763.5 mg).
IR (Nujol): 3300, 1770, 1640, 1600 cm$^{-1}$
NMR (D$_2$O, δ): 1.93 (3H, s), 3.08 and 3.33 (2H, ABq, J=18 Hz), 3.65 (3H, s), 3.98 (3H, s), 4.88 and 5.21 (2H, ABq, J=15 Hz), 5.18 (1H, d, J=5 Hz), 5.81 (1H, d, J=5 Hz), 6.97 (1H, s), 7.66 (1H, s)

The following compounds (Examples 90 to 95) were obtained according to a similar manner to that of Example 29.

EXAMPLE 90

7β-[2-(2-Aminothiazol-4-yl)-2-methoxyiminoacetamido]-3-(3-formamido-2-methyl-1-pyrazolio)methyl-3-cephem-4-carboxylate (syn isomer)
IR (Nujol): 3350, 1770, 1660, 1610 cm$^{-1}$
NMR (D$_2$O, δ): 3.17 and 3.50 (2H, ABq, J=18 Hz), 3.93 (3H, s), 3.98 (3H, s), 5.20 and 5.44 (2H, ABq, J=16 Hz), 5.21 (1H, d, J=5 Hz), 5.81 (1H, d, J=5 Hz), 6.96 (1H, m), 6.97 (1H, s), 8.16 (1H, d, J=3 Hz), 8.43 (1H, s)

EXAMPLE 91

7β-[2-(2-Aminothiazol-4-yl)-2-(difluoromethoxyimino)acetamido]-3-(3-formamido-2-methyl-1-pyrazolio)methyl-3-cephem-4-carboxylate (syn isomer)
IR (Nujol): 3300, 1770, 1665 cm$^{-1}$
NMR (D$_2$O, δ): 3.12 and 3.42 (2H, ABq, J=18 Hz), 3.87 (3H, s), 5.15 and 5.42 (2H, ABq, J=16 Hz), 5.19 (1H, d, J=5 Hz), 5.81 (1H, d, J=5 Hz), 6.75 (1H, d, J=3 Hz), 6.84 (1H, t, J=77 Hz), 7.11 (1H, s), 8.06 (1H, d, J=3 Hz), 8.43 (1H, s)

EXAMPLE 92

7β-[2-(2-Aminothiazol-4-yl)-2-(difluoromethoxyimino)acetamido]-3-(4-formamido-2-methyl-1-pyrazolio)methyl-3-cephem-4-carboxylate (syn isomer)
IR (Nujol): 1775, 1675, 1605 cm$^{-1}$
NMR (D$_2$O, δ): 3.20 and 3.50 (2H, ABq, J=17 Hz), 4.09 (3H, s), 5.22 and 5.50 (2H, ABq, J=15 Hz), 5.23 (1H, d, J=5 Hz), 5.83 (1H, d, J=5 Hz), 6.87 (1H, t, J=77 Hz), 7.13 (1H, s), 8.23 (1H, s), 8.39 (2H, s)

EXAMPLE 93

7β-[2-(2-Aminothiazol-4-yl)-2-(difluoromethoxyimino)acetamido]-3-(3-formamido-2,4-dimethyl-1-pyrazolio)methyl-3-cephem-4-carboxylate (syn isomer)
IR (Nujol): 3250, 1765, 1665, 1600 cm$^{-1}$
NMR (D$_2$O, δ): 2.03 (3H, s), 3.21 and 3.50 (2H, ABq, J=18 Hz), 3.83 (3H, s), 5.19 and 5.45 (2H, ABq, J=15 Hz), 5.29 (1H, d, J=5 Hz), 5.88 (1H, d, J=5 Hz), 6.93 (1H, t, J=71 Hz), 7.26 (1H, s), 8.07 (1H, s), 8.38 (1H, s)

EXAMPLE 94

7β-[2-(2-Aminothiazol-4-yl)-2-methoxyiminoacetamido]-3-(4-formamido-2-methyl-1-pyrazolio)methyl-3-cephem-4-carboxylate (syn isomer)
IR (Nujol): 3300, 1770, 1665, 1605 cm$^{-1}$

EXAMPLE 95

7β-[2-(2-Aminothiazol-4-yl)-2-methoxyiminoacetamido]-3-(3-formamido-2,4-dimethyl-1-pyrazolio)methyl-3-cephem-4-carboxylate (syn isomer)
IR (Nujol): 3300, 1765, 1665, 1600 cm$^{-1}$ The following compounds (Examples 96 to 116) were obtained according to a similar manner to that of Example 32.

EXAMPLE 96

Benzhydryl 7β-[2-(2-tritylaminothiazol-4-yl)-2-(difluoromethoxyimino)acetamido]-3-(3-formamido-2-methyl-1-pyrazolio)methyl-3-cephem-4-carboxylate.trifluoroacetate (syn isomer)
IR (Nujol): 3200, 1790, 1720, 1680 cm$^{-1}$
NMR (DMSO-d$_6$, δ): 3.41 (2H, m), 3.67 (3H, s), 5.22 (1H, d, J=5 Hz), 5.40 (2H, m), 5.82 (1H, dd, J=8 Hz and 5 Hz), 6.90 (1H, s), 6.93 (1H, s), 6.97 (1H, s), 7.02 (1H, t, J=77 Hz), 7.02–7.63 (25H, m), 8.22 (1H, s), 8.52 (1H, s), 8.88 (1H, s), 9.85 (1H, d, J=8 Hz)

EXAMPLE 97

Benzhydryl 7β-[2-(2-tritylaminothiazol-4-yl)-2-(difluoromethoxyimino)acetamido]-3-(4-formamido-2-methyl-1-pyrazolio)methyl-3-cephem-4-carboxylate.trifluoroacetate (syn isomer)
IR (Nujol): 1795, 1725, 1675, 1615 cm$^{-1}$
NMR (DMSO-d$_6$, δ): 3.40 (2H, broad s), 3.83 (3H, s), 5.22 (1H, d, J=5 Hz), 5.41 (2H, broad s), 5.81 (1H, dd, J=5 Hz and 8 Hz), 6.91 (1H, s), 6.95 (1H, s), 7.01 (1H, t, J=78 Hz), 7.03–7.63 (25H, m), 8.27 (1H, s), 8.48 (1H, s), 8.57 (1H, s), 8.86 (1H, s), 9.88 (1H, d, J=8 Hz), 10.81 (1H, s)

EXAMPLE 98

Benzhydryl 7β-[2-(2-tritylaminothiazol-4-yl)-2-(difluoromethoxyimino)acetamido]-3-(3-formamido-2,4-dimethyl-1-pyrazolio)methyl-3-cephem-4-carboxylate (syn isomer)
IR (Nujol): 1785, 1720, 1675 cm$^{-1}$
NMR (DMSO-d$_6$, δ): 1.98 (3H, s), 3.43 (2H, broad s), 3.64 (3H, s), 5.28 (1H, d, J=5 Hz), 5.44 (2H, broad s), 5.85 (1H, dd, J=5 Hz and 8 Hz), 6.94 (1H, s), 7.02 (1H, s), 7.10 (1H, t, J=72 Hz), 7.12–7.64 (25H, m), 8.21 (1H, s), 8.43 (1H, s), 8.96 (1H, s), 9.95 (1H, d, J=5 Hz)

EXAMPLE 99

7β-[2-(2-Tritylaminoithiazol-4-yl)-2-methoxyiminoacetamido]-3-(3-formamido-2-methyl-1-pyrazolio)methyl-3-cephem-4-carboxylate (syn isomer)

IR (Nujol): 3350, 1775, 1660, 1580 cm$^{-1}$

EXAMPLE 100

7β-[2-(2-Formamidothiazol-4-yl)-2-tert-butoxy-carbonylmethoxyiminoacetamido]-3-(3-formamido-2-methyl-1-pyrazolio)methyl-3-cephem-4-carboxylate (syn IR (Nujol): 1770, 1670, 1605 cm$^{-1}$

EXAMPLE 101

7β-[2-(2-Aminothiazol-4-yl)-2-methoxyiminoacetamido]-3-(3-formamido-2-methyl-1-pyrazolio)methyl-3-cephem-4-carboxylate (syn isomer)

IR (Nujol): 3350, 1770, 1660, 1610 cm$^{-1}$

EXAMPLE 102

7β-[2-(2-Aminothiazol-4-yl)-2-(difluoromethoxyimino)acetamido]-3-(4-formamido-2-methyl-1-pyrazolio)methyl-3-cephem-4-carboxylate (syn isomer)

IR (Nujol): 1775, 1675, 1605 cm$^{-1}$

EXAMPLE 103

7β-[2-(2-Aminothiazol-4-yl)-2-(difluoromethoxyimino)acetamido]-3-(3-formamido-2-methyl-1-pyrazolio)methyl-3-cephem-4-carboxylate (syn isomer)

IR (Nujol): 3300, 1770, 1665 cm$^{-1}$

EXAMPLE 104

7β-[2-(2-Aminothiazol-4-yl)-2-methoxyiminoacetamido]-3-(3-amino-2-methyl-1-pyrazolio)-methyl-3-cephem-4-carboxylate.trihydrochloride (syn isomer)

IR (Nujol): 3300, 1770, 1660, 1630 cm$^{-1}$

EXAMPLE 105

7β-[2-(2-Aminothiazol-4-yl)-2-(difluoromethoxyimino)acetamido]-3-(3-amino-2-methyl-1-pyrazolio)-methyl-3-cephem-4-carboxylate (syn isomer)

IR (Nujol): 3300, 1765, 1660 cm$^{-1}$

EXAMPLE 106

7β-[2-(2-Aminothiazol-4-yl)-2-(difluoromethoxyimino)acetamido]-3-(4-amino-2-methyl-1-pyrazolio)-methyl-3-cephem-4-carboxylate (syn isomer)

IR (Nujol): 1760, 1660, 1600 cm$^{-1}$

EXAMPLE 107

7β-[2-(2-Aminothiazol-4-yl)-2-tert-butoxycarbonylmethoxyiminoacetamido]-3-(3-amino-2-methyl-1-pyrazolio)methyl-3-cephem-4-carboxylate.trihydrochloride (syn isomer)

IR (Nujol): 3300, 1775, 1715, 1670, 1630 cm$^{-1}$

EXAMPLE 108

7β-[2-(2-Aminothiazol-4-yl)-2-carboxymethoxyiminoacetamido]-3-(3-amino-2-methyl-1-pyrazolio)-methyl-3-cephem-4-carboxylate (syn isomer)

IR (Nujol): 3300, 1760, 1650 cm$^{-1}$

EXAMPLE 109

7β-[2-(2-Aminothiazol-4-yl)-2-methoxyimino]-3-(2,5-dimethyl-1-pyrazolio)methyl-3-cephem-4-carboxylate (syn isomer)

IR (Nujol): 3300, 1760, 1660, 1605 cm$^{-1}$

EXAMPLE 110

7β-[2-(2-Aminothiazol-4-yl)-2-methoxyiminoacetamido]-3-(3-amino-2,4-dimethyl-1-pyrazolio)methyl-3-cephem-4-carboxylate (syn isomer)

IR (Nujol): 3300, 1770, 1640, 1600 cm$^{-1}$

EXAMPLE 111

7β-[2-(2-Aminothiazol-4-yl)-2-(difluoromethoxyimino)acetamido]-3-(3-formamido-2,4-dimethyl-1-pyrazolio)methyl-3-cephem-4-carboxylate (syn isomer)

IR (Nujol): 3250, 1765, 1665, 1600 cm$^{-1}$

EXAMPLE 112

7β-[2-(2-Aminothiazol-4-yl)-2-(difluoromethoxyimino)acetamido]-3-(3-amino-2,4-dimethyl-1-pyrazolio)methyl-3-cephem-4-carboxylate (syn isomer)

IR (Nujol): 3300, 1765, 1640, 1600 cm$^{-1}$

EXAMPLE 113

Trifluoroacetic acid salt of 7β-[2-(2-formamidothiazol-4-yl)-2-methoxyiminoacetamido]-3-(2,5-dimethyl-1-pyrazolio)methyl-3-cephem-4-carboxylate (syn isomer)

IR (Nujol): 3350, 1770, 1655 cm$^{-1}$

EXAMPLE 114

Trifluoroacetic acid salt of 7β-[2-(2-formamidothiazol-4-yl)-2-methoxyiminoacetamido]-3-(3-formamido-2,4-dimethyl-1-pyrazolio)methyl-3-cephem-4-carboxylate (syn isomer)

IR (Nujol): 3300, 1780, 1650 cm$^{-1}$

EXAMPLE 115

7β-[2-(2-Aminothiazol-4-yl)-2-methoxyiminoacetamido]-3-(4-formamido-2-methyl-1-pyrazolio)methyl-3-cephem-4-carboxylate (syn isomer)

IR (Nujol): 3300, 1770, 1665, 1605 cm$^{-1}$

EXAMPLE 116

7β-[2-(2-Aminothiazol-4-yl)-2-methoxyiminoacetamido]-3-(3-formamido-2,4-dimethyl-1-pyrazolio)methyl-3-cephem-4-carboxylate (syn isomer)

IR (Nujol): 3300, 1765, 1665, 1600 cm$^{-1}$

EXAMPLE 117

7β-[2-(2-Aminothiazol-4-yl)-2-(difluoromethoxyimino)acetamido]-3-(3-formamido-2-methyl-1-pyrazolio)methyl-3-cephem-4-carboxylate (syn isomer) was obtained from benzhydryl 7β-[2-(2-tritylaminothiazol-4-yl)-2-(difluoromethoxyimino)acetamido]-3-(3-formamido-2-methyl-1-pyrazolio)methyl-3-cephem-4-carboxylate.trifluoroacetate (syn isomer) according to a similar manner to that of Example 45.

IR (Nujol): 3300, 1770, 1665 cm$^{-1}$

NMR (D$_2$O, δ): 3.12 and 3.42 (2H, ABq, J=18 Hz), 3.87 (3H, s), 5.15 and 5.42 (2H, ABq, J=16 Hz), 5.19 (1H, d, J=5 Hz), 5.81 (1H, d, J=5 Hz), 6.75 (1H, d, J=3 Hz), 6.84 (1H, t, J=77 Hz), 7.11 (1H, s), 8.06 (1H, d, J=3 Hz), 8.43 (1H, s)

EXAMPLE 118

7β-[2-(2-Aminothiazol-4-yl)-2-(difluoromethoxyimino)acetamido]-3-(4-formamido-2-methyl-1-pyrazolio)methyl-3-cephem-4-carboxylate (syn isomer) was obtained from benzhydryl 7β-[2-(2-tritylaminothiazol-4-yl)-2-(difluoromethoxyimino)acetamido]-3-(4-formamido-2-methyl-1-pyrazolio)methyl-3-cephem-4-carboxylate.trifluoroacetate (syn isomer) according to a similar manner to that of Example 45.

IR (Nujol): 1775, 1675, 1605 cm$^{-1}$

NMR (D$_2$O, δ): 3.20 and 3.50 (2H, ABq, J=17 Hz), 4.09 (3H, s), 5.22 and 5.50 (2H, ABq, J=15 Hz), 5.23 (1H, d, J=5 Hz), 5.83 (1H, d, J=5 Hz), 6.87 (1H, t, J=77 Hz), 7.13 (1H, s), 8.23 (1H, s), 8.39 (2H, s)

EXAMPLE 119

7β-[2-(2-Aminothiazol-4-yl)-2-(difluoromethoxyimino)acetamido]-3-(3-formamido-2,4-dimethyl-1-pyrazolio)methyl-3-cephem-4-carboxylate (syn isomer) was obtained from benzhydryl 7β-[2-(2-tritylaminothiazol-4-yl)-2-(difluoromethoxyimino)acetamido]-3-(3-formamido-2,4-dimethyl-1-pyrazolio)methyl-3-cephem-4-carboxylate.trifluoroacetate (syn isomer) according to a similar manner to that of Example 45.

IR (Nujol): 3250, 1765, 1665, 1600 cm$^{-1}$

NMR (D$_2$O, δ): 2.03 (3H, s), 3.21 and 3.50 (2H, ABq, J=18 Hz), 3.83 (3H, s), 5.19 and 5.45 (2H, ABq, J=15 Hz), 5.29 (1H, d, J=5 Hz), 5.88 (1H, d, J=5 Hz), 6.93 (1H, t, J=71 Hz), 7.26 (1H, s), 8.07 (1H, s), 8.38 (1H, s)

The following compounds (Examples 120 to 131) were obtained according to a similar manner to that of Example 45.

EXAMPLE 120

7β-[2-(2-Aminothiazol-4-yl)-2-methoxyiminoacetamido]-3-(3-formamido-2-methyl-1-pyrazolio)methyl-3-cephem-4-carboxylate (syn isomer)

IR (Nujol): 3350, 1770, 1660, 1610 cm$^{-1}$

EXAMPLE 121

7β-[2-(2-Aminothiazol-4-yl)-2-methoxyiminoacetamido]-3-(3-amino-2-methyl-1-pyrazolio)methyl-3-cephem-4-carboxylate.trihydrochloride (syn isomer)

IR (Nujol): 3300, 1770, 1660, 1630 cm$^{-1}$

EXAMPLE 122

7β-[2-(2-Aminothiazol-4-yl)-2-(difluoromethoxyimino)acetamido]-3-(3-amino-2-methyl-1-pyrazolio)methyl-3-cephem-4-carboxylate (syn isomer)

IR (Nujol): 3300, 1765, 1660 cm$^{-1}$

EXAMPLE 123

7β-[2-(2-Aminothiazol-4-yl)-2-(difluoromethoxyimino)acetamido]-3-(4-amino-2-methyl-1-pyrazolio)methyl-3-cephem-4-carboxylate (syn isomer)

IR (Nujol): 1760, 1660, 1600 cm$^{-1}$

EXAMPLE 124

7β-[2-(2-Aminothiazol-4-yl)-2-carboxymethoxyiminoacetamido]-3-(3-amino-2-methyl-1-pyrazolio)methyl-3-cephem-4-carboxylate (syn isomer)

IR (Nujol): 3300, 1760, 1650 cm$^{-1}$

EXAMPLE 125

7β-[2-(2-Aminothiazol-4-yl)-2-methoxyiminoacetamido]-3-(2,5-dimethyl-1-pyrazolio)methyl-3-cephem-4-carboxylate (syn isomer)

IR (Nujol): 3300, 1760, 1660, 1605 cm$^{-1}$

EXAMPLE 126

7β-[2-(2-Aminothiazol-4-yl)-2-methoxyiminoacetamido]-3-(3-amino-2,4-dimethyl-1-pyrazolio)methyl-3-cephem-4-carboxylate (syn isomer)

IR (Nujol): 3300, 1770, 1640, 1600 cm$^{-1}$

EXAMPLE 127

7β-[2-(2-Aminothiazol-4-yl)-2-(difluoromethoxyimino)acetamido]-3-(3-amino-2,4-dimethyl-1-pyrazolio)methyl-3-cephem-4-carboxylate (syn isomer)

IR (Nujol): 3300, 1765, 1640, 1600 cm$^{-1}$

EXAMPLE 128

Trifluoroacetic acid salt of 7β-[2-(2-formamidothiazol-4-yl)-2-methoxyiminoacetamido]-3-(2,5-dimethyl-1-pyrazolio)methyl-3-cephem-4-carboxylate (syn isomer)

IR (Nujol): 3350, 1770, 1655 cm$^{-1}$

EXAMPLE 129

Trifluoroacetic acid salt of 7β-[2-(2-formamidothiazol-4-yl)-2-methoxyiminoacetamido]-3-(3-formamido-2,4-dimethyl-1-pyrazolio)methyl-3-cephem-4-carboxylate (syn isomer)

IR (Nujol): 3300, 1780, 1650 cm$^{-1}$

EXAMPLE 130

7β-[2-(2-Aminothiazol-4-yl)-2-methoxyiminoacetamido]-3-(4-formamido-2-methyl-1-pyrazolio)methyl-3-cephem-4-carboxylate (syn isomer)

IR (Nujol): 3300, 1770, 1665, 1605 cm$^{-1}$

EXAMPLE 131

7β-[2-(2-Aminothiazol-4-yl)-2-methoxyiminoacetamido]-3-(3-formamido-2,4-dimethyl-1-pyrazolio)methyl-3-cephem-4-carboxylate (syn isomer)

IR (Nujol): 3300, 1765, 1665, 1600 cm$^{-1}$

EXAMPLE 132

Concentrated hydrochloric acid (0.136 ml) was added to a suspension of 7β-[2-(2-aminothiazol-4-yl)-2-methoxyiminoacetamido]-3-(3-formamido-2-methyl-1-pyrazolio)methyl-3-cephem-4-carboxylate (syn isomer) (0.2 g) in methanol (1 ml) at ambient temperature. After being stirred at the same temperature for 3 hours, the mixture was added dropwise to diethyl ether (100 ml), and the precipitate was collected by filtration. The precipitate was dissolved in water and subjected to column chromatography on macroporous non-ionic adsorption resin "Diaion HP-20". The desired product was eluted with water, and lyophilized to give 7β-[2-(2-aminothiazol-4-yl)-2-methoxyiminoacetamido]-3-(3-amino-2-methyl-1-pyrazolio)methyl-3-cephem-4-carboxylate.trihydrochloride (syn isomer) (71.20 mg).

IR (Nujol): 3300, 1770, 1660, 1630 cm$^{-1}$

NMR (D$_2$O, δ): 3.17 and 3.43 (2H, ABq, J=18 Hz), 3.66 (3H, s), 4.03 (3H, s), 5.18 (2H, broad s), 5.21 (1H, d, J=5 Hz), 5.78 (1H, d, J=5 Hz), 5.92 (1H, d, J=3 Hz), 7.08 (1H, s), 7.79 (1H, d, J=3 Hz)

EXAMPLE 133

7β-[2-(2-Aminothiazol-4-yl)-2-methoxyiminoacetamido]-3-(3-amino-2,4-dimethyl-1-pyrazolio)methyl-3-cephem-4-carboxylate (syn isomer) was obtained from trifluoroacetic acid salt of 7β-[2-(2-aminothiazol-4-yl)-2-methoxyiminoacetamido]-3-(3-formamido-2,4-dimethyl-1-pyrazolio)methyl-3-cephem-4-carboxylate (syn isomer) according to a similar manner to that of Example 132.

IR (Nujol): 3300, 1770, 1640, 1600 cm$^{-1}$

NMR (D$_2$O, δ): 1.93 (3H, s), 3.08 and 3.33 (2H, ABq, J=18 Hz), 3.65 (3H, s), 3.98 (3H, s), 4.88 and 5.21 (2H, ABq, J=15 Hz), 5.18 (1H, d, J=5 Hz), 5.81 (1H, d, J=5 Hz), 6.97 (1H, s), 7.66 (1H, s)

The following compounds (Examples 134 to 136) were obtained according to a similar manner to that of Example 132.

EXAMPLE 134

7β-[2-(2-Aminothiazol-4-yl)-2-(difluoromethoxyimino)acetamido]-3-(3-amino-2-methyl-1-pyrazolio)-methyl-3-cephem-4-carboxylate (syn isomer)

IR (Nujol): 3300, 1765, 1660 cm$^{-1}$

NMR (DMSO-d$_6$, δ): 2.94 and 3.22 (2H, ABq, J=18 Hz), 3.68 (3H, s), 4.96 and 5.27 (2H, ABq, J=15 Hz), 5.00 (1H, d, J=5 Hz), 5.57 (1H, dd, J=8 Hz and 5 Hz), 5.75 (1H, d, J=3 Hz), 6.90 (1H, s), 7.01 (1H, t, J=77 Hz), 7.26 (2H, broad s), 8.01 (1H, d, J=3 Hz), 9.76 (1H, d, J=8 Hz)

EXAMPLE 135

7β-[2-(2-Aminothiazol-4-yl)-2-(difluoromethoxyimino)acetamido]-3-(4-amino-2-methyl-1-pyrazolio)-methyl-3-cephem-4-carboxylate (syn isomer)

IR (Nujol): 1760, 1660, 1600 cm$^{-1}$

NMR (D$_2$O, δ): 3.13 and 3.43 (2H, ABq, J=18 Hz), 3.93 (3H, s), 5.06 and 5.34 (2H, ABq, J=15 Hz), 5.18 (1H, d, J=5 Hz), 5.76 (1H, d, J=5 Hz), 6.86 (1H, t, J=77 Hz), 7.13 (1H, s), 7.70 (2H, s)

EXAMPLE 136

7β-[2-(2-Aminothiazol-4-yl)-2-carboxymethoxyiminoacetamido]-3-(3-amino-2-methyl-1-pyrazolio)-methyl-3-cephem-4-carboxylate (syn isomer)

IR (Nujol): 3300, 1760, 1650 cm$^{-1}$

EXAMPLE 137

7β-[2-(2-Aminothiazol-4-yl)-2-(difluoromethoxyimino)acetamido]-3-(3-amino-2,4-dimethyl-1-pyrazolio)methyl-3-cephem-4-carboxylate (syn isomer) (432.3 mg) was obtained by reacting 7β-[2-(2-aminothiazol-4-yl)-2-(difluoromethoxyimino)acetamido]-3-(3-formamido-2,4-dimethyl-1-pyrazolio)methyl-3-cephem-4-carboxylate (syn isomer) (923 mg) with concentrated hydrochloric acid (0.57 ml) in methanol (5 ml) according to a similar manner to that of Example 132.

IR (Nujol): 3300, 1765, 1640, 1600 cm$^{-1}$

NMR (D$_2$O, δ): 1.93 (3H, s), 3.08 and 3.31 (2H, ABq, J=18 Hz), 3.64 (3H, s), 4.88 and 5.23 (2H, ABq, J=15 Hz), 5.19 (1H, d, J=5 Hz), 5.83 (1H, d, J=5 Hz), 6.90 (1H, t, J=78 Hz), 7.19 (1H, s), 7.66 (1H, s)

EXAMPLE 138

To a suspension of 7β-[2-(2-aminothiazol-4-yl)-2-tert-butoxycarbonylmethoxyiminoacetamido]-3-(3-amino-2-methyl-1-pyrazolio)methyl-3-cephem-4-carboxylate trihydrochloride (syn isomer) (1.2 g) in anisole (1.2 ml) and methylene chloride (3.6 ml) was added dropwise trifluoroacetic acid (2.4 ml) under ice-cooling. After being stirred at ambient temperature for 3 hours, the mixture was added dropwise to isopropyl ether (200 ml). The resultant precipitate was collected by filtration. The precipitate was dissolved in water (30 ml) and the solution was adjusted to pH 2 with 5% aqueous sodium bicarbonate solution, and then subjected to column chromatography on macroporous non-ionic adsorption resin "Diaion HP-20". The desired product was eluted with 5% aqueous isopropyl alcohol solution, and isopropyl alcohol was evaporated. The aqueous layer was lyophilized to give 7β-[2-(2-aminothiazol-4-yl)-2-carboxymethoxyiminoacetamido]-3-(3-amino-2-methyl-1-pyrazolio)methyl-3-cephem-4-carboxylate (syn isomer) (131.3 mg).

IR (Nujol): 3300, 1760, 1650 cm$^{31}$ $^1$

NMR (D$_2$O, δ): 3.16 and 3.32 (2H, ABq, J=18 Hz), 3.62 (3H, s), 4.51 (2H, s), 4.93 and 5.21 (2H, ABq, J=15 Hz), 5.14 (1H, d, J=5 Hz), 5.78 (1H, d, J=5 Hz), 5.87 (1H, d, J=3 Hz) 6.95 (1H, s), 7.77 (1H, d, J=3 Hz)

EXAMPLE 139

To a suspension of Vilsmeier reagent prepared from N,N-dimethylformamide (0.158 ml) and phosphoryl chloride (0.187 ml) in tetrahydrofuran (1 ml) was added a solution of 4-chloro-2-difluoromethoxyimino-3-oxobutyric acid (0.4 g) in tetrahydrofuran (4 ml) under ice-cooling with stirring. After stirred at the same temperature for 30 minutes, this activated acid solution was added to a solution of bis(trifluoroacetic acid) salt of 7β-amino-3-(2-methyl-1-pyrazolio)methyl-3-cephem-4-carboxylate (0.80 g) and N-(trimethylsilyl)acetamide (2.9 g) in tetrahydrofuran (20 ml) under ice-cooling. The mixture was stirred at the same temperature for 1.5 hours. To the resultant mixture was added a solution of thiourea (230 mg) in N,N-dimethylacetamide (2.3 ml) at ambient temperature. After stirred at 30°-35° C. for 4 hours, the resultant solution was poured into a mixture of n-hexane (30 ml) and diisopropyl ether (50 ml). The precipitated mass was triturated in ethyl acetate and dried under reduced pressure. The dried glassy mass was dissolved in water (20 ml) and the aqueous solution was washed with ethyl acetate twice, adjusted to pH 2.0 with 5% aqueous sodium bicarbonate solution, and subjected to column chromatography on macroporous nonionic adsorption resin "Diaion HP-20". The column was washed with water and the object compound was eluted with 30% aqueous methanol. The fraction containing the object compound was concentrated under reduced pressure and the residue was lyophilized to give 7β-[2-(2-aminothiazol-4-yl)-2-(difluoromethoxyimino)acetamido]-3-(2-methyl-1-pyrazolio)methyl-3-cephem-4-carboxylate (syn isomer) (0.25 g).

IR (Nujol): 3400, 1770, 1660, 1600, 1530 cm$^{-1}$

NMR (D$_2$O, δ): 3.20 and 3.50 (2H, ABq, J=18 Hz), 4.10 (3H, s), 5.25 (1H, d, J=5 Hz), 5.25 and 5.50 (2H, ABq, J=14 Hz), 5.85 (1H, d, J=5 Hz), 6.75 (1H, t, J=72 Hz), 7.20 (1H, s), 8.17 (2H, m)

EXAMPLE 140

4-Chloro-2-methoxyimino-3-oxobutyric acid, which was obtained in advance from tert-butyl 2-methoxyimino3-phenyliminobutyrate according to a similar manner to that of Preparation 27, was reacted with 7β-amino-3-(2-methyl-1-pyrazolio)methyl-3-cephem-4-carboxylate according to a similar manner to that of Example 139 to give 7β-[2-(2-aminothiazol-4-yl)-2-methoxyiminoacetamido]-3-(2-methyl-1-pyrazolio)-methyl-3-cephem-4-carboxylate (syn isomer).

IR (Nujol): 1775, 1660, 1600 cm$^{-1}$

The following compounds (Examples 141 to 177) were obtained according to a similar manner to that of Example 139.

EXAMPLE 141

Trifluoroacetic acid salt of 7β-[2-(2-formamidothiazol-4-yl)-2-methoxyiminoacetamido]-3-(2-methyl-1-pyrazolio)methyl-3-cephem-4-carboxylate (syn isomer).

IR (Nujol): 1785, 1675 cm$^{-1}$

EXAMPLE 142

7β-[2-(2-Aminothiazol-4-yl)-2-(3-thietanyloxyimino)acetamido]-3-(2-methyl-1-pyrazolio)methyl-3-cephem-4-carboxylate (syn isomer).

IR (Nujol): 1770, 1660, 1605 cm$^{-1}$

EXAMPLE 143

Trifluoroacetic acid salt of 7β-[2-(2-formamidothiazol-4-yl)-2-isopropoxyiminoacetamido]-3-(2-methyl-1-pyrazolio)methyl-3-cephem-4-carboxylate (syn isomer)
IR (Nujol): 3400, 1770, 1650 cm$^{-1}$

EXAMPLE 144

Trifluoroacetic acid salt of 7β-[2-(2-cyclopenten-1-yloxyimino)-2-(2-formamidothiazol-4-yl)acetamido]-3-(2,5-dimethyl-1-pyrazolio)methyl-3-cephem-4-carboxylate (syn isomer)
IR (Nujol): 3350, 1770, 1670 cm$^{-1}$

EXAMPLE 145

Trifluoroacetic acid salt of 7β-[2-(2-tetrahydropyranyloxyimino)-2-(2-tritylaminothiazol-4-yl)acetamido]-3-(2-methyl-1-pyrazolio)methyl-3-cephem-4-carboxylate (syn isomer)
IR (Nujol): 3300, 3150, 1775, 1675 cm$^{-1}$

EXAMPLE 146

Trifluoroacetic acid salt of 7β-[2-difluoromethoxyimino-2-(2-tritylaminothiazol-4-yl)acetamido]-3-(2,5-dimethyl-1-pyrazolio)methyl-3-cephem-4-carboxylate (syn isomer)
IR (Nujol): 1780, 1660 cm$^{-1}$

EXAMPLE 147

7β-[2-(2-Aminothiazol-4-yl)-2-(2-cyclopenten-1-yloxyimino)acetamido]-3-(2-methyl-1-pyrazolio)methyl-3-cephem-4-carboxylate (syn isomer)
IR (Nujol): 3300, 1770, 1650, 1610, 1530 cm$^{-1}$

EXAMPLE 148

7β-[2-(2-Aminothiazol-4-yl)-2-isopropoxyiminoacetamido]-3-(2-methyl-1-pyrazolio)methyl-3-cephem-4-carboxylate (syn isomer)
IR (Nujol): 3300, 1770, 1660, 1610, 1530 cm$^{-1}$

EXAMPLE 149

7β-[2-(2-Aminothiazol-4-yl)-2-(2-tetrahydropyranyloxyimino)acetamido]-3-(2-methyl-1-pyrazolio)methyl-3-cephem-4-carboxylate (syn isomer)
IR (Nujol): 3300, 1775, 1680, 1620 cm$^{-1}$

EXAMPLE 150

7β-[2-(2-Aminothiazol-4-yl)-2-(2-cyclopenten-1-yloxyimino)acetamido]-3-(2,5-dimethyl-1-pyrazolio)methyl-3-cephem-4-carboxylate (syn isomer)
IR (Nujol): 3300, 1770, 1660, 1600 cm$^{-1}$

EXAMPLE 151

7β-[2-(2-Aminothiazol-4-yl)-2-(hydroxyimino)acetamido]-3-(2-methyl-1-pyrazolio)methyl-3-cephem-4-carboxylate (syn isomer)
IR (Nujol): 3320, 1775, 1660, 1620, 1600 cm$^{-1}$

EXAMPLE 152

7β-[2-(2-Aminothiazol-4-yl)-2-(difluoromethoxyimino)acetamido]-3-(2,5-dimethyl-1-pyrazolio)methyl-3-cephem-4-carboxylate (syn isomer)
IR (Nujol): 3300, 1770, 1670, 1610 cm$^{-1}$

EXAMPLE 153

7β-[2-(2-Aminothiazol-4-yl)-2-(3-cyclopenten-1-yloxyimino)acetamido]-3-(2-methyl-1-pyrazolio)methyl-3-cephem-4-carboxylate (syn isomer)
IR (Nujol): 3250, 3100, 1770, 1662, 1608 cm$^{-1}$

EXAMPLE 154

7β-[2-(2-Aminothiazol-4-yl)-2-(2-cyclopenten-1-yloxyimino)acetamido]-3-(4-hydroxymethyl-2-methyl-1-pyrazolio)methyl-3-cephem-4-carboxylate (syn isomer)
IR (Nujol): 3260, 1765, 1660, 1605 cm$^{-1}$

EXAMPLE 155

7β-[2-(2-Aminothiazol-4-yl)-2-(hydroxyimino)acetamido]-3-(4-hydroxymethyl-2-methyl-1-pyrazolio)methyl-3-cephem-4-carboxylate (syn isomer)
IR (Nujol): 3200, 1765, 1660, 1600 cm$^{-1}$

EXAMPLE 156

Sulfuric acid salt of 7β-[2-(2-aminothiazol-4-yl)-2-(difluoromethoxyimino)acetamido]-3-(2-methyl-1-pyrazolio)methyl-3-cephem-4-carboxylate (syn isomer)
NMR (D$_2$O, δ): 3.33 and 3.57 (2H, ABq, J=18 Hz), 4.15 (3H, s), 5.30 (1H, d, J=5 Hz), 5.47 (2H, br. s), 5.87 (1H, d, J=5 Hz), 6.73–6.90 (1H, m), 7.0 (1H, t, J=71 Hz), 7.40 (1H, s), 8.20–8.35 (2H, m)

EXAMPLE 157

7β-[2-(2-Tritylaminothiazol-4-yl)-2-methoxyiminoacetamido]-3-(3-formamido-2-methyl-1-pyrazolio)methyl-3-cephem-4-carboxylate (syn isomer)
IR (Nujol): 3350, 1775, 1660, 1580 cm$^{-1}$

EXAMPLE 158

7β-[2-(2-Formamidothiazol-4-yl)-2-tert-butoxycarbonylmethoxyiminoacetamido]-3-(3-formamido-2-methyl-1-pyrazolio)methyl-3-cephem-4-carboxylate (syn isomer)
IR (Nujol): 1770, 1670, 1605 cm$^{-1}$

EXAMPLE 159

7β-[2-(2-Aminothiazol-4-yl)-2-methoxyiminoacetamido]-(3-formamido-2-methyl-1-pyrazolio)methyl-3-cephem-4-carboxylate (syn isomer)
IR (Nujol): 3350, 1770, 1660, 1610 cm$^{-1}$

EXAMPLE 160

7β-[2-(2-Aminothiazol-4-yl)-2-(difluoromethoxyimino)acetamido]-3-(4-formamido-2-methyl-1-pyrazolio)methyl-3-cephem-4-carboxylate (syn isomer)
IR (Nujol): 1775, 1675, 1605 cm$^{-1}$

EXAMPLE 161

7β-[2-(2-Aminothiazol-4-yl)-2-(difluoromethoxyimino)acetamido]-3-(3-formamido-2-methyl-1-pyrazolio)methyl-3-cephem-4-carboxylate (syn isomer)
IR (Nujol): 3300, 1770, 1665 cm$^{-1}$

EXAMPLE 162

7β-[2-(2-Aminothiazol-4-yl)-2-methoxyiminoacetamido]-(3-amino-2-methyl-1-pyrazolio)-methyl-3-cephem-4-carboxylate.trihydrochloride (syn isomer)
IR (Nujol): 3300, 1770, 1660, 1630 cm$^{-1}$

EXAMPLE 163

7β-[2-(2-Aminothiazol-4-yl)-2-(difluoromethoxyimino)acetamido]-3-(3-amino-2-methyl-1-pyrazolio)methyl-3-cephem-4-carboxylate (syn isomer)
IR (Nujol): 3300, 1765, 1660 cm$^{-1}$

EXAMPLE 164

7β-[2-(2-Aminothiazol-4-yl)-2-(difluoromethoxyimino)acetamido]-3-(4-amino-2-methyl-1-pyrazolio)methyl-3-cephem-4-carboxylate (syn isomer)
IR (Nujol): 1760, 1660, 1600 cm$^{-1}$

EXAMPLE 165

7β-[2-(2-Aminothiazol-4-yl)-2-tert-butoxycarbonylmethoxyiminoacetamido]-3-(3-amino-2-methyl-1-pyrazolio)methyl-3-cephem-4-carboxylate.trihydrochloride (syn isomer)
IR (Nujol): 3300, 1775, 1715, 1670, 1630 cm$^{-1}$

EXAMPLE 166

Benzhydryl 7β-[2-(2-tritylaminothiazol-4-yl)-2-(difluoromethoxyimino)acetamido]-3-(4-formamido-2-methyl-1-pyrazolio)methyl-3-cephem-4-carboxylate trifluoroacetate (syn isomer)
IR (Nujol): 1795, 1725, 1675, 1615 cm$^{-1}$

EXAMPLE 167

Benzhydryl 7β-[2-(2-tritylaminothiazol-4-yl)-2-(difluoromethoxyimino)acetamido]-3-(3-formamido-2-methyl-1-pyrazolio)methyl-3-cephem-4-carboxylate.trifluoroacetate (syn isomer)
IR (Nujol): 3200, 1790, 1720, 1680 cm$^{-1}$

EXAMPLE 168

7β-[2-(2-Aminothiazol-4-yl)-2-carboxymethoxyiminoacetamido]-3-(3-amino-2-methyl-1-pyrazolio)methyl-3-cephem-4-carboxylate (syn isomer)
IR (Nujol): 3300, 1760, 1650 cm$^{-1}$

EXAMPLE 169

7β-[2-(2-Aminothiazol-4-yl)-2-methoxyiminoacetamido]-3-(2,5-dimethyl-1-pyrazolio)methyl-3-cephem-4-carboxylate (syn isomer)
IR (Nujol): 3300, 1760, 1660, 1605 cm$^{-1}$

EXAMPLE 170

7β-[2-(2-Aminothiazol-4-yl)-2-methoxyiminoacetamido]-3-(3-amino-2,4-dimethyl-1-pyrazolio)methyl-3-cephem-4-carboxylate (syn isomer)
IR (Nujol): 3300, 1770, 1640, 1600 cm$^{-1}$

EXAMPLE 171

Benzhydryl 7β-[2-(2-tritylaminothiazol-4-yl)-2-(difluoromethoxyimino)acetamido]-3-(3-formamido-2,4-dimethyl-1-pyrazolio)methyl-3-cephem-4-carboxylate trifluoroacetate (syn isomer)
IR (Nujol): 1785, 1720, 1675 cm$^{-1}$

EXAMPLE 172

7β-[2-(2-Aminothiazol-4-yl)-2-(difluoromethoxyimino)acetamido]-3-(3-formamido-2,4-dimethyl-1-pyrazolio)methyl-3-cephem-4-carboxylate (syn isomer)
IR (Nujol): 3250, 1765, 1665, 1600 cm$^{-1}$

EXAMPLE 173

7β-[2-(2-Aminothiazol-4-yl)-2-(difluoromethoxyimino)acetamido]-3-(3-amino-2,4-dimethyl-1-pyrazolio)methyl-3-cephem-4-carboxylate (syn isomer)
IR (Nujol): 3300, 1765, 1640, 1600 cm$^{-1}$

EXAMPLE 174

Trifluoroacetic acid salt of 7β-[2-(2-formamidothiazol-4-yl)-2-methoxyiminoacetamido]-3-(2,5-dimethyl-1-pyrazolio)methyl-3-cephem-4-carboxylate (syn isomer)
IR (Nujol): 3350, 1770, 1655 cm$^{-1}$

EXAMPLE 175

Trifluoroacetic acid salt of 7β-[2-(2-formamidothiazol-4-yl)-2-methoxyiminoacetamido]-3-(3-formamido-2,4-dimethyl-1-pyrazolio)methyl-3-cephem-4-carboxylate (syn isomer)
IR (Nujol): 3300, 1780, 1650 cm$^{-1}$

EXAMPLE 176

7β-[2-(2-Aminothiazol-4-yl)-2-methoxyiminoacetamido]-3-(4-formamido-2-methyl-1-pyrazolio)methyl-3-cephem-4-carboxylate (syn isomer)
IR (Nujol): 3300, 1770, 1665, 1605 cm$^{-1}$

EXAMPLE 177

7β-[2-(2-Aminothiazol-4-yl)-2-methoxyiminoacetamido]-3-(3-formamido-2,4-dimethyl-1-pyrazolio)methyl-3-cephem-4-carboxylate (syn isomer)
IR (Nujol): 3300, 1765, 1665, 1600 cm$^{-1}$ The following compounds (Examples 178 to 185) were obtained according to a similar manner to that of Example 1.

EXAMPLE 178

Benzhydryl 7β-[2-(2-aminothiazol-4-yl)-2-(2-cyclopenten-1-yloxyimino)acetamido]-3-[2-methyl-1-pyrazolio)methyl-3-cephem-4-carboxylate chloride (syn isomer)
IR (Nujol): 3300, 1785, 1720, 1670, 1620, 1530 cm$^{-1}$

EXAMPLE 179

Benzhydryl 7β-[2-(2-aminothiazol-4-yl)-2-(2-cyclopenten-1-yloxyimino)acetamido]-3-(4-hydroxymethyl-2-methyl-1-pyrazolio)methyl-3-cephem-4-carboxylate chloride (syn isomer).
IR (Nujol): 1785, 1720, 1675, 1630 cm$^{-1}$

EXAMPLE 180

Benzhydryl 7β-[2-(2-aminothiazol-4-yl)-2-(2-cyclopenten-1-yloxyimino)acetamido]-3-(4-methoxy-2-methyl-1-pyrazolio)methyl-3-cephem-4-carboxylate trifluoroacetate (syn isomer).
IR (Nujol): 1780, 1720, 1670, 1625, 1600 cm$^{-1}$

EXAMPLE 181

Benzhydryl 7β-[2-(2-cyclopenten-1-yloxyimino)-2-(2-formamidothiazol-4-yl)acetamido]-3-(4-hydroxymethyl-2-methyl-1-pyrazolio)methyl-3-cephem-4-carboxylate trifluoroacetate (syn isomer).
IR (Nujol): 1785, 1720, 1685, 1670 cm$^{-1}$

EXAMPLE 182

Benzhydryl 7β-[2-(2-tritylaminothiazol-4-yl)-2-difluoromethoxyiminoacetamido]-3-(4-methoxy-2-methyl-1-pyrazolio)methyl-3-cephem-4-carboxylate trifluoroacetate (syn isomer).
IR (Nujol): 1790, 1720, 1685, 1605 cm$^{-1}$

EXAMPLE 183

Benzhydryl 7β-[2-(2-formamidothiazol-4-yl)-2-(2-cyclopenten-1-yloxyimino)acetamido]-3-(4-methoxy-2-methyl-1-pyrazolio)methyl-3-cephem-4-carboxylate trifluoroacetate (syn isomer).
IR (Nujol): 1785, 1720, 1680, 1600 cm$^{-1}$

EXAMPLE 184

Benzhydryl 7β-[2-(2-cyclopenten-1-yloxyimino)-2-(2-formamidothiazol-4-yl)acetamido]-3-(2-methyl-1- pyrazolio)methyl-3-cephem-4-carboxylate iodide (syn isomer).

IR (Nujol): 3300, 1780, 1720, 1670, 1540 cm$^{-1}$

EXAMPLE 185

Benzhydryl 7β-[2-(2-cyclopenten-1-yloxyimino)-2-(2-formamidothiazol-4-yl)acetamido]-3-(2-methyl-1-pyrazolio)methyl-3-cephem-4-carboxylate trifluoroacetate (syn isomer).

IR (Nujol): 3200, 1780, 1720, 1670, 1540 cm$^{-1}$

EXAMPLE 186

To a mixture of benzhydryl 7β-[2-(2-cyclopenten-1-yloxyimino)-2-(2-formamidothiazol-4-yl)acetamido]-3-(2-methyl-1-pyrazolio)methyl-3-cephem-4-carboxylate trifluoroacetate (syn isomer, 4.9 g) in a mixture of methanol (50 ml) and tetrahydrofuran (10 ml) was added conc. hydrochloric acid (2.13 g) and the mixture was stirred at ambient temperature for 3 hours. Water (50 ml) and ethyl acetate (50 ml) were added thereto and the mixture was adjusted to pH 7.0 with 5% aqueous solution of sodium bicarbonate. The separated organic layer was washed with brine, dried over magnesium sulfate and evaporated to give benzhydryl 7β-[2-(2-aminothiazol-4-yl)-2-(2-cyclopenten-1-yloxyimino)acetamido]-3-(2-methyl-1-pyrazolio)methyl-3-cephem-4-carboxylate chloride (syn isomer, 3.66 g).

IR (Nujol): 3300, 1785, 1720, 1670, 1620, 1530 cm$^{-1}$

NMR (DMSO-d$_6$, δ): 2.00 (2H, m), 2.32 (2H, m), 3.50 (2H, m), 3.85 (3H, s), 5.28 (1H, d, J=5 Hz), 5.30–6.32 (5H, m), 6.73 (1H, s), 6.87 (1H, t, J=2 Hz), 6.95 (1H, s), 7.42 (10H, m), 8.45 (1H, d, J=2 Hz), 7.55 (1H, d, J=2 Hz), 9.58 (1H, d, J=8 Hz)

EXAMPLE 187

Benzhydryl 7β-[2-(2-aminothiazol-4-yl)-2-(2-cyclopenten-1-yloxyimino)acetamido]-3-(4-hydroxymethyl-2-methyl-1-pyrazolio)methyl-3-cephem-4-carboxylate chloride (syn isomer) was obtained according to a similar manner to that of Example 186.

IR (Nujol): 1785, 1720, 1675, 1630 cm$^{-1}$

NMR (DMSO-d$_6$, δ): 1.82–2.48 (4H, m), 3.48 (2H, br. s), 3.83 (3H, s), 4.49 (2H, s), 5.28 (1H, d, J=5 Hz), 5.30 (1H, m), 5.48 (2H, br. s), 5.90–6.18 (2H, m), 5.93 (1H, dd, J=8 Hz, 5 Hz), 6.86 (1H, s), 6.91 (1H, s), 7.18–7.57 (10H, m), 8.33 (1H, s), 8.43 (1H, s), 9.74 (1H, d, J=8 Hz).

EXAMPLE 188

Benzhydryl 7β-[2-(2-aminothiazol-4-yl)-2-(2-cyclopenten-1-yloxyimino)acetamido]-3-(4-methoxy-2-methyl-1-pyrazolio)methyl-3-cephem-4-carboxylate trifluoroacetate (syn isomer) was obtained according to a similar manner to that of Example 186.

IR (Nujol): 1780, 1720, 1670, 1625, 1600 cm$^{-1}$

NMR (DMSO-d$_6$, δ): 1.72–2.53 (4H, m), 3.50 (2H, br. s), 3.79 (6H, s), 5.28 (1H, d, J=5 Hz), 5.30 (1H, m), 5.47 (2H, br s), 5.80–6.18 (3H, m), 6.86 (1H, s), 6.91 (1H, s), 7.12–7.56 (10H, m), 8.33 (1H, s), 8.44 (1H, s), 9.68 (1H, d, J=8 Hz)

EXAMPLE 189

4-Hydroxymethyl-1-methylpyrazole (2.5 ml) was added to a solution of benzhydryl 7β-[2-(2-cyclopenten-1-yloxyimino)-2-(2-formamidothiazol-4-yl)acetamido]-3-chloromethyl-3-cephem-4-carboxylate (syn isomer, 2.5 g) and sodium iodide (0.553 g) in acetone (2.5 ml) at ambient temperature. After stirring for 12 hours, the reaction mixture was poured into a mixture of ethyl acetate, tetrahydrofuran and water. The separated organic layer was washed with brine, dried over magnesium sulfate, and evaporated. The residue was dissolved in tetrahydrofuran, and the solution was subjected to column chromatography on Amberlite IRA-400 (CF$_3$COO$^\ominus$ form), and eluted with tetrahydrofuran. The fractions containing the object compound were collected and evaporated to give benzhydryl 7β-[2-(2-cyclopenten-1-yloxyimino)-2-(2-formamidothiazol-4-yl)acetamido]-3-(4-hydroxymethyl-2-methyl-1-pyrazolio)methyl-3-cephem-4-carboxylate trifluoroacetate (syn isomer, 2.25 g).

IR (Nujol): 1785, 1720, 1685, 1670 cm$^{-1}$

NMR (DMSO-d$_6$, δ): 1.87–2.52 (4H, m), 3.83 (2H, s), 3.82 (3H, s), 4.42 (2H, s), 5.28 (1H, d, J=5 Hz), 5.30 (1H, m), 5.43 (2H, br. s), 5.87 (1H, dd, J=8 Hz, 5 Hz), 5.88–6.18 (2H, m), 6.93 (1H, s), 7.18–7.52 (11H, m), 8.26 (1H, s), 8.40 (1H, s), 8.48 (1H, s), 9.64 (1H, d, J=8 Hz)

The following compounds (Examples 190 to 198) were obtained according to a similar manner to that of Example 189.

EXAMPLE 190

Benzhydryl 7β-[2-(2-tritylaminothiazol-4-yl)-2-difluoromethoxyiminoacetamido]-3-(4-methoxy-2-methyl-1-pyrazolio)methyl-3-cephem-4-carboxylate trifluoroacetate (syn isomer)

IR (Nujol): 1790, 1720, 1685, 1605 cm$^{-1}$

NMR (DMSO-d$_6$, δ): 3.49 and 3.76 (2H, ABq, J=18 Hz), 3.74 (6H, s), 5.19 (1H, d, J=5 Hz), 5.24 and 5.49 (2H, ABq, J=16 Hz), 5.77 (1H, dd, J=8 Hz, 5 Hz), 6.86 (1H, s), 6.92 (1H, s), 6.97 (1H, t, J=79 Hz), 7.01–7.56 (25H, m), 8.13 (1H, s), 8.31 (1H, s), 8.83 (1H, s), 9.78 (1H, d, J=8 Hz)

EXAMPLE 191

Benzhydryl 7β-[2-(2-formamidothiazol-4-yl)-2-(2-cyclopenten-1-yloxyimino)acetamido]-3-(4-methoxy-2-methyl-1-pyrazolio)methyl-3-cephem-4-carboxylate trifluoroacetate (syn isomer)

IR (Nujol): 1785, 1720, 1680, 1600 cm$^{-1}$

NMR (DMSO-d$_6$, δ): 1.72–2.50 (4H, m), 3.40 (2H, br. s), 3.73 (3H, s), 3.77 (3H, s), 5.10–5.51 (3H, m), 5.22 (1H, d, J=5 Hz), 5.75–6.12 (3H, m), 6.87 (1H, s), 7.10–7.52 (11H, m), 8.13 (1H, s), 8.31 (1H, s), 8.42 (1H, s), 9.55 (1H, d, J=8 Hz).

EXAMPLE 192

Benzhydryl 7β-[2-(2-aminothiazol-4-yl)-2-(2-cyclopenten-1-yloxyimino)acetamido]-3-(2-methyl-1-pyrazolio)methyl-3-cephem-4-carboxylate chloride (syn isomer).

IR (Nujol): 3300, 1785, 1720, 1670, 1620, 1530 cm$^{-1}$

EXAMPLE 193

Benzhydryl 7β-[2-(2-aminothiazol-4-yl)-2-(2-cyclopenten-1-yloxyimino)acetamido]-3-(4-hydroxymethyl-2-methyl-1-pyrazolio)methyl-3-cephem-4-carboxylate chloride (syn isomer).

IR (Nujol): 1785, 1720, 1675, 1630 cm$^{-1}$

EXAMPLE 194

Benzhydryl 7β-[2-(2-aminothiazol-4-yl)-2-(2-cyclopenten-1-yloxyimino)acetamido]-3-(4-methoxy-2-methyl-1-pyrazolio)methyl-3-cephem-4-carboxylate trifluoroacetate (syn isomer)

IR (Nujol): 1780, 1720, 1670, 1625, 1600 cm$^{-1}$

EXAMPLE 195

Benzhydryl 7β-[2-(2-cyclopenten-1-yloxyimino)-2-(2-formamidothiazol-4-yl)acetamido]-3-(2-methyl-1-pyrazolio)methyl-3-cephem-4-carboxylate iodide (syn isomer).

IR (Nujol): 3300, 1780, 1720, 1670, 1540 cm$^{-1}$

EXAMPLE 196

Benzhydryl 7β-[2-(2-cyclopenten-1-yloxyimino)-2-(2-formamidothiazol-4-yl)acetamido]-3-(2-methyl-1-pyrazolio)methyl-3-cephem-4-carboxylate trifluoroacetate (syn isomer).

IR (Nujol): 3200, 1780, 1720, 1670, 1540 cm$^{-1}$

EXAMPLE 197

7β-[2-(2-Aminothiazol-4-yl)-2-hydroxyiminoacetamido]-3-(4-methoxy-2-methyl-1-pyrazolio)-methyl-3-cephem-4-carboxylate (syn isomer).

IR (Nujol): 3250, 1765, 1660, 1600 cm$^{-1}$

EXAMPLE 198

7β-[2-(2-Aminothiazol-4-yl)-2-(2-cyclopenten-1-yloxyimino)acetamido]-3-(4-methoxy-2-methyl-1-pyrazolio)methyl-3-cephem-4-carboxylate (syn isomer).

IR (Nujol): 3300, 1675, 1605 cm$^{-1}$

The following compounds (Examples 199 to 208) were obtained according to a similar manner to that of Example 139.

EXAMPLE 199

Benzhydryl 7β-[2-(2-aminothiazol-4-yl)-2-(2-cyclopenten-1-yloxyimino)acetamido]-3-(2-methyl-1-pyrazolio)methyl-3-cephem-4-carboxylate chloride (syn isomer).

IR (Nujol): 3300, 1785, 1720, 1670, 1620, 1530 cm$^{-1}$

EXAMPLE 200

Benzhydryl 7β-[2-(2-aminothiazol-4-yl)-2-(2-cyclopenten-1-yloxyimino)acetamido]-3-(4-hydroxymethyl-2-methyl-1-pyrazolio)methyl-3-cephem-4-carboxylate chloride (syn isomer).

IR (Nujol): 1785, 1720, 1675, 1630 cm$^{-1}$

EXAMPLE 201

Benzhydryl 7β-[2-(2-aminothiazol-4-yl)-2-(2-cyclopenten-1-yloxyimino)acetamido]-3-(4-methoxy-2-methyl-1-pyrazolio)methyl-3-cephem-4-carboxylate trifluoroacetate (syn isomer).

IR (Nujol): 1780, 1720, 1670, 1625, 1600 cm$^{-1}$

EXAMPLE 202

Benzhydryl 7β-[2-(2-cyclopenten-1-yloxyimino)-2-(2-formamidothiazol-4-yl)acetamido]-3-(4-hydroxymethyl-2-methyl-1-pyrazolio)methyl-3-cephem-4-carboxylate trifluoroacetate (syn isomer).

IR (Nujol): 1785, 1720, 1685, 1670 cm$^{-1}$

EXAMPLE 203

Benzhydryl 7β-[2-(2-tritylaminothiazol-4-yl)-2-difluoromethoxyiminoacetamido]-3-(4-methoxy-2-methyl-1-pyrazolio)methyl-3-cephem-4-carboxylate trifluoroacetate (syn isomer).

IR (Nujol): 1790, 1720, 1685, 1605 cm$^{-1}$

EXAMPLE 204

Benzhydryl 7β-[2-(2-formamidothiazol-4-yl)-2-(2-cyclopenten-1-yloxyimino)acetamido]-3-(4-methoxy-2-methyl-1-pyrazolio)methyl-3-cephem-4-carboxylate trifluoroacetate (syn isomer)

IR (Nujol): 1785, 1720, 1680, 1600 cm$^{-1}$

EXAMPLE 205

Benzhydryl 7β-[2-(2-cyclopenten-1-yloxyimino)-2-(2-formamidothiazol-4-yl)acetamido]-3-(2-methyl-1-pyrazolio)methyl-3-cephem-4-carboxylate iodide (syn isomer).

IR (Nujol): 3300, 1780, 1720, 1670, 1540 cm$^{-1}$

EXAMPLE 206

Benzhydryl 7β-[2-(2-cyclopenten-1-yloxyimino)-2-(2-formamidothiazol-4-yl)acetamido]-3-(2-methyl-1-pyrazolio)methyl- 3-cephem-4-carboxylate trifluoroacetate (syn isomer).

IR (Nujol): 3200, 1780, 1720, 1670, 1540 cm$^{-1}$

EXAMPLE 207

7β-[2-(2-Aminothiazol-4-yl)-2-hydroxyiminoacetamido]-3-(4-methoxy-2-methyl-1-pyrazolio)-methyl-3-cephem-4-carboxylate (syn isomer).

IR (Nujol): 3250, 1765, 1660, 1600 cm$^{-1}$

EXAMPLE 208

7β-[2-(2-Aminothiazol-4-yl)-2-(2-cyclopenten-1-yloxyimino)acetamido]-3-(4-methoxy-2-methyl-1-pyrazolio)methyl-3-cephem-4-carboxylate (syn isomer).

IR (Nujol): 3300, 1675, 1605 cm$^{-1}$

EXAMPLE 209

A mixture of benzhydryl 7β-[2-(2-cyclopenten-1-yloxyimino)-2-(2-formamidothiazol-4-yl)acetamido]-3-(2-methyl-1-pyrazolio)methyl-3-cephem-4-carboxylate 1-oxide iodide (syn isomer, 5.3 g) and N,N-dimethylformamide (50 ml) was stirred at −33° C. and phosphorus trichloride (1.68 g) was added thereto with stirring. The reaction mixture was stirred for 10 minutes at the same temperature, and poured into water (400 ml). Precipitates were collected by filtration and washed with water to give benzhydryl 7β-[2-(2-cyclopenten-1-yloxyimino)-2-(2-formamidothiazol-4-yl)acetamido]-3-(2-methyl-1-pyrazolio)methyl-3-cephem-4-carboxylate iodide (syn isomer, 4.95 g).

IR (Nujol): 3300, 1780, 1720, 1670, 1540 cm$^{-1}$

NMR (DMSO-d$_6$, δ): 2.20 (2H, m), 2.32 (2H, m), 3.30–3.75 (2H, m), 3.85 (3H, s), 5.30 (1H, d, J=5 Hz), 5.30–6.27 (5H, m), 6.90 (1H, t, J=2 Hz), 6.98 (1H, s), 7.43 (11H, m), 8.45 (1H, d, J=2 Hz), 8.54 (1H, s), 8.54 (1H, m), 9.68 (1H, d, J=8 Hz)

EXAMPLE 210

Benzhydryl 7β-[2-(2-cyclopenten-1-yloxyimino)-2-(2-formamidothiazol-4-yl)acetamido]-3-(2-methyl-1-pyrazolio)methyl-3-cephem-4-carboxylate iodide (syn isomer, 4.9 g) was dissolved in tetrahydrofuran (18.75 ml) and water (1.25 ml), the solution was subjected to column chromatography on an ion-exchange resin "Amberlite IRA-400" (Trademark, manufactured by Rohm and Haas Co.) (CF$_3$COO$^\ominus$ form) and eluted with a mixture of water and tetrahydrofuran (1:15). The fractions containing the object compound were collected and evaporated. The residue was triturated with diisopropyl ether to give benzhydryl 7β-[2-(2-cyclopenten-1-yloxyimino)-2-(2-formamidothiazol-4-yl)acetamido]-3-(2-methyl-1-pyrazolio)methyl-3-cephem-4-carboxylate trifluoroacetate (syn isomer, 5.0 g).

IR (Nujol): 3200, 1780, 1720, 1670, 1540 cm$^{-1}$

NMR (DMSO-d$_6$, δ): 2.17 (2H, m), 2.33 (2H, m), 3.43 (2H, m), 3.82 (3H, s), 5.28 (1H, d, J=5 Hz), 5.33–6.25 (5H, m), 6.85 (1H, t, J=2 Hz), 7.37 (11H, m), 8.32 (1H, d, J=2 Hz), 8.47 (1H, br. s), 8.47 (1H, m), 9.62 (1H, d, J=8 Hz)

The following compounds (Examples 211 to 231) were obtained according to a similar manner to that of Example 209.

EXAMPLE 211

7β-[2-(2-Aminothiazol-4-yl)-2-(difluoromethoxyimino)acetamido]-3-(2-methyl-1-pyrazolio)methyl-3-cephem-4-carboxylate (syn isomer).
IR (Nujol): 3400, 1770, 1660, 1600, 1530 cm$^{-1}$

EXAMPLE 212

Trifluoroacetic acid salt of 7β-[2-(2-formamidothiazol-4-yl)-2-methoxyiminoacetamido]-3-(2-methyl-1-pyrazolio)methyl-3-cephem-4-carboxylate (syn isomer).
IR (Nujol): 1785, 1675 cm$^{-1}$

EXAMPLE 213

7β-[2-(2-Aminothiazol-4-yl)-2-(3-thietanyloxyimino)acetamido]-3-(2-methyl-1-pyrazolio)methyl-3-cephem-4-carboxylate (syn isomer). IR (Nujol): 1770, 1660, 1605 cm$^{-1}$

EXAMPLE 214

7β-[2-(2-Aminothiazol-4-yl)-2-(2-cyclopenten-1-yloxyimino)acetamido]-3-(2-methyl-1-pyrazolio)methyl-3-cephem-4-carboxylate (syn isomer).
IR (Nujol): 3300, 1770, 1650, 1610, 1530 cm$^{-1}$

EXAMPLE 215

7β-[2-(2-Aminothiazol-4-yl)-2-isopropoxyiminoacetamido]-3-(2-methyl-1-pyrazolio)methyl-3-cephem-4-carboxylate (syn isomer).
IR (Nujol): 3300, 1770, 1660, 1610, 1530 cm$^{-1}$

EXAMPLE 216

7β-[2-(2-Aminothiazol-4-yl)-2-(2-tetrahydropyranyloxyimino)acetamido]-3-(2-methyl-1-pyrazolio)methyl-3-cephem-4-carboxylate (syn isomer).
IR (Nujol): 3300, 1775, 1680, 1620 cm$^{-1}$

EXAMPLE 217

7β-[2-(2-Aminothiazol-4-yl)-2-(2-cyclopenten-1-yloxyimino)acetamido] -3-(2,5-dimethyl-1-pyrazolio)methyl-3-cephem-4-carboxylate (syn isomer)
IR (Nujol): 3300, 1770, 1660, 1600 cm$^{-1}$

EXAMPLE 218

7β-[2-(2-Aminothiazol-4-yl)-2-(difluoromethoxyimino)acetamido]-3-(2,5-dimethyl-1-pyrazolio)methyl-3-cephem-4-carboxylate (syn isomer)
IR (Nujol): 3300, 1770, 1670, 1610 cm$^{-1}$

EXAMPLE 219

7β-[2-(2-Aminothiazol-4-yl)-2-(3-cyclopenten-1-yloxyimino)acetamido]-3-(2-methyl-1-pyrazolio)methyl-3-cephem-4-carboxylate (syn isomer)
IR (Nujol): 3250, 3100, 1770, 1662, 1608 cm$^{-1}$

EXAMPLE 220

7β-[2-(2-Aminothiazol-4-yl)-2-(hydroxyimino)acetamido]-3-(4-hydroxymethyl-2-methyl-1-pyrazolio)methyl-3-cephem-4-carboxylate (syn isomer)
IR (Nujol): 3200, 1765, 1660, 1600 cm$^{-1}$

EXAMPLE 221

Sulfuric acid salt of 7β-[2-(2-aminothiazol-4-yl)-2-(difluoromethoxyimino)acetamido]-3-(2-methyl-1-pyrazolio)methyl-3-cephem-4-carboxylate (syn isomer)
NMR (D$_2$O, δ): 3.33 and 3.57 (2H, ABq, J=18 Hz), 4.15 (3H, s), 5.30 (1H, d, J=5 Hz), 5.47 (2H, br. s), 5.87 (1H, d, J=5 Hz), 6.73–6.90 (1H, m), 7.0 (1H, t, J=71 Hz), 7.40 (1H, s), 8.20–8.35 (2H, m)

EXAMPLE 222

7β-[2-(2-Aminothiazol-4-yl)-2-hydroxyiminoacetamido]-3-(4-methoxy-2-methyl-1-pyrazolio)methyl-3-cephem-4-carboxylate (syn isomer).
IR (Nujol): 3250, 1765, 1660, 1600 cm$^{-1}$

EXAMPLE 223

7β-[2-(2-Aminothiazol-4-yl)-2-(2-cyclopenten-1-yloxyimino)acetamido]-3-(4-methoxy-2-methyl-1-pyrazolio)methyl-3-cephem-4-carboxylate (syn isomer).
IR (Nujol): 3300, 1675, 1605 cm$^{-1}$

EXAMPLE 224

7β-[2-(2-Aminothiazol-4-yl)-2-methoxyiminoacetamido]-3-(3-formamido-2-methyl-1-pyrazolio)methyl-3-cephem-4-carboxylate (syn isomer).
IR (Nujol): 3350, 1770, 1660, 1610 cm$^{-1}$

EXAMPLE 225

7β-[2-(2-Aminothiazol-4-yl)-2-(difluoromethoxyimino)acetamido]-3-(4-formamido-2-methyl-1-pyrazolio)methyl-3-cephem-4-carboxylate (syn isomer).
IR (Nujol): 1775, 1675, 1605 cm$^{-1}$

EXAMPLE 226

7β-[2-(2-Aminothiazol-4-yl)-2-tertbutoxycarbonylmethoxyiminoacetamido]-3-(3-amino-2-methyl-1-pyrazolio)methyl-3-cephem-4-carboxylate trihydrochloride (syn isomer).
IR (Nujol): 3300, 1775, 1715, 1670, 1630 cm$^{-1}$

EXAMPLE 227

Benzhydryl 7β-[2-(2-tritylaminothiazol-4-yl)-2-(difluoromethoxyimino)acetamido]-3-(4-formamido-2-methyl-1-pyrazolio)methyl-3-cephem-4-carboxylate trifluoroacetate (syn isomer).
IR (Nujol): 1795, 1725, 1675, 1615 cm$^{-1}$

EXAMPLE 228

7β-[2-(2-Aminothiazol-4-yl)-2-carboxymethoxyiminoacetamido]-3-(3-amino-2-methyl-1-pyrazolio)methyl-3-cephem-4-carboxylate (syn isomer).
IR (Nujol): 3300, 1760, 1650 cm$^{-1}$

EXAMPLE 229

7β-[2-(2-Aminothiazol-4-yl)-2-methoxyiminoacetamido]-3-(3-amino-2,4-dimethyl-1-pyrazolio)methyl-3-cephem-4-carboxylate (syn isomer).
IR (Nujol): 3300, 1770, 1640, 1600 cm$^{-1}$

EXAMPLE 230

7β-[2-(2-Aminothiazol-4-yl)-2-(difluoromethoxyimino)acetamido]-3-(3-formamido-2,4-dimethyl-1-pyrazolio)methyl-3-cephem-4-carboxylate (syn isomer).
IR (Nujol): 3250, 1765, 1665, 1650 cm$^{-1}$

EXAMPLE 231

7β-[2-(2-Aminothiazol-4-yl)-2-(difluoromethoxyimino)acetamido]-3-(3-amino-2,4-dimethyl-1-pyrazolio)methyl-3-cephem-4-carboxylate (syn iosmer).

IR (Nujol): 3300, 1765, 1640, 1600 cm$^{-1}$

The following compounds (Examples 232 and 233) were obtained according to a similar manner to that of Example 1.

EXAMPLE 232

7β-2-(2-Aminothiazol-4-yl)-2-hydroxyiminoacetamido]-3-(4-methoxy-2-methyl-1-pyrazolio)methyl-3-cephem-4-carboxylate (syn isomer).

IR (Nujol): 3250, 1765, 1660, 1600 cm$^{-1}$

EXAMPLE 233

7β-[2-(2-Aminothiazol-4-yl)-2-(2-cyclopenten-1-yloxyimino)acetamido]-3-(4-methoxy-2-methyl-1-pyrazolio)methyl-3-cephem-4-carboxylate (syn isomer).

IR (Nujol): 3300, 1675, 1605 cm$^{-1}$

EXAMPLE 234

Sodium carbonate (6.06 g) was added to a suspension of sulfuric acid salt of 7β-[2-(2-aminothiazol-4-yl)-2-(difluoromethoxyimino)acetamido]-3-(2-methyl-1-pyrazolio)methyl-3-cephem-4-carboxylate (syn isomer)(35 g) in water (105 ml) and then the solution was allowed to stand at 3° to 5° C. for 14 hours. The resultant precipitates were collected by filtration, washed with cool water (50 ml) and dried to give crystals of 7β-[2-(2-aminothiazol-4-yl)-2-(difluoromethoxyimino)acetamido]-3-(2-methyl-1-pyrazolio)methyl-3-cephem-4-carboxylate dihydrate (syn isomer) (23.8 g).

mp: 249°-251° C.

IR (Nujol): 3480, 3150, 1775, 1650, 1610, 1530 cm$^{-1}$

EXAMPLE 235

1N-Hydrochloric acid (3.9 ml) was added to a solution of 7β-[2-(2-aminothiazol-4-yl)-2-(difluoromethoxyimino)acetamido]-3-(2-methyl-1-pyrazolio)methyl-3-cephem-4-carboxylate dihydrate (syn isomer) (2 g) in water (50 ml). The resultant aqueous solution was lyophilized to give 7β-[2-(2-aminothiazol-4-yl)-2-(difluoromethoxyimino)acetamido]-3-(2-methyl-1-pyrazolio)methyl-3-cephem-4carboxylate hydrochloride (syn isomer) (2.1 g).

IR (Nujol): 3120, 1780, 1670, 1630, 1530 cm$^{-1}$

NMR (D$_2$O, δ): 3.28 and 3.60 (2H, ABq, J=18 Hz), 4.13 (3H, s), 5.30 (1H, d, J=5 Hz), 5.35 and 5.53 (2H, ABq, J=14 Hz), 5.87 (1H, d, J=5 Hz), 6.80 (1H, t, J=3 Hz), 6.87 (1H, t, J=72 Hz), 7.37 (1H, s), 8.23 (2H, d, J=3 Hz).

EXAMPLE 236

7β-[2-(2-Aminothiazol-4-yl)-2-(difluoromethoxyimino)acetamido]-3-(2-methyl-1-pyrazolio)methyl-3-cephem-4-carboxylate dihydrochloride (syn isomer) (1.02 g) was obtained by treating 7β-[2-(2-aminothiazol-4-yl)-2-(difluoromethoxyimino)acetamido]-3-(2-methyl-1-pyrazolio)methyl-3-cephem-4-carboxylate dihydrate (syn isomer)(1 g) with 1N hydrochloric acid (3.9 ml) according to a similar manner to that of Example 235.

IR (Nujol): 3200 (broad), 1780, 1670, 1630, 1540 cm$^{-1}$

NMR (D$_2$O, δ): 3.33 and 3.65 (2H, ABq, J=18 Hz), 4.15 (3H, s), 5.33 (1H, d, J=5 Hz), 5.52 (2H, s), 5.88 (1H, d, J=5 Hz), 6.82 (1H, t, J=3 Hz), 6.98 (1H, t, J=72 Hz), 7.42 (1H, s), 8.25 (2H, d, J=3 Hz).

Preparation 31

A mixture of 2-(2-formamidothiazol-4-yl)-2-(2-cyclopenten-1-yloxyimino)acetic acid (100 g) (syn isomer) (RS mixture), (R)-(+)-1-phenylethylamine (38.8 g) and ethanol (100 ml) was stirred at ambient temperature for 3 hours. The precipitates crystallized out of the solution were collected by filtration, washed with ethanol and diisopropyl ether to give their crude salt (50 g). The salt was dissolved in ethanol (750 ml) under reflux, and cooled. The first precipitates were filtered off and the filtrate was allowed to stand at ambient temperature for 4 days. The precipitates crystallized out of the solution were collected by filtration, washed with ethanol and diisopropyl ether to give (R)-(+)-1-phenylethylamine salt of one isomer of 2-(2-formamidothiazol-4-yl)-2-(2-cyclopenten-1-yloxyimino)acetic acid (17.3 g) (syn isomer).

Sodium bicarbonate (7.1 g) was added to a solution of the salt obtained above (17 g) in ethyl acetate (200 ml) and water (200 ml), and the mixture was stirred at ambient temperature for 3 hours. The separated aqueous layer was adjusted to pH 2.5 with 6N-hydrochloric acid. The precipitates were collected by filtration, washed with water to give one isomer of 2-(2-formamidothiazol-4-yl)-2-(2-cyclopenten-1-yloxyimino)acetic acid (11.2 g) (syn isomer).

mp: 160° C. (dec.)

[α]$_D$ = −25.5° (c=1.0%, MeOH:H$_2$O=1:1)

IR (Nujol): 3200, 3100, 3050, 2570, 2400, 1705, 1690, 1590, 1550 cm$^{-1}$

Hereinafter this isomer is referred to as "A isomer" and a compound derived from this isomer is also referred to as "A isomer".

Preparation 32

A mixture of 2-(2-formamidothiazol-4-yl)-2-(2-cyclopenten-1-yloxyimino)acetic acid (syn isomer, RS mixture) (100 g) and (S)-(−)-1-phenylethylamine (38.8 g) in ethanol (500 ml) was stirred at ambient temperature for 18 hours. The precipitates crystallized out of the solution were collected by filtration, washed with ethanol and diisopropyl ether to give their crude salt (71.7 g).

The salt (70 g) was dissolved in ethanol (1050 ml) under reflux and then cooled. The resultant precipitates were collected by filtration, washed with ethanol and diisopropyl ether to give (S)-(−)-1-phenylethylamine salt of the other isomer of 2-(2-formamidothiazol-4-yl)-2-(2-cyclopenten-1-yloxyimino)acetic acid (31.5 g).

This salt (30 g) was converted to free acid according to a similar manner to that of Preparation 31 to give the other isomer of 2-(2-formamidothiazol-4-yl)-2-(2-cyclopenten-1-yloxyimino)acetic acid (syn isomer) (19.36 g).

mp: 164° C. (dec.)

[α]$_D$ = +22.3° (c=1.0%, MeOH:H$_2$O=1:1)

IR (Nujol): 3200, 3100, 3050, 2570, 2400, 1715, 1710, 1595, 1560 cm$^{-1}$

Hereinafter this isomer is referred to as "B isomer" and a compound derived from this isomer is also referred to as "B isomer".

EXAMPLE 237

N,N-Dimethylformamido (0.75 g) and phosphoryl chloride (1.57 ml) were mixed to prepare Vilsmeier reagent in a usual manner, and the resultant Vilsmeier reagent was suspended in dry ethyl acetate (22 ml). To the suspension was added 2-(2-formamidothiazol-4-yl)-2-(2-cyclopenten-1-yloxyimino) acetic acid (A isomer)

(syn isomer) (2.3 g) under ice-cooling with stirring, and then the mixture was stirred for an hour to prepare an activated acid solution. To a solution of bis(trifluoroacetic acid )salts of 7β-amino-3-(2-methyl-1-pyrazolio)-methyl-3-cephem-4-carboxylate (4.7 g) and N-mono(-trimethylsilyl)acetamido (11.8 g) in ethyl acetate (50 ml) was added the activated acid solution prepared above at 3° C. After stirring at the same temperature for an hour, the mixture was poured into diisopropyl ether (500 ml). The precipitates were collected by filtration and successively washed with diisopropyl ether to give trifluoroacetic acid salt of 7β-[2-(2-formamidothiazol-4-yl)-2-(2-cyclopenten-1-yloxyimino)acetamido]-3-(2-methyl-1-pyrazolio)methyl-3-cephem-4-carboxylate (A isomer) (syn isomer) (6.02 g).

IR (Nujol): 3100, 1780, 1660, 1540 cm$^{-1}$

NMR (DMSO-d$_6$, δ): 2.07 (2H, m), 2.30 (2H, m), 3.38 (2H, broad s), 4.03 (3H, s), 5.17 (1H, d, J=5 Hz), 5.40 (1H, m), 5.53 (2H, broad s), 5.87 (1H, dd, J=5 Hz and 8 Hz), 5.95 (2H, m), 6.87 (1H, t, J=3 Hz), 7.32 (1H, s), 8.47 (1H, s), 8.57 (1H, d, J=3 Hz), 9.60 (1H, d, J=8 Hz)

EXAMPLE 238

Trifluoroacetic acid salt of 7β-[2-(2-formamidothiazol-4-yl)-2-(2-cyclopenten-1-yloxyimino)acetamido]-3-(2-methyl-1-pyrazolio)methyl-3-cephem-4-carboxylate (B isomer) (syn isomer) was obtained from 2-(2-formamidothiazol-4-yl)-2-(2-cyclopenten-1-yloxyimino)acetic acid (B isomer) (syn isomer) and bis(trifluoroacetic acid) salt of 7β-amino-3-(2-methyl-1-pyrazolio)methyl-3-cephem-4-carboxylate according to a similar manner to that of Example 237.

IR (Nujol): 3150, 1780, 1660, 1540 cm$^{-1}$

NMR (DMSO-d$_6$, δ): 2.10 (2H, m), 2.33 (2H, m), 3.40 (2H, broad s), 4.07 (3H, s), 5.20 (1H, d, J=5 Hz), 5.22 (1H, m), 5.57 (2H, broad s), 5.93 (1H, dd, J=5 Hz and 8 Hz), 5.80-6.20 (2H, m), 6.90 (1H, t, J=3 Hz), 7.35 (1H, s), 8.50 (1H, s), 8.67 (1H, d, J=3 Hz), 9.60 (1H, d, J=8 Hz)

EXAMPLE 239

Conc. hydrochloric acid (4.1 g) was added to a solution of trifluoroacetic acid salt of 7β-[2-(2-formamidothiazol-4-yl)-2-(2-cyclopenten-1-yloxyimino)acetamido]-3-(2-methyl-1-pyrazolio)methyl-3-cephem-4-carboxylate (A isomer) (syn isomer) (5.8 g) in methanol (60 ml), and the mixture was stirred at ambient temperature for 2 hours. To the reaction mixture was added water (60 ml) and adjusted to pH 2.0 with 5% aqueous solution of sodium bicarbonate. The separated aqueous solution was subjected to column chromatography on macroporous non-ionic adsorption resin "Diaion HP-20" (120 ml) and eluted with 30% aqueous solution of methanol. The fractions containing the object compound were collected and concentrated in vacuo, then lyophilized to give 7β-[2-(2-aminothiazol-4-yl)-2-(2-cyclopenten-1-yloxyimino)acetamido]-3-(2-methyl-1-pyrazolio)methyl-3-cephem-4-carboxylate (A isomer) (syn isomer) (1.1 g).

[α]$_D$= +38.5° (C=1.0 %, MeOH:H$_2$O=1:1)
IR (Nujol): 3300, 1770, 1660, 1610, 1530 cm$^{-1}$
NMR (D$_2$O-NaHCO$_3$, δ): 2.10 (2H, m), 2.34 (2H, m), 3.13 and 3.43 (2H, ABq, J=18 Hz), 4.06 (3H, s), 5.16 (1H, d, J=5 Hz), 5.30 (1H, m), 5.18 and 5.48 (2H, ABq, J=14 Hz), 5.75 (1H, d, J=5 Hz), 5.88 (1H, m), 6.10 (1H, m), 6.70 (1H, t, J=3 Hz), 6.86 (1H, s), 8.10 (2H, m)

EXAMPLE 240

7β-[2-(2-Aminothiazol-4-yl)-2-(2-cyclopenten-1-yloxyimino)acetamido]-3-(2-methyl-1-pyrazolio)methyl-3-cephem-4-carboxylate (B isomer) (syn isomer) was obtained according to a similar manner to that of Example 239.

[α]$_D$= +64° (C=1.0%, MeOH:H$_2$O=1:1)
IR (Nujol): 3250, 1760, 1660, 1600, 1615 cm$^{-1}$
NMR (D$_2$O-NaHCO$_3$, δ): 2.10 (2H, m), 2.32 (2H, m), 3.13 and 3.42 (2H, ABq, J=18 Hz), 4.06 (3H, s), 5.16 (1H, d, J=5 Hz), 5.30 (1H, m), 5.20 and 5.43 (2H, ABq, J=14 Hz), 5.75 (1H, d, J=5 Hz), 5.90 (1H, m), 6.10 (1H, m), 6.70 (1H, t, J=3 Hz), 6.87 (1H, s), 8.10 (2H, m)

What we claim is:

1. A new cephem compound of the formula:

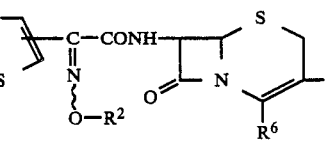

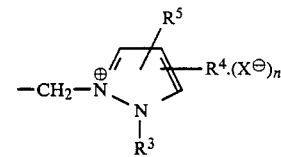

wherein
$R^1$ is amino or protected amino,
$R^2$ is lower alkyl, dihalogenated lower alkyl, carboxy(lower)alkyl or protected carboxy(lower)alkyl,
$R^3$ is lower alkyl,
$R^4$ and $R^5$ are each hydrogen, lower alkyl, hydroxy(lower)alkyl, lower alkoxy, amino or protected amino,
$R^6$ is COO$^\ominus$, carboxy or protected carboxy,
$X^\ominus$ is an anion, and
n is 0 or 1,
with proviso that
  (i) when $R^2$ is carboxy(lower)alkyl or protected carboxy(lower)alkyl, then $R^4$ is hydrogen and $R^5$ is amino,
  (ii) when $R^6$ is COO$^\ominus$, then n is 0, and
  (iii) when $R^6$ is carboxy or protected carboxy, then n is 1, and a pharmaceutically acceptable salt thereof.

2. A syn isomer of the compound of claim 1.

3. A compound of claim 2, wherein $R^2$ is lower alkyl, dihalogenated lower alkyl, cyclo(lower)alkenyl selected from the group consisting of cyclopropenyl, cyclobutenyl, cyclopentenyl and cyclohexenyl or thietanyl.

4. A compound of claim 3, wherein
$R^1$ is amino,
$R^2$ is lower alkyl or dihalogenated lower alkyl,
$R^4$ and $R^5$ are each hydrogen, lower alkyl or amino, and
$R^6$ is COO$^\ominus$.

5. A compound of claim 4, wherein
$R^2$ is dihalogenated lower alkyl,
$R^4$ and $R^5$ are each hydrogen.

6. A compound of claim 5, which is

7β-[2-(2-aminothiazol-4-yl)-2-(difluoromethox-
yimino)acetamido]-3-(2-methyl-1-pyrazolio)methyl-
3-cephem-4-carboxylate (syn isomer).

7. A compound of claim 5, which is
sulfuric acid salt of 7β-[2-(2-aminothiazol-4-yl)-2-(di-
fluoromethoxyimino)acetamido]-3-(2-methyl-1-
pyrazolio)methyl-3-cephem-4-carboxylate (syn iso-
mer).

8. A compound of claim 4,
wherein
R⁴ is lower alkyl, and
R⁵ is amino.

9. A compound of claim 8, which is selected from a group consisting of:
7β-[2-(2-aminothiazol-4-yl)-2-methox-
yiminoacetamido]-3-(3-amino-2,4-dimethyl-1-
pyrazolio)methyl-3-cephem-4-carboxylate (syn iso-
mer) and
7β-[2-(2-aminothiazol-4-yl)-2-(difluoromethox-
yamino)acetamido]-3-(3-amino-2,4-dimethyl-1-
pyrazolio)methyl-3-cephem-4-carboxylate (syn iso-
mer).

10. An antimicrobial pharmaceutical composition which comprises, as an active ingredient, an antimcrobi-ally effective amount of a compound of claim 1 or a pharmaceutically acceptable salt thereof in admixture with pharmaceutically acceptable carriers.

11. A method for the treatment of infectious diseases which comprises administering an antimicrobially effec-tive amount of a compound of claim 1 or a pharmaceuti-cally acceptable salt thereof to a human or animal.

12. A compound of the formula:

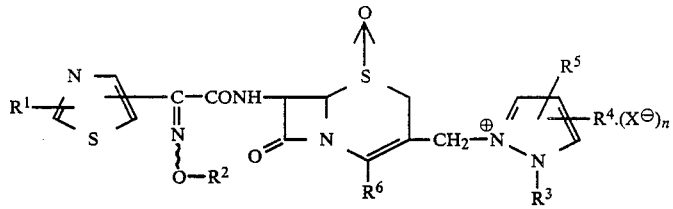

wherein
R¹ is amino or protected amino,
R² is lower alkyl, dihalogenated lower alkyl, carbox-y(lower)alkyl or protected carboxy(lower)alkyl,
R³ is lower alkyl,
R⁴ and R⁵ are each hydrogen, lower alkyl, hydroxy(-lower)alkyl, lower alkoxy, amino or protected amino,
R⁶ is COO⊖, carboxy or protected carboxy,
X⊖ is an anion, and
n is 0 or 1,
with proviso that
(i) when R² is carboxy(lower)alkyl or protected car-boxy(lower)alkyl, then R⁴ is hydrogen and R⁵ is amino,
(ii) when R⁶ is COO⊖, then n is 0, and
(iii) when R⁶ is carboxy or protected carboxy, then n is 1, and its salt.

* * * * *